(12) United States Patent
Brown et al.

(10) Patent No.: US 8,691,931 B2
(45) Date of Patent: Apr. 8, 2014

(54) ORGANIC ELECTRONIC DEVICES AND POLYMERS, INCLUDING PHOTOVOLTAIC CELLS AND DIKETONE-BASED AND DIKETOPYRROLOPYRROLE-BASED POLYMERS

(75) Inventors: Christopher T. Brown, Pittsburgh, PA (US); Christophe René Gaston Grenier, Pittsburgh, PA (US); Chad Landis, Oakmont, PA (US); Elena E. Sheina, Pittsburgh, PA (US); Ting Xu, Pittsburgh, PA (US)

(73) Assignee: Plextronics, Inc., Pittsburgh, PA (US)

( * ) Notice: Subject to any disclaimer, the term of this patent is extended or adjusted under 35 U.S.C. 154(b) by 192 days.

(21) Appl. No.: 12/874,137

(22) Filed: Sep. 1, 2010

(65) Prior Publication Data

US 2011/0114184 A1 May 19, 2011

Related U.S. Application Data

(60) Provisional application No. 61/240,137, filed on Sep. 4, 2009, provisional application No. 61/241,813, filed on Sep. 11, 2009, provisional application No. 61/248,335, filed on Oct. 2, 2009, provisional application No. 61/289,314, filed on Dec. 22, 2009, provisional application No. 61/290,844, filed on Dec. 29, 2009, provisional application No. 61/307,387, filed on Feb. 23, 2010.

(51) Int. Cl.
*C08G 14/10* (2006.01)
(52) U.S. Cl.
USPC ............. 528/163; 528/117; 528/94; 136/263; 526/257; 549/15
(58) Field of Classification Search
USPC ............. 528/163, 117, 94; 136/263; 526/257; 549/15
See application file for complete search history.

(56) References Cited

U.S. PATENT DOCUMENTS

| | | | |
|---|---|---|---|
| 4,356,429 | A | 10/1982 | Tang |
| 4,539,507 | A | 9/1985 | Van Slyke et al. |
| 4,585,878 | A | 4/1986 | Jost et al. |
| 4,778,899 | A | 10/1988 | Pfenninger et al. |
| 4,931,566 | A | 6/1990 | Surber et al. |
| 5,247,190 | A | 9/1993 | Friend et al. |
| 5,401,827 | A | 3/1995 | Holmes et al. |
| 7,569,159 | B2 | 8/2009 | Hammond et al. |
| 2006/0078761 | A1 | 4/2006 | Williams et al. |
| 2008/0248313 | A1 | 10/2008 | Seshadri et al. |
| 2008/0299293 | A1 | 12/2008 | Sheina et al. |
| 2008/0319207 | A1 | 12/2008 | Laird et al. |
| 2009/0108255 | A1 | 4/2009 | Bazan et al. |
| 2009/0256117 | A1 | 10/2009 | Seshadri et al. |
| 2009/0299029 | A1 | 12/2009 | Chan |
| 2010/0043876 | A1 | 2/2010 | Tuttle et al. |

FOREIGN PATENT DOCUMENTS

| | | |
|---|---|---|
| EP | 0094911 B1 | 9/1986 |
| EP | 0133156 B1 | 7/1991 |
| EP | 0181290 B1 | 9/1991 |
| EP | 0302018 B1 | 11/1993 |
| EP | 0672729 B1 | 9/1999 |
| EP | 0962499 A2 | 12/1999 |
| EP | 0962499 B2 | 3/2008 |
| EP | 2034537 A2 | 3/2009 |
| JP | 2007266285 | 10/2007 |
| WO | WO 2008/000664 A1 | 1/2008 |
| WO | WO 2008/018931 A2 | 2/2008 |
| WO | WO 2009/103030 A1 | 8/2009 |
| WO | WO 2010/108873 A1 | 9/2010 |

OTHER PUBLICATIONS

Partial International Search Report in corresponding PCT Application PCT/US2010/047567, 2010.
Lijun, H. et al., "Bandgap and Molecular Level Control of the Low-Bandgap Polymers Based on 3,6-Dithi ophen-2-yl-2,5-dihydropyrrol 0[3,4-c]pyrrole-I,4-dione toward Highly Efficient Polymer Solar Cells", 42 Macromolecules 6564 (2009).
Vala, M. et al., "Novel, soluble diphenyl-diketo-pyrrolopyrroles: Experimental and theoretical study", 84 Dyes and Pigments 176 (2009).
XP002613086, Database WPI, Week 200845, Thomson Scientific, London, GB; AN 2008-H07101, 2008.
U.S. Appl. No. 61/108,851, filed Oct. 27, 2008, Seshadri et al.

U.S. Appl. No. 61/115,877, filed Nov. 18, 2008, Seshadri et al.
U.S. Appl. No. 61/116,963, filed Nov. 21, 2008, Benson-Smith et al.
Avcibasi, N. et al., "Synthesis and in vitro evaluation of dioxopyrrolopyrroles as potential low-affinity fluorescent Ca2+ indicators," 6 *Int. J. Photoenergy* 159 (2004).
Bao, Z. et al., "Exploration of the Stille Coupling Reaction for the Synthesis of Functional Polymers," 117 J. Am. Chem. Soc. 12426 (1995).
Billmeyer Jr., F., *Textbook of Polymer Science*, 3rd Ed., ch. 5, John Wiley & Sons, Inc. (1984).
Blouin, N. et al., "Poly(2,7-carbazole)s: Structure—Property Relationships," 42 *Acc. Chem. Res.* 1110 (2008).
Blouin, N. et al., "Toward a Rational Design of Poly(2,7-Carbazole) Derivatives for Solar Cells," 130 *J. Am. Chem. Soc.* 732 (2008).
Brockmann, T., "Synthesis and Properties of Low-Bandgap Zwitterionic and Planar Conjugated Pyrrole-Derived Polymeric Sensors. Reversible Optical Absorption Maxima from the UV to the Near-IR," 117 *J. Am. Chem. Soc.* 4437 (1995).
Brown, P., "Effect of interchain interactions on the absorption and emission of poly(3-hexylthiophene)," 67 *Phys. Rev. B* 064203 (2003).
Bundgaard, E. et al., "Large-area photovoltaics based on low band gap copolymers of thiophene and benzothiadiazole or benzobis(thiadiazole)," 91 *Solar Energy Materials and Solar Cells* 1019 (2007).
Burgi, L. et al., "High-Mobility Ambipolar Near-Infrared Light-Emitting Polymer Field-Effect Transistors," 20 *Adv. Mater.* 2217 (2008).
Cao, D. et al., "Synthesis and characterization of novel red-emitting alternating copolymers based on fluorene and diketopyrrolopyrrole derivatives," 44 J. Polymer Sci. Part A 2395 (2006).
Chen, L. et al., "Recent Progress in Polymer Solar Cells: Manipulation of Polymer:Fullerene Morphology and the Formation of Efficient Inverted Polymer Solar Cells," 21 *Adv. Mater.* 1434 (2009).
Farina, V. et al., "Large rate accelerations in the stille reaction with tri-2-furylphosphine and triphenylarsine as palladium ligands," 113 J. Am. Chem. Soc. 9585 (1991).
Gamota, D., ed., et al., *Printed Organic and Molecular Electronics* (2004).
Guo, X. et al., "Phthalimide-Based Polymers for High Performance Organic Thin-Film Transistors," 131 *J. Am. Chem. Soc.* 7206 (2009).
Hirsch, A. et al., *Fullerenes Chemistry and Reactions*, Wiley-VCH Verlag, Weinheim (2005).
Hoppe, H. et al., "Polymer Solar Cells," 214 *Adv. Polymer Sci.* 1 (2008).
Hou, J. et al., "Bandgap and Molecular Energy Level Control of Conjugated Polymer Photovoltaic Materials Based on Benzo[1,2-b:4,5-b']dithiophene," 41 *Macromol.* 6012 (2008).
Hou, J. et al., "Synthesis, Characterization, and Photovoltaic Properties of a Low Band Gap Polymer Based on Silole-Containing Polythiophenes and 2,1,3-Benzothiadiazole," 130 *J. Am. Chem. Soc.* 16144 (2008).
Hou, Q. et al., "Novel red-emitting fluorene-based copolymers," 12 *J. Mater. Chem.* 2887 (2002).
Kim, J., "Assemblies of conjugated polymers: Intermolecular and intramolecular effects on the photophysical properties of conjugated polymers," 74 *Pure Appl. Chem.* 2031 (2002).
Kraft, A. et al., "Electroluminescent Conjugated Polymers—Seeing Polymers in a New Light," 37 *Angew. Chem. Int. Ed.* 402 (1998).
Kuwano, R. et al., "Aqueous Hydroxide as a Base for Palladium-Catalyzed Amination of Aryl Chlorides and Bromides," 67 J. Org. Chem. 6479 (2002).
Li, Z., ed., et al., *Organic Light Emitting Materials and Devices*, CRC Taylor (2006).
Li et al., "Preparation and characterization of galactosylated chitosan nanoparticles as a targeting drug carrier," 96 *Polymeric Materials Science and Engineering (PMSE) Preprints* 757 (2007).
Liang, Y. et al., "Development of New Semiconducting Polymers for High Performance Solar Cells," 131 *J. Am. Chem. Soc.* 56 (2009).
Liang, Y. et al., "Highly Efficient Solar Cell Polymers Developed via Fine-Tuning of Structural and Electronic Properties," 131 J. Am. Chem. Soc. 7792 (2009).

Liu, K. et al., "Novel 1,4-diketo-3,6-diphenyl pyrrolo[3,4-c]pyrrole (DPP)-based copolymers with large Stokes shift," 111 *J. App. Polymer Sci.* 1976 (2009).
Love, E. et al., "The Use of Salicylaldehyde Phenylhydrazone as an Indicator for the Titration of Organometallic Reagents," 64 J. Org. Chem. 3755 (1999).
Miyaura, E., *Cross-Coupling Reactions A Practical Guide* (2002).
Negishi, E., Handbook of Organopalladium Chemistry for Organic Synthesis (2002).
Nielsen, C. et al., "New Regiosymmetrical Dioxopyrrolo- and Dihydropyrrolo-Functionalized Polythiophenes," 6 *Org. Letters* 3381 (2004).
Peet, J. et al., "Efficiency enhancement in low-bandgap polymer solar cells by processing with alkane dithiols," 6 *Nat. Mater.* 497 (2007).
Peet, J. et al., "Small molecule sensitizers for near-infrared absorption in polymer bulk heterojunction solar cells," 93 *Appl. Phys. Lett.* 163306 (2009).
Petrova-Koch, V., ed., et al., *High-Efficient Low-Cost Photovoltaics*, Springer (2009).
Pomerantz, M et al., "Ester substituted bithiophenes. Abnormally low dihedral angle and rotation barrier due to dipolar stabilization," 40 *Tetrahedron Lett.* 3317 (1999).
Pomerantz, M., "Planar 2,2'-bithiophenes with 3,3'- and 3,3',4,4'-substituents. A computational study," 44 *Tetrahedron Lett.* 1563 (2003).
Pomerantz, M et al., "Studies of planar poly(3,4-disubstituted-thiophenes)," 135-136 *Synth. Met.* 257 (2003).
Pope, M. et al., *Electronic Processes in Organic Crystals and Polymers*, 2nd ed., Oxford University Press (1999).
Radke, R. et al., "Highly Fluorescent Oligothiophenes through the Incorporation of Central Dithieno[3,2-b:2',3'-d]pyrrole Units," 7 *Org. Lett.* 5253 (2005).
Schmidt, R. et al., "High-Performance Air-Stable n-Channel Organic Thin Film Transistors Based on Halogenated Perylene Bisimide Semiconductors," 131 *J. Am. Chem. Soc.* 6215 (2009).
Skotheim, T. ed. et al., *Handbook of Conducting Polymers*, (3d ed. 1998).
Smith, M., ed., et al., *March's Advanced Organic Chemistry: Reactions, Mechanisms, and Structure*, 6th ed, Wiley (2007).
Stille, J., "The Palladium-Catalyzed Cross-Coupling Reactions of Organotin Reagents with Organic Electrophiles [New Synthetic Methods (58)]," 25 Angew. Chem. Int. Ed., Engl. 508 (1986).
Sun, S., ed., et al., *Organic Photovoltaics: Mechanisms, Materials, and Devices*, CRC Press (2005).
Tamayo, A. et al., "Design, Synthesis, and Self-assembly of Oligothiophene Derivatives with a Diketopyrrolopyrrole Core," 112 *J. Phys. Chem. C* 15543 (2008).
Tamayo, A. et al., "A low band gap, solution processable oligothiophene with a dialkylated diketopyrrolopyrrole chromophore for use in bulk heterojunction solar cells," 94 *App. Phys. Lett.* 103301 (2009).
Tantiwiwat, M. et al., "Oligothiophene Derivatives Functionalized with a Diketopyrrolopyrrolo Core for Solution-Processed Field Effect Transistors: Effect of Alkyl Substituents and Thermal Annealing," 111 *J. Phys. Chem. C* 17402 (2008).
Tovar, J. et al., "Poly(naphthodithiophene)s: Robust, Conductive Electrochromics via Tandem Cyclization-Polymerizations," 13 *Adv. Mater.* 1775 (2001).
Vala, M. et al., "Comparative Studies of Diphenyl-Diketo-Pyrrolopyrrole Derivatives for Electroluminescence Applications," 18 *J. Fluorescence* 1181 (2008).
Van Mullekom et al., "Developments in the chemistry and band gap engineering of donor-acceptor substituted conjugated polymers," 32 *Mat. Sci. Eng. R* 1 (2001).
Walzer, K. et al., "Highly Efficient Organic Devices Based on Electrically Doped Transport Layers," 107 *Chem Rev.* 1233 (2007).
Wienk, M. et al., "Narrow-Bandgap Diketo-Pyrrolo-Pyrrole Polymer Solar Cells: The Effect of Processing on the Performance," 20 *Adv. Mat.* 2556 (2008).
Woo, C. et al., "The Influence of Poly(3-hexylthiophene) Regioregularity on Fullerene-Composite Solar Cell Performance," 130 J. Am. Chem. Soc. 16324 (2008).

Yamamoto, T. et al., "Preparation of π-conjugated poly(thiophene-2,5-diyl), poly(p-phenylene), and related polymers using zerovalent nickel complexes," 25 Macromolecules 1214 (1992).

Zhang, Q. et al, "Alternating Donor/Acceptor Repeat Units in Polythiophenes. Intramolecular Charge Transfer for Reducing Band Gaps in Fully Substituted Conjugated Polymers," 120 *J. Am. Chem. Soc.* 5355 (2008).

Zhang, Q. et al, "Low Optical Bandgap Polythiophenes by an Alternating Donor/Acceptor Repeat Unit Strategy," 119 *J. Am. Chem. Soc.* 5065 (1997).

Zhou, E. et al., "Synthesis and Photovoltaic Properties of Diketopyrrolopyrrole-Based Donor-Acceptor Copolymers," 21 Chem. Mat. 4055 (2009).

Zhu, Y., *New Diketopyrrolopyrrole(DPP)-Based Conjugated Polymers Prepared upon Palladium Catalyzed Polymerization and Electropolymerization Reactions*, Dissertation, University of Koln (2006).

*Primary Examiner* — Shane Fang

(74) *Attorney, Agent, or Firm* — The Marbury Law Group. PLLC

(57) ABSTRACT

Polymers which can be used in p-type materials for organic electronic devices and photovoltaic cells. Compounds, monomers, dimers, trimers, and polymers comprising:

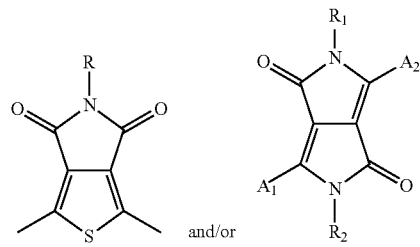

and/or wherein A1 and A2 each independently comprise a fused ring system comprising at least two fused rings directly covalently linked to the pyrrole rings. Good photovoltaic efficiency and lifetime can be achieved. The R group can provide solubility, environmental stability, and fine tuning of spectroscopic and/or electronic properties. Different polymer microstructures can be prepared which encourage multiple band gaps and broad and strong absorptions. The carbonyl can interact with adjacent thiophene rings to provide backbone with rigidity, induce planarity, and reduce and/or eliminate intramolecular chain twisting defects.

20 Claims, 10 Drawing Sheets

ORGANIC ELECTRONIC DEVICES AND POLYMERS, INCLUDING PHOTOVOLTAIC CELLS AND DIKETONE-BASED AND DIKETOPYRROLOPYRROLE-BASED POLYMERS

RELATED APPLICATIONS

This application claims priority to U.S. provisional application Ser. Nos. 61/240,137 filed Sep. 4, 2009; 61/241,813 filed Sep. 11, 2009; 61/248,335 filed Oct. 2, 2009; 61/289,314 filed Dec. 22, 2009; 61/290,844 filed Dec. 29, 2009; and 61/307,387 filed Feb. 23, 2010, which are each hereby incorporated by reference in its entirety.

INTRODUCTION

A need exists to provide better electronic and photonic devices including better solar cells or photovoltaic devices. If some aspects of the devices are based on organic materials, including organic polymers, cost reduction can be achieved.

In particular, a need exists to provide better active layers for organic photovoltaic devices. These active layers can comprise a combination of p-type material and n-type material. The p-type material can be a conjugated polymer. The polymer ideally should satisfy a variety of chemico-physical properties, such as solubility, processability, good film formation, proper absorption properties, proper HOMO/LUMO (molecular orbitals and energy levels), bandgap, charge carrier mobility, and other properties. However, achievement of combinations of properties can be difficult, and gaining one property may result in the sacrifice of another.

For a review of organic photovoltaic technology, see, for example, Sun and Saraciftci (Eds.), *Organic Photovoltaics, Mechanisms, Materials, and Devices*, CRC, 2005.

SUMMARY

Embodiments provided herein including compositions, including monomer, oligomer, and polymer compositions, devices, and methods of making and using the same.

One embodiment provided herein comprises materials, including an oligomer or a polymer, having a donor-acceptor structure, wherein the donor comprises a fused ring system which is directly and covalently linked to an acceptor structure comprising diketopyrrolopyrrole structure. Particularly embodiments are provided, wherein the fused ring system comprises a fused thiophene ring which is directly, covalently linked to the acceptor structure.

Another embodiment provides a composition comprising an oligomer or a polymer having a donor-acceptor structure, wherein the acceptor comprises a diketopyrrolopyrrole structure which is not directly and covalently linked to a donor structure by an unfused thiophene or an unfused benzene ring.

One embodiment provides a device comprising: at least one cathode; at least one anode; at least one photovoltaic active layer disposed between the cathode and anode and comprising at least one p-type material and at least one n-type material, wherein the p-type material comprises at least one polymer comprising a polymer backbone moiety:

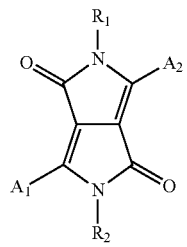

(VIII)

wherein A1 and A2 each independently comprise a fused ring system comprising at least two fused rings directly covalently linked to the substructure of VIII represented as substructure IX:

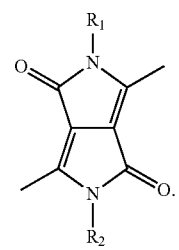

(IX)

In one embodiment, the at least two fused rings form part of the backbone and none of the fused rings form side groups to the backbone.

Another embodiment provides this polymer independently of the device. The polymer can be also disposed on a substrate.

Another embodiment provides a device comprising: at least one cathode; at least one anode; at least one photovoltaic active layer disposed between the cathode and anode and comprising at least one p-type material and at least one n-type material, wherein the p-type material comprises at least one polymer comprising a polymer backbone moiety:

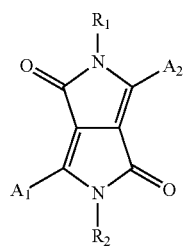

(VIII)

wherein A1 and A2 each independently do not comprise an unfused thiophene or unfused benzene ring directly covalently linked to the substructure of VIII represented as substructure IX:

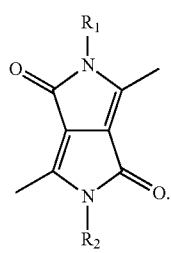

(IX)

Another embodiment provides this polymer independently of the device. The polymer can be also disposed on a substrate.

One embodiment provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

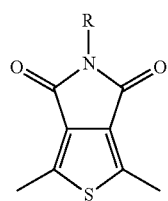

(I)

One embodiment provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

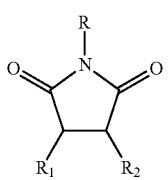

(V)

wherein the moiety V is bivalently linked to the polymer backbone via the $R_1$ and $R_2$ groups, and the $R_1$ and $R_2$ groups form a ring.

One embodiment provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

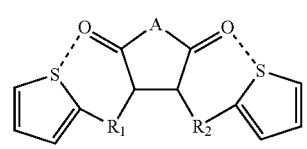

(VI)

wherein A can be a heteroatom, and wherein the moiety V is bivalently linked to the polymer backbone via the illustrated thiophene rings linked to the $R_1$ and $R_2$ groups, and the $R_1$ and $R_2$ groups form a ring.

One embodiment provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

(VII)

wherein A can be a heteroatom, and wherein the moiety VII is linked to the polymer backbone via the illustrated thiophene rings.

Additional embodiments include the monomer, dimer, trimer, oligomer, and polymer compositions described herein, as well as ink compositions comprising same. Coated substrates can be prepared, wherein the substrate is any solid surface including, for example, glasses, ceramics, metals, and polymers.

Additional embodiments include the methods of making and using the polymer compositions described herein.

At least one advantage of at least one embodiment is good photovoltaic performance including efficiency (including power conversion efficiency), fill factor, open circuit voltage, and/or short circuit current, and combinations thereof.

At least one additional advantage for at least one embodiment is improved lifetime and environmental stability.

At least one additional advantage of at least one embodiment is high molar absorptivity sometimes referred to as Alpha and/or molar absorption/extinction coefficient.

At least one additional advantage of at least one embodiment is an absorption profile with vibronic structure or features. This can provide, for example, broader absorption bands. Vibronic structure can be observed in the solid state or in solution.

At least one additional advantage of at least one embodiment is good charge mobility At least one additional advantage of at least one embodiment is good exciton diffusion length.

At least one additional advantage of at least one embodiment is extended conjugation length.

At least one additional advantage is use of less hindered pendant groups and more rigid donor-chromophores.

At least one additional advantage of at least one embodiment is good processability At least one additional advantage of at least one embodiment is presence of order in the film as detected by, for example, x-ray diffraction.

At least one additional advantage of at least one embodiment is improved formation of bulk heterojunction.

At least one additional advantage of at least one embodiment is improved polymer solubility, including improved solubility coupled with relatively high molecular weight. Relatively high molecular weight can be achieved despite the rigidity of the polymer backbone.

DETAILED DESCRIPTION

Introduction

Figure 1A:
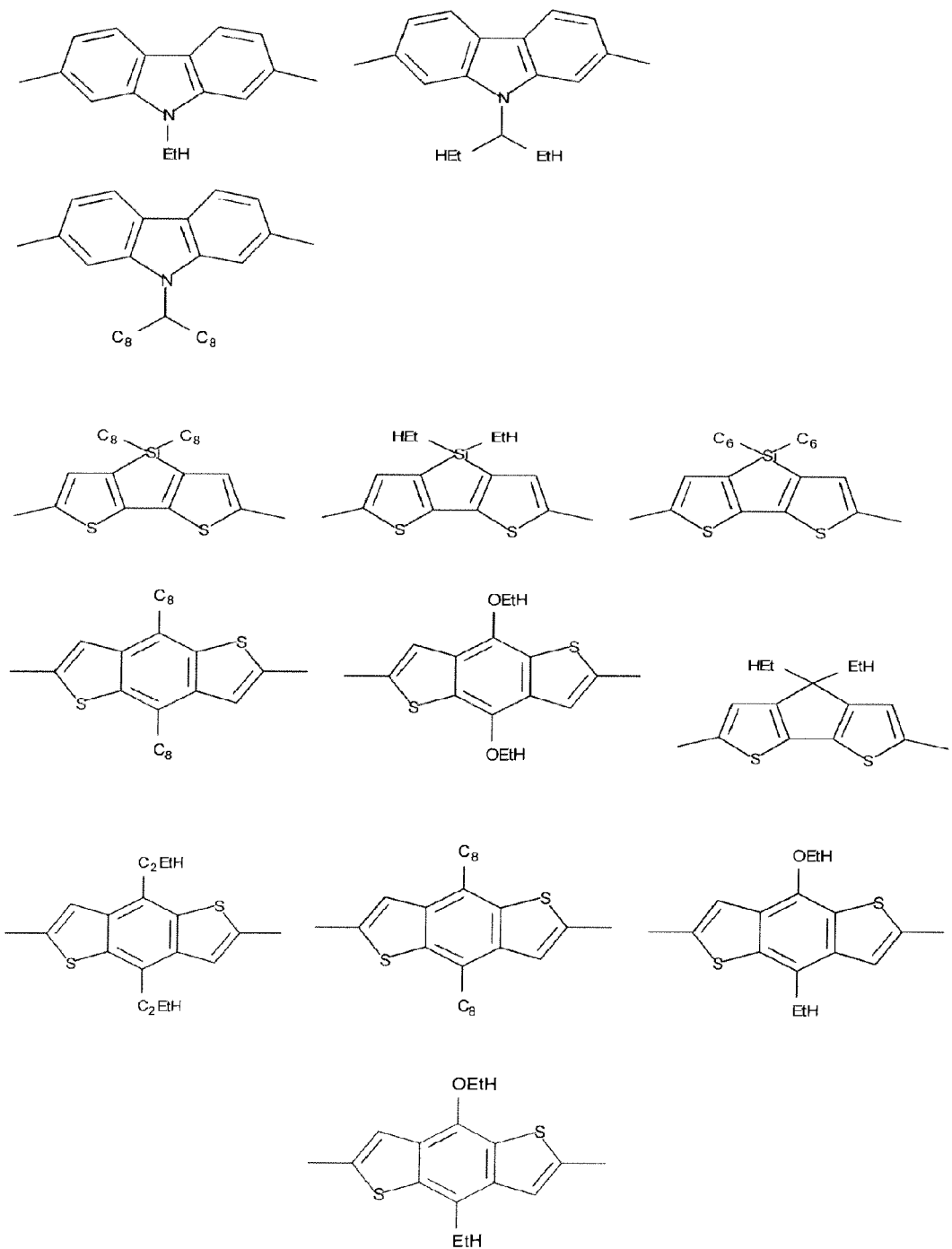
FIGS. 1A-1F provide a listing of exemplary donor moieties, useful for monomers and polymers. The side groups can be adjusted to provide, for example, desired electronic, steric, and reactivity effects.
Figure 1B:
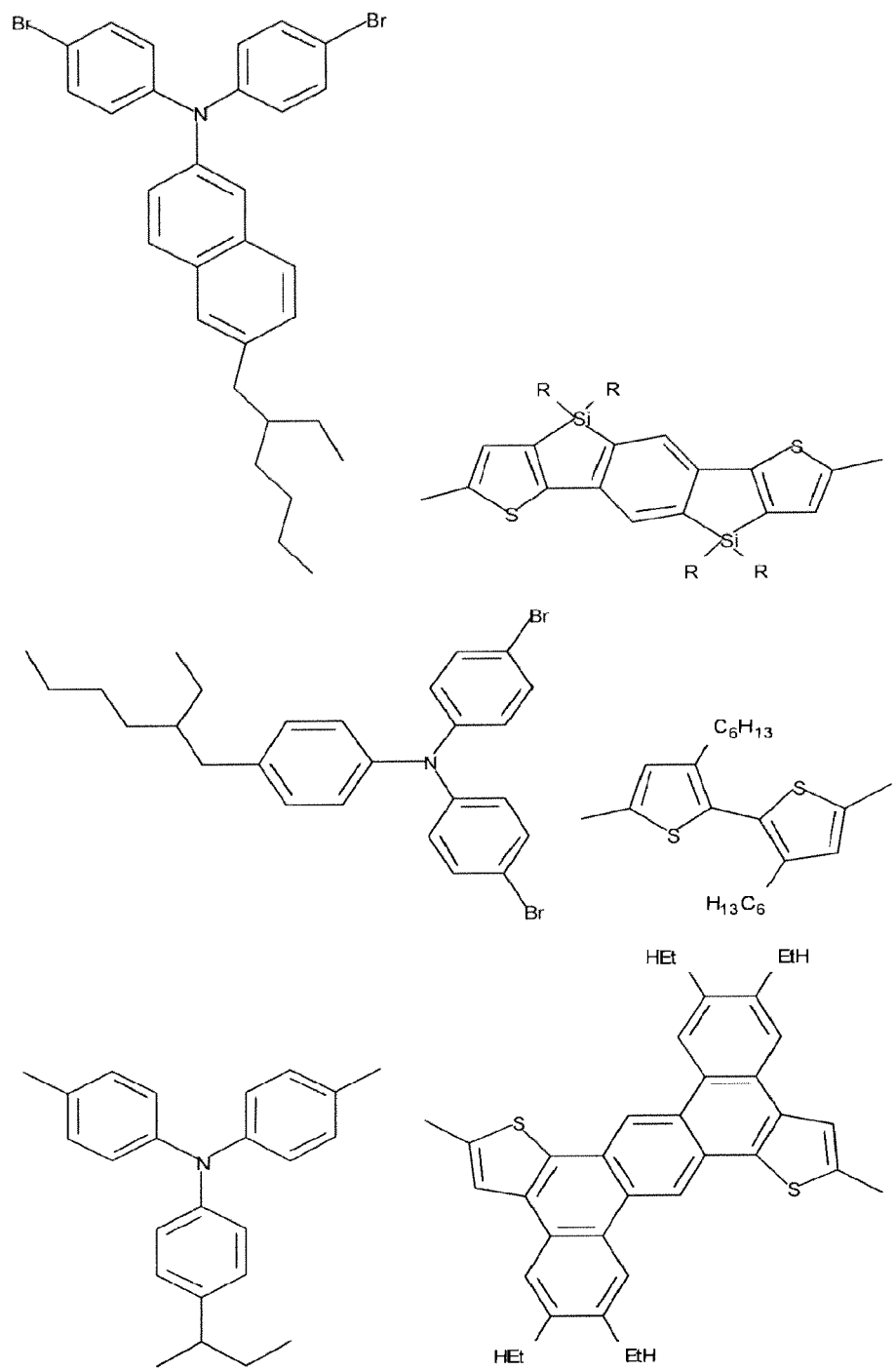
Figure 1C:
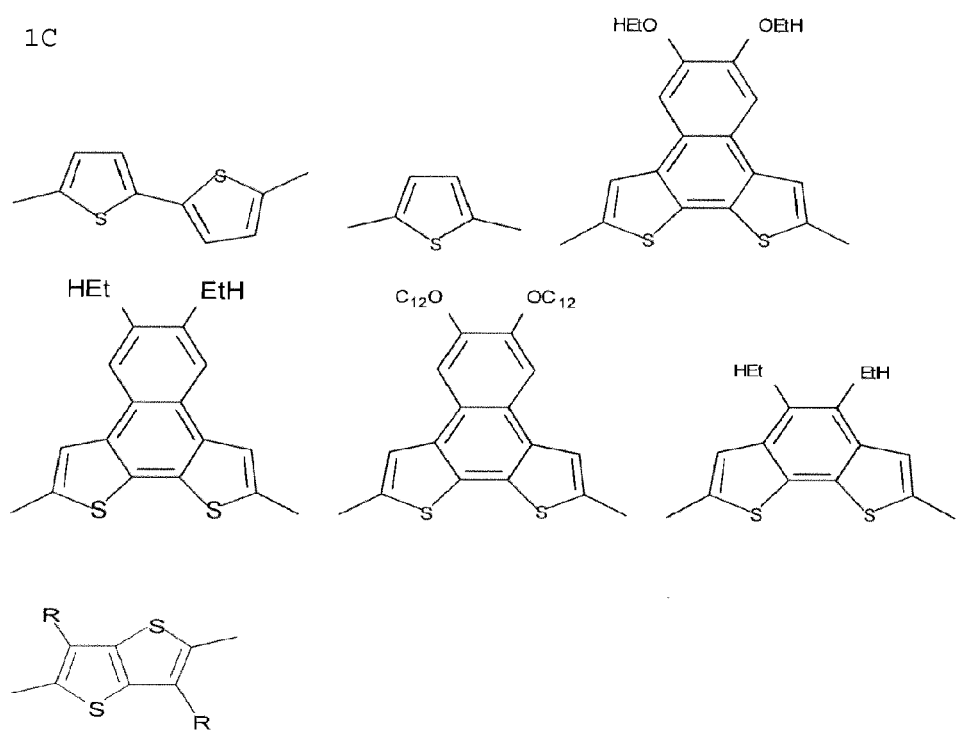
Figure 1D:
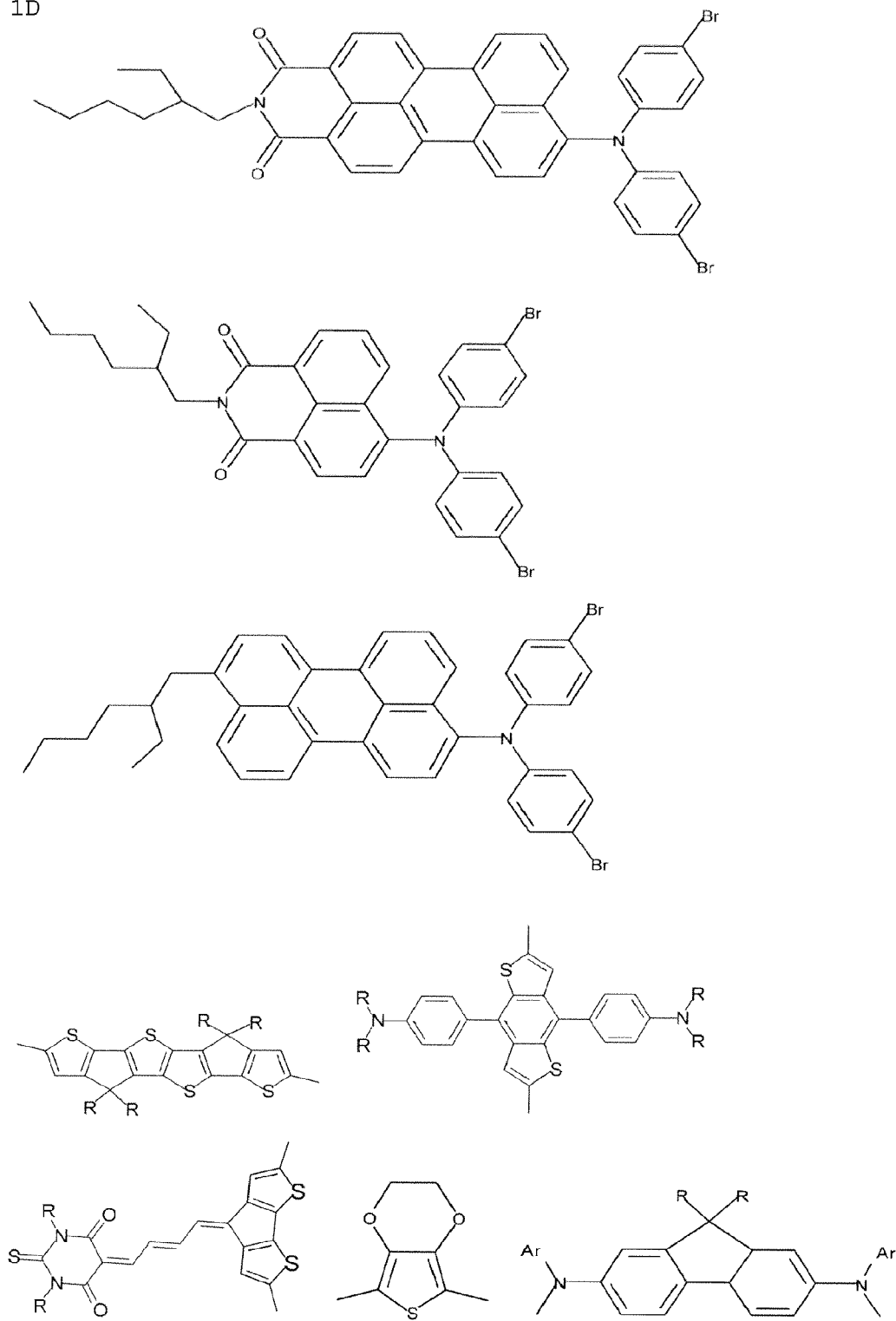
Figure 1E:
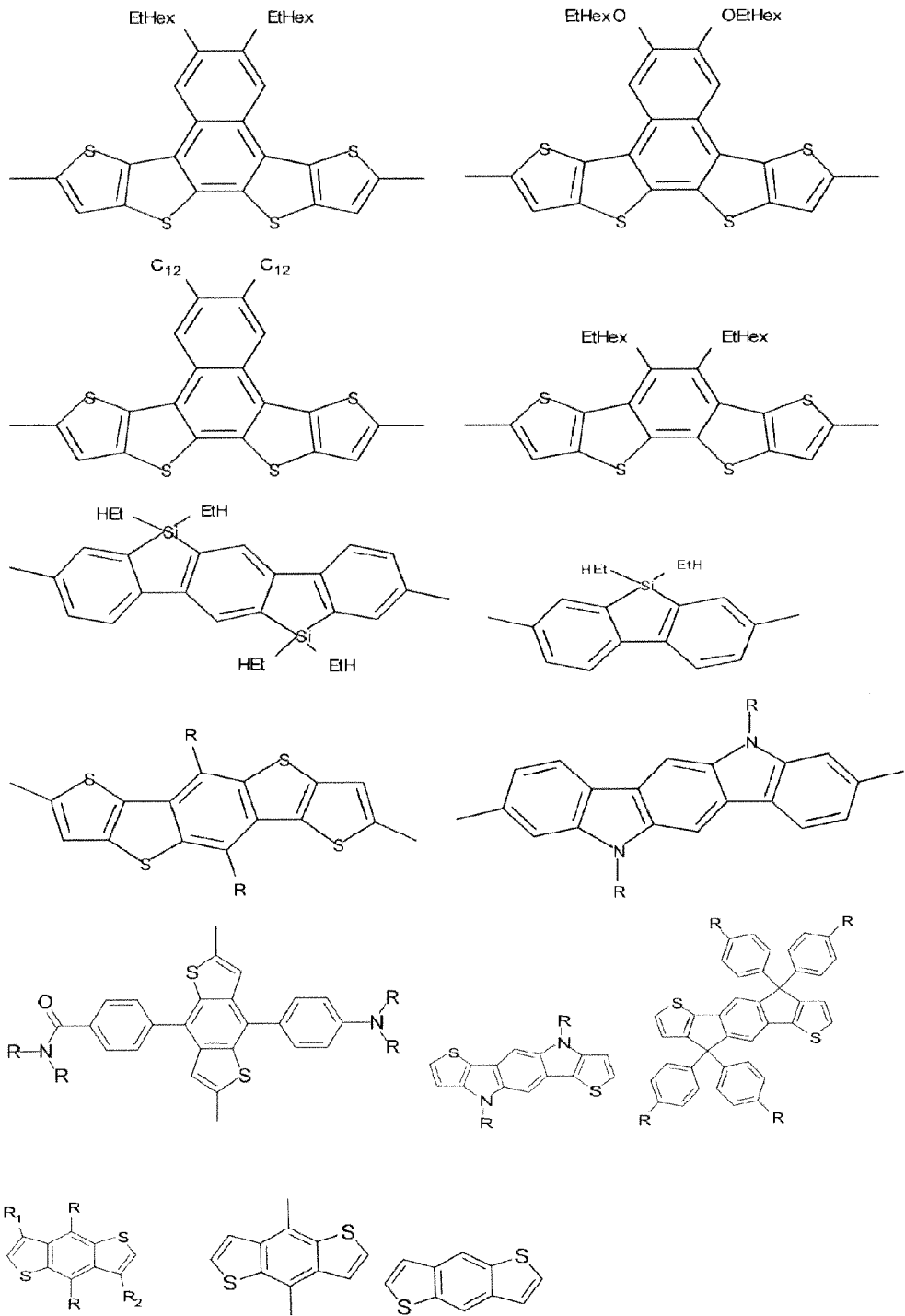
Figure 1F:
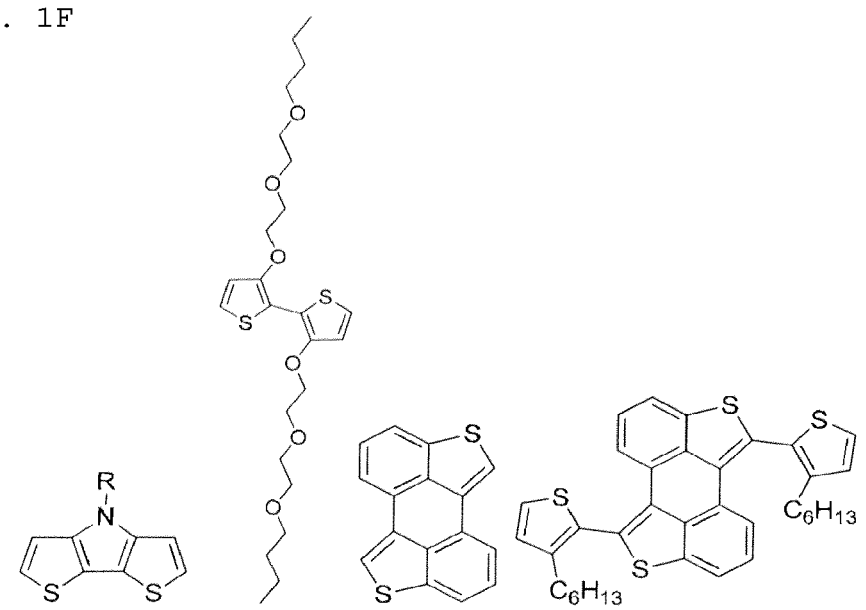

U.S. cofiled application Ser. No. 12/874,163 filed Sep. 1, 2010, assigned to Plextronics, Sheina et al., which is hereby incorporated by reference ("Organic Electronic Devices and Polymers, including Photovoltaic Cells and Diketone-Based Polymers") is hereby incorporated by reference.

U.S. provisional application Ser. Nos. 61/240,137 filed Sep. 4, 2009; 61/241,813 filed Sep. 11, 2009; 61/248,335 filed Oct. 2, 2009; 61/289,314 filed Dec. 22, 2009; 61/290,844 filed Dec. 29, 2009; and 61/307,387 filed Feb. 23, 2010 are each hereby incorporated by reference in its entirety.

All references cited herein are incorporated by reference in their entirety.

No admission is made that any reference cited in this application is prior art.

Compositions comprising at least one conjugated copolymer, wherein the copolymer backbone comprises at least one donor moiety and at least one acceptor moiety, and wherein the copolymer has at least two high extinction coefficient chromophores thereby covering the high photon flux portion of the solar spectrum which is from about 400-1000 nm and centered at about 750-800 nm. Broad absorption is desired including up to the near-infrared region. Vibronic structure can be detected.

Low band gap materials are known in the art. See, for example, Blouin et al., *Accounts of Chemical Research*, 1110-1119, September 2008, 41, 9.

Polymer solar cells are known in the art. See, for example, Chen et al., *Advanced Materials*, 2009, 21, 1-16; Hoppe, *Adv. Polym. Sci.*, 2008, 214, 1-86; Gunes et al., *Chem. Rev.*, 2007, 107, 1324-1338.

Organic semiconductors including arylamines and TPD are known in the art. See, for example, Walzer et al., *Chem. Rev.*, 2007, 107, 1233-1271.

Polymers used in active layers for solar cells are known in the art. See, for example, PCT/US2009/034157 filed Feb. 13, 2009 to Sheina et al. and U.S. provisional application 61/222,053 filed Jun. 30, 2009 (both assigned to Plextronics, Inc.).

PART I: POLYMERS

Part IA:

Polymers and Conjugated Polymers and Copolymers

Polymers can comprise a backbone and side groups as known in the art. See, for example, Billmeyer, *Textbook of Polymer Science*, 1984. Copolymers are known in the art and comprise, for example, terpolymers and block copolymers, as well as alternating and random copolymers. Polymer blends can be prepared.

Conjugated polymers are described in, for example, T. A. Skotheim, *Handbook of Conducting Polymers*, $3^{rd}$ Ed. (two vol), 2007; Meijer et al., *Materials Science and Engineering*, 32 (2001), 1-40; and Kim, *Pure Appl. Chem.*, 74, 11, 2031-2044, 2002.

Conjugated polymers can be used in photovoltaic active layers as a p-type material. The p-type active material can comprise a member of a family of similar polymers which have a common polymer backbone but are different in the derivatized side groups to tailor the properties of the polymer.

Conjugated polymers can comprise planarized backbone and increasing conjugation length before conjugation is interrupted.

Polymers Based on Structure (I)

Polymers can be prepared which comprise a backbone moiety represented by (I):

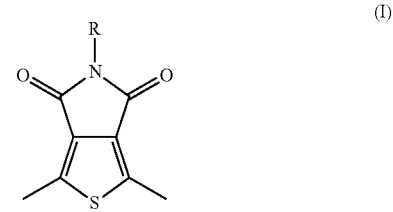

In (I), the lines at the 2- and 5-position of the thiophene ring show where the attachment occurs to another moiety such as a polymer chain or a reactive group for polymerization or coupling.

An important aspect of polymers which comprise (I) is that they are sufficiently soluble so that inks can be formed and solution processing can be achieved. Solubility can be examined in organic or aqueous solvents. One skilled in the art can adapt the R group and other parts of the polymer chain and side groups, as well as molecular weight, to generate sufficient solubility. Organic solvents can be, for example, halogenated and non-halogenated solvents. The solvent can be a single solvent or a mixture of solvents. An example of halogenated solvent in ortho-dichlorobenzene, and this solvent can be used to measure solubility. Solubility can be measured at 25° C. Solubility can be, for example, at least 1 mg/ml, or at least 20 mg/ml. In some embodiments, solubility can be adapted to provide good bulk heterojunction (BHJ) layer morphology. For example, in some embodiments, if the solubility is high when molecular weight is too low, BHJ formation could be compromised. Higher molecular weight may be preferred to modulate solubility, and molecular weight can be used with other formulation strategies including additives to modulate solubility. In addition, polymers can be both soluble and also functionally dispersible in a solvent so that solution processing can be achieved, whether or not a true solution is formed.

The R group can be adapted to facilitate or provide solubility. The R group can also be adapted to provide desired electronic properties. The R group can be also adapted to provide steric and molecular stacking properties.

The atom in the R group bonding to the polymer chain can be, for example, carbon. The carbon can be $sp^3$, $sp^2$, or sp hybridized.

For example, the R group can be optionally substituted alkyl, optionally substituted linear alkyl, optionally substituted branched alkyl, optionally substituted cycloalkyl, optionally substituted aryl, optionally substituted alkylaryl, optionally substituted arylalkyl, optionally substituted alkoxy, or optionally substituted aryloxy. The R group can have, for example, 3-30 carbons, or 4-25 carbons, or 5-15 carbons. Examples include butyl, octyl and dodecyl, as well as ethylhexyl. The R group can comprise at least one, or at least two, or at least three rings, including, for example, five or six membered rings, including for example a pentacene ring or a benzene ring. Different R groups can be used in the same polymer as needed. The R group can be chiral. The R group can be functionalized or substituted as desired. Examples of substituents include amino, carboxylic acid, ester, halogen (including fluoro and chloro), pseudohalogen (e.g., cyano), and other functional groups known in the art.

The R group can comprise a heteroatom such as oxygen or nitrogen in the carbon chain (e.g., ether or amino linkages, respectively). The R group can comprise C1-C20 alkoxy, or C1-C20 alkyleneoxy, for example. The R group can be an oligoether such as, for example, alkoxyalkoxy or alkoxyalkoxyalkoxy, such as, for example, methoxyethoxyethoxy.

The polymer comprising structure I can be free of protecting groups, and in particular the R group can be free of protecting groups.

The R group can be adapted to modulate or tune the LUMO, including provide a decreasing or increasing LUMO, or provide better solid state packing, or provide improved charge transport, and/or provide environmental stability. For example, the R group can be halogenated including comprise a group comprising chlorine or fluorine. The R group can be, for example, perfluorinated. The R group can be, for example, a perfluoroalkyl group such as, for example, $-C_3F_7$. The R group can be, for example, a perfluoroaryl group such as, for example, $-C_6F_5$. For use of halogenated substituent groups to modulate LUMO and solid state packing, see, for example, Schmidt et al., *J. Am. Chem. Soc.*, 2009, 131, 6215-6228.

The R group in one or more polymers can be varied, and different R groups can be used such as, for example, R1, R2, R3, or R', R'', R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Oligomeric and polymeric structures comprising (I) are known in the art. See, for example, Nielsen et al., *Organic Letters,* 2004, 6, 19, 3381-3384 (describing dioxopyrrolo-functionalized polythiophene); Zhang et al., *J. Am. Chem. Soc.,* 120, 22, Jun. 10, 1998 (structures 12 and 21); Zhang et al., *J. Am. Chem. Soc.,* 1997, 119, 5065-5066.

Other references, including theoretical considerations, include Li et al., *Polymeric Materials Science and Engineering (PMSE) Preprints,* 2007, 96, 757-758; Pomerantz et al., *Synthetic Metals,* 2003, 135-136, 257-258; Pomerantz et al., *Tetrahedron Letters,* 2003, 44(8), 1563-1565; and Pomerantz et al., *Tetrahedron Letters,* 40, 1999, 3317-3320.

Polymer comprising (I) can be a random copolymer or a regular alternating copolymer. Polymer can comprise multiple repeat moieties.

Moieties in the polymer chain can provide for carbon-carbon bonding with conjugation, or in addition, can provide hole transport.

Polymer side groups can provide electron withdrawing or electron accepting character, and the strength of this can be varied, e.g, weak or strong, or from weak to strong. Push-pull electronic effects can be produced.

Polymer side groups can be protected or deprotected. For example, butyloxycarbonyl (BOC) can be used to protect amino side groups. However, an embodiment comprises the polymer being totally free of protecting groups.

Block copolymers can be prepared. Either all blocks can be embodiments as described herein, or only a subset of block(s) can be embodiments described herein. For example, a block copolymer could comprise both a conjugated polymer block and a non-conjugated polymer block, or both a donor-acceptor block, and a non-donor-acceptor block.

In one embodiment, the polymer comprises a molecular weight Mn of at least 6,000 g/mol, or of at least 7,500 g/mol, or at least 10,000. In another embodiment, the polymer comprises a molecular weight Mn of at least 20,000, or at least 30,000, or at least 40,000, or at least 50,000.

In another embodiment, the polymer comprises a donor-acceptor structure comprising at least two acceptors, wherein at least one acceptor is represented by structure I and at least one acceptor is represented by structure VII (below).

In another embodiment, the polymer comprises a donor-acceptor structure, and the donor comprises at least one tricyclic unit comprising three fused rings. For example, in one embodiment, the donor comprises a tricyclic ring structure represented by A-B-C, wherein A and C are thiophene rings fused to a central ring B which, optionally, can comprise a heteroatom. The central ring B can be, for example, a five- or six-membered ring. An example of a heteroatom is silicon.

In another embodiment, the polymer comprises a donor-acceptor structure, and the donor comprises at least one tricyclic unit comprising three fused rings, wherein two of the rings are thiophene rings and one of the rings is a benzene ring. In another embodiment, the polymer comprises a donor-acceptor structure, and the donor comprises at least one tricyclic unit comprising three fused rings, wherein two of the rings are thiophene rings and one of the rings is a benzene ring, and the benzene ring is in the middle of the three ring structure. In another embodiment, the polymer comprises a donor-acceptor structure, and the donor is a symmetrical moiety. In another embodiment, the polymer comprises a donor-acceptor structure, and the donor comprises at least one tricyclic unit comprising three fused rings, wherein two of the rings are thiophene rings and one of the rings is a benzene ring.

In another embodiment, the polymer is free of protecting groups for both the donor and acceptor.

The polymer can exhibit vibronic structure as measured by UV-vis absorption spectroscopy.

The structure I, including the R group, can be adapted so the molecular weight is less than, for example, 1,000 g/mole, or even less than 500 g/mole.

Additional polymeric structures comprising (I) are described herein.

In one embodiment, structure I is directly, covalently linked through the thiophene to at least one fused ring system, or at least two fused ring systems. Examples of fused ring systems are shown throughout this application including, for example, donor moieties in FIG. 1. In one embodiment, structure I is not directly, covalently linked through the thiophene to an unfused thiophene ring or an unfused benzene ring.

Donor-Acceptor Polymers

An important embodiment is the donor-acceptor polymer, which is known in the art. See, for example, Zhang et al., *J. Am. Chem. Soc.*, 1995, 117, 4437-4447; Sun and Saraciftci (Eds.), *Organic Photovoltaics, Mechanisms, Materials, and Devices*, CRC, 2005. The structure (I) can be found in acceptor structures of the donor-acceptor polymer.

Donor-acceptor structures can be alternating or random as known in the art and as determined by the polymer synthesis. For example, an alternating structure can be represented as -(D-A)$_n$- (D-A regular alternating donor-acceptor repeating units) and a random structure can be -(D$_x$A$_y$)- (wherein D and A are randomly dispersed). Segmented copolymers can be made wherein donor and acceptor units are included in dimers, trimers, oligomers, and these dimers, trimers, and oligomers are subjected to further polymerization.

The donor-acceptor structure can be tuned and adapted to provide lower band gaps and/or better absorption properties. For example, the donor and the acceptor energy levels, e.g., HOMO and LUMO, can be tuned. Use of different donors and acceptors with different HOMOs and LUMOs can be used in the same polymer. The donor can have HOMO of, for example, 5.1-5.4, or 5.2-5.3. The polymer structure can be adapted to provide deeper HOMO.

Polymer structure can be adapted to provide for small singlet/triplet splitting including, for example, use of rigid chromophores which can minimize loss pathways.

The donor-acceptor structure can comprise one or more dye structures, and the dye structure can be in the backbone or side group.

The structures can be adapted to provide low and multiple band gaps. Examples of band gaps include those less than 2 eV including about 1.4 to about 1.9 eV, or about 1.4 eV to about 1.8 eV. Low band gaps can be associated with high current potential.

Structures can be adapted to avoid recombination sites by, for example, avoiding same LUMOs of the p-type and n-type.

Structures can be adapted to provide ordered assembly. Flat, aromatic-like structures can be used.

Material and/or structural purity can be achieved or improved by use of, for example, crystalline synthetic intermediates.

Molecular weight of the polymer can be, for example, about 10,000 to about 1,000,000, or about 25,000 to about 500,000, or about 25,000 to about 100,000, or about 25,000 to about 40,000 (number average molecular weight, Mn). Polydispersity can be, for example, about 1.5 to about 4.0, or about 1.5 to about 3.0, or about 2.0 to about 2.8.

Model spectra can be used to design polymer structures.

Polymer film absorption profiles can be used to compute photovoltaic cell efficiencies.

Materials can be prepared which provide absorptions on the order of $10^5$ cm$^{-1}$ Absorption can be balanced between red and blue regions of absorption spectrum.

Use of spacer groups can be minimized or avoided to alter or reduce the dihedral angle of rotation between adjacent rings.

Planarizing non-covalent binding interactions between donor-donor and/or donor-acceptor, and/or acceptor-acceptor can serve to rigidify the chromophore which can help to increase alpha.

Steric interactions between donor and acceptor can be minimized.

Kits can be produced comprising at least one donor molecule or monomer and at least one acceptor molecule or monomer.

Additional donor-acceptor structures are described herein.

Moieties IIA and IIB

As part of a larger molecule, including a polymer for example, the structure I can be part of another larger moiety such as, for example, IIA or IIB:

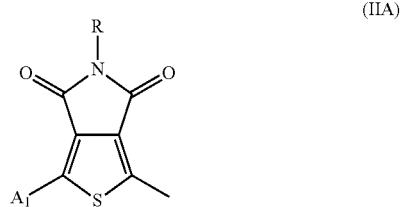

(IIA)

wherein A1 comprises a thiophene ring linked to (I) at the two or five position of the thiophene ring; and

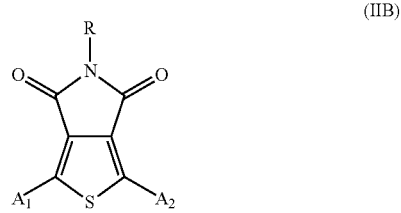

(IIB)

wherein both A1 and A2 comprise thiophene ring linked to (I) at the two or five position of the thiophene ring.

Structures IIA and IIB can be incorporated into the polymer backbone via the A1 and A2 groups. Structures A1 and A2 can be part of a donor moiety, for example. For example, the donor moiety benzodithiophene comprises two thiophene rings, either of which can be an A1 or an A2.

Here, A1 can comprise a thiophene ring linked to (I) at the two or five position of the illustrated thiophene ring. Similarly, A2 (and both A1 and A2) also can comprise a thiophene ring linked to (I) at the two or five position of the illustrated thiophene ring. The thiophene ring in A1 and A2 can either be a single thiophene ring, an oligomer series of two, three, or more thiophene rings bivalently linked, or a thiophene ring which is part of a larger fused ring structure. For example, A1 and/or A2 can be represented by -TT- or -TTT- or -TTTT- wherein T is a thiophene ring linked at the 2 and 5 position of the thiophene ring.

Thiophene rings can be optionally substituted at the 3- and/or 4-positions to facilitate solubility as known in the art including use of optionally substituted alkyl, oligoether, polyether, ester, ketone, or alkyleneoxy substituents including n-alkyl such as C6-C8 or branched alkyl (e.g., hexyl, ethylhexyl, or methoxyethoxyethoxy substituents).

Intramolecular Non-Covalent Interactions Including Carbonyl Interaction with Thiophene Sulfur A variety of intramolecular non-covalent interactions such as electrostatic, coulombic, hydrogen bonding or chelates can be used to provide increased rigidity and/or planarity to the polymer chain and its chromophores, although various embodiments described herein are not necessarily limited by theory. Increased rigidity can be used to increase the likelihood for a well behaved excited state and lead to good excitonic diffusion distances and minimization of energy loss pathways from excited state (e.g., charge trapping, polaronic quenching, excited state deactivation, or even localization). Absorption profiling can be used to examine such features.

In particular, while various embodiments described herein are not necessarily limited by theory, it is believed that for at least some embodiments, when a thiophene ring is covalently linked to (I), as shown in IIA or IIB for example, the carbonyl groups can interact with thiophene sulfur. The carbonyl oxygen is negatively charged compared to the thiophene sulfur which is relatively positively charged. This can provide planarization and/or increase rigidity in the backbone and improve performance. The interactions can be measured by methods known in the art including, for example, x-ray or NOE (Nuclear Overhauser Effect).

See, for example, Pomerantz et al., *Synthetic Metals,* 2003, 135-136, 257-258; Pomerantz et al., *Tetrahedron Letters,* 2003, 44(8), 1563-1565; and Pomerantz et al., *Tetrahedron Letters,* 40, 1999, 3317-3320.

In addition to carbonyl oxygen:sulfur interaction, other electrostatic or coordination bonding interactions can be used to help planarize, bridge, rigidify and thus, control moiety dihedral angles providing advantaged chemico-physical properties (e.g., photophysics and electrical). For example, sp$^2$ nitrogen and etheral oxygen can be used. Other examples include pyridine, imidazole, ketone, ether, lactone, lactam, and amidine. One particularly useful monomeric unit for the polymer backbone is a thiophene ring which is substituted at the 3- and 4-positions by a bridging dialkoxyalkylene motif such as, for example, —OR—O wherein R is an alkylene moiety, such as —OCH$_2$CH$_2$O— (commonly known as EDOT).

Donor-Acceptor polymers comprising diketo types of structures, such as dioxypyrrolo-functionality, can provide intramolecular interactions as a "design rule" for the synthesis of new materials for application in organic electronics, such as OPVs, achieving record performances. See also FIG. 3 below.

The thiophene ring can be part of an isolated thiophene moiety or a fused ring thiophene moiety such as the thiophene found in benzodithiophene.

Vibronic Structure

The polymers described herein can exhibit vibronic structure as shown in, for example, UV-vis absorption spectroscopy. Vibronic structure in a p-type chromophore can be an indication of an organized and rigid structure. This can provide a more well-behaved excited state behavior and exciton diffusion length. Vibronic structure can be found in the film state or solution state. In particular, for example, the ratio of a first peak (0-0 transition) to second peak (0-1 transition) can be higher than 1.

Vibronic features and vibronic structure can be present. Vibronic structure is described in, for example, *Handbook of Conducting Polymers,* Skotheim, T. A., *Handbook of Conducting Polymers*; Marcel Dekker: New York, 1986, including Chapter 9 (McCullough et al.), Chapter 14 (Scherf), and Chapter 28 (Del Zoppo et al.). See also, Brown et al., *Phys. Rev. B,* 67, 064203 (2003).

Vibronic structure and features can be examined experimentally and theoretically by methods known in the art.

Particular Polymer Structures

Particular polymer structures comprising (I) together with a variety of donors and acceptors are shown in IIIA-K.

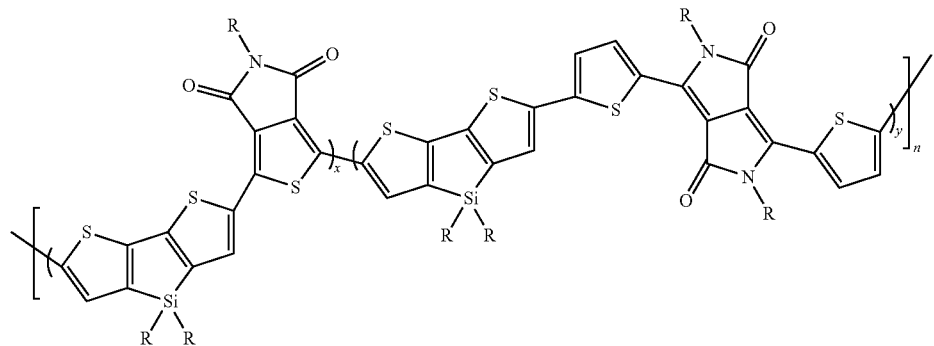

(III-A)

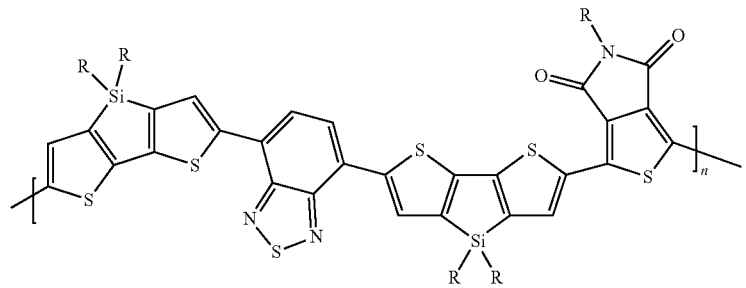

(III-B)

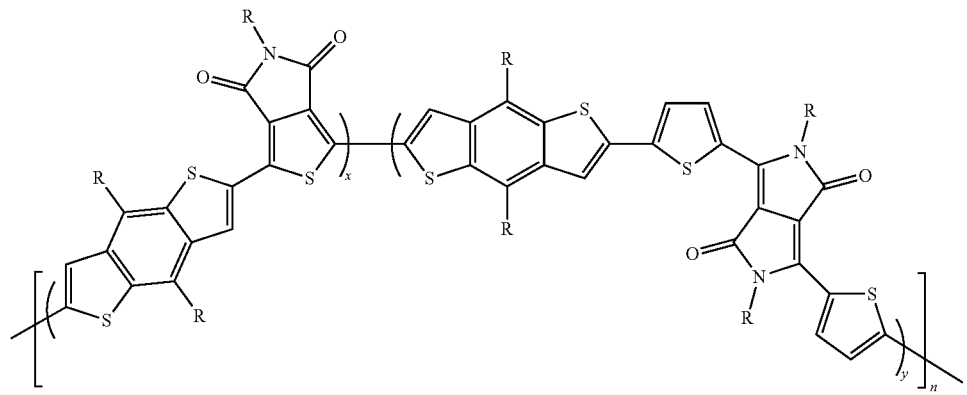
(III-C)
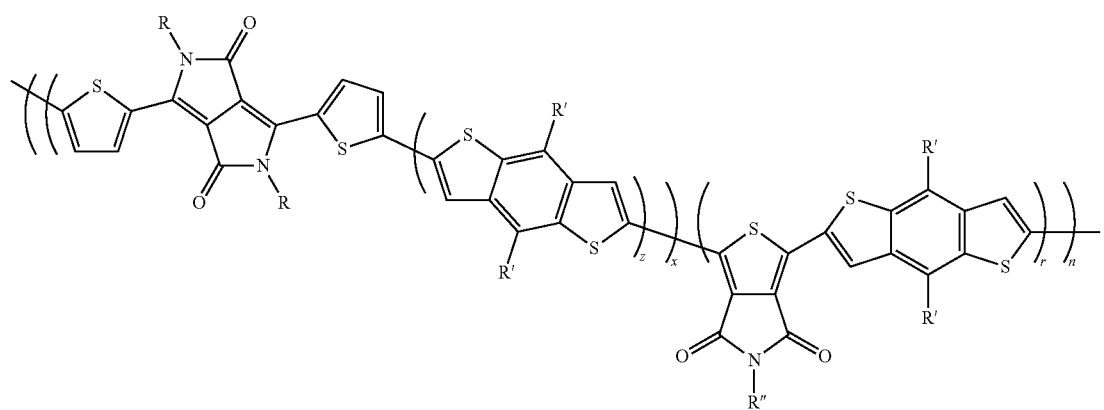
(III-D)
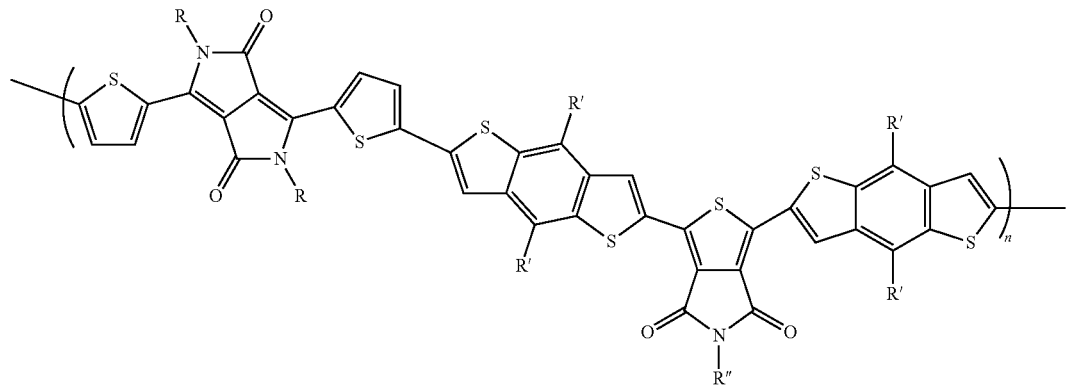
(III-E)
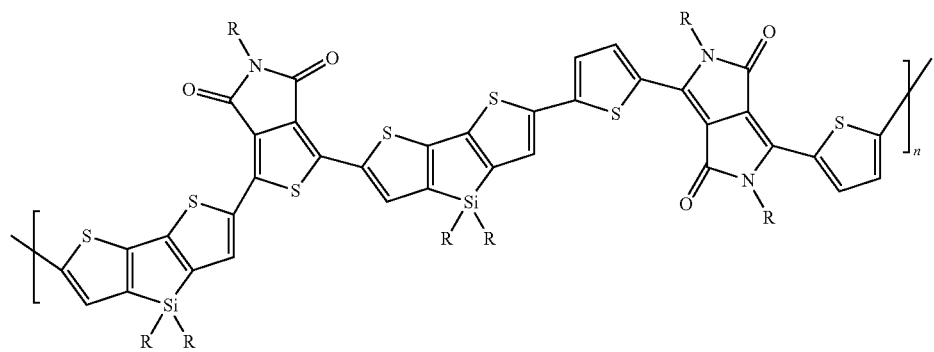
(III-F)

-continued

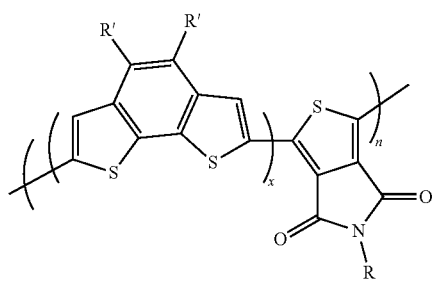
(III-G)

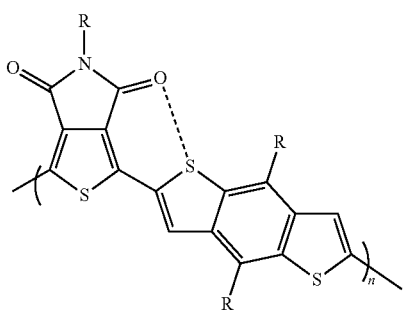
(III-H)

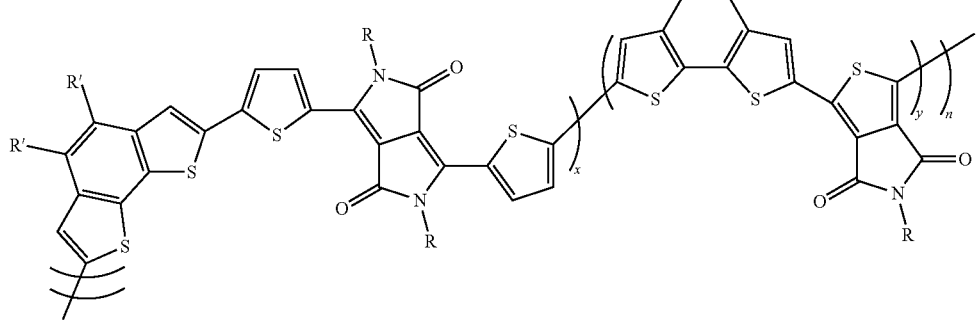
(III-I)

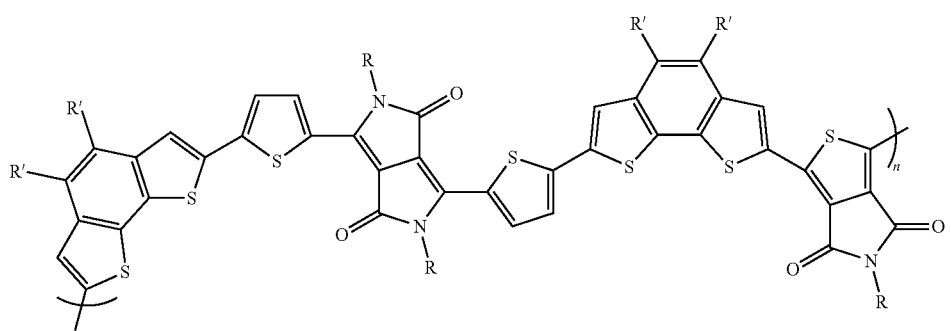
(III-J)

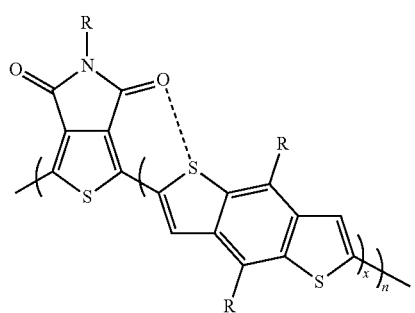
(III-K)

In structures III, the variables such as n, x, and y can be greater than one and less than an integer, and can be adapted as known in the art and as described in the specification, figures, claims, and working examples herein for coupling to form dimers, trimers, oligomers, and polymers. Molecular weight, as well as reaction stoichiometry and order of mixing, can be used to determine these variables n, x, and y. In some structures, the structures may represent statistical representations of polymer materials as known to those skilled in the art.

Donors and Other Acceptors

Other donors, or donor moieties, are known in the art. FIG. 1 illustrates an exemplary listing of donor structures which can be used. The structures shown in FIG. 1 can be used in monomers, dimers, trimers, oligomers, and polymers. The side group can be varied and is not limited by shown structure in FIG. 1. See, for example, description of R above for types of side groups which can be used in the structures of (I). In FIG. 1, the representation of dangling bonds in—drawn off of a ring as a substituent means, as known in the art, a linkage site for a reactive group, or a linkage site for linking into another moiety like a dimer, trimer, oligomer, or polymer. Two of these sites means the moiety can be bivalently linked to another moiety including a polymer chain.

Symmetrical donor structures can be used. For example, a central ring can be fused on each side with a ring to provide a symmetrical three fused ring structure. The central ring can be an all carbon ring or a ring comprising at least one heteroatom. In one embodiment, benzodithiophene units can be used as donor. A particularly useful donor is that shown in Example 9 below. See, for example, Liang et al., *J. Am. Chem. Soc.*, 2009, 131, 56-57; see also *J. Am. Chem. Soc.*, 131, 7792, 2009, ("Highly Efficient Solar Cell Polymers Developed via Fine-Tuning of Structural and Electronic Properties."). See also, Hou et al., *Macromolecules*, 2008, 41, 6012-6018. In addition, the dithienosilole moiety can be used. See, for example, Example 2. In one embodiment, tricyclo units can be used including those that comprise a central ring fused to two other thiophene rings. Another example is shown as a derivative of structure VIII, wherein the donor comprises three rings linked together (thiophene-pyrrole-thiophene):

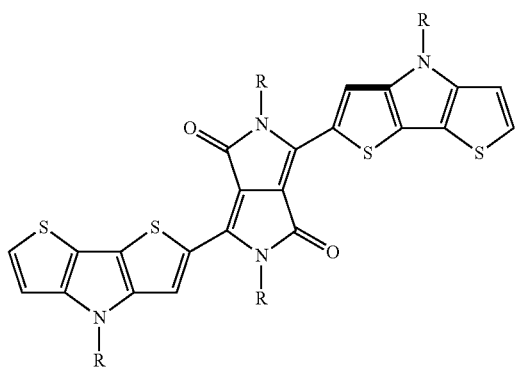

Figure 2:
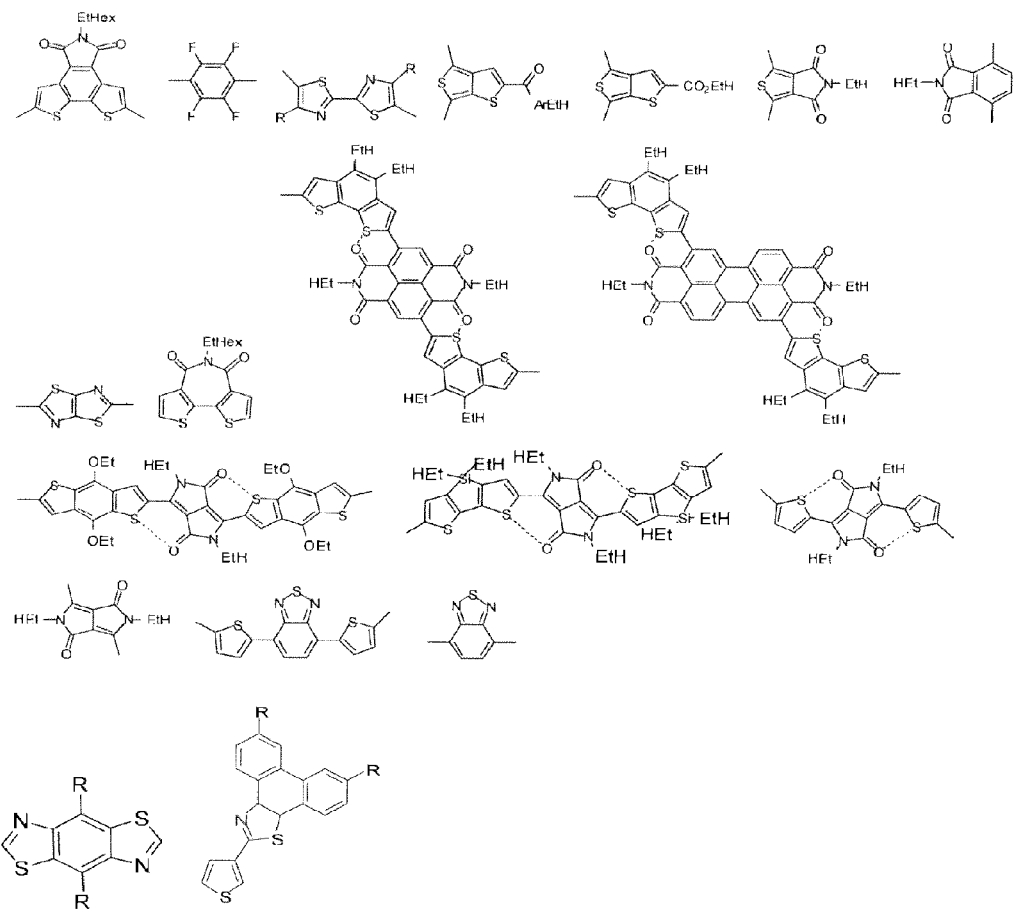
FIG. 2 provides a listing of exemplary acceptor moieties, useful for monomers and polymers. The side groups can be adjusted to provide, for example, desired electronic, steric, and reactivity effects.

In addition, other acceptors, or acceptor moieties, can be used with the structure (I). Examples include those shown in FIG. 2. The structures shown in FIG. 2 can be used in monomers, dimers, trimers, oligomers, and polymers. The side group can be varied and is not limited by shown structure in FIG. 2. See, for example, description of R above for types of side groups which can be used in the structures of (I). In FIG. 2, the representation of —R or R— means a linkage site for a reactive group, or a linkage site for, after reaction, linking into another moiety like a dimer, trimer, oligomer, or polymer. Two of these sites means the moiety can be bivalently linked to another moiety including a polymer chain.

An example of an acceptor is the diketopyrroleopyrrole-based acceptor moiety. See, for example, Zhou et al., *Chemistry of Materials*, 2009, "Synthesis and Photovoltaic Properties of Diketopyrrolopyrrole-Based Donor-Acceptor Complexes." See, for example, working example 9.

For a single polymer, more than one donor can be used: e.g., D1, D2, D3, and the like. In addition, more than one acceptor can be used: e.g., A1, A2, A3, and the like.

Polymers can comprise D1-A1 moieties, D2-A2 moieties, D3-A3 moieties, and the like.

Use of more than one donor or acceptor can provide broader and/or stronger absorption bands and/or vibronic structures.

In particular, an example of a donor structure is found in U.S. provisional application No. 61/222,053 filed Jun. 30, 2009.

Spacer moieties can be used as desired.

Any of the moieties shown in FIGS. 1 and 2 can be called a structure IV.

Embodiments for Copolymer Architecture Based on D1, D2, A1, and A2

The following chart shows different, exemplary embodiments for copolymer architecture with different donors, D1 and D2 donors, and different acceptors, A1 and A2 acceptors. The Chart I shows examples which are different from the -[D-A]- alternating formula seen in the prior art.

Chart I

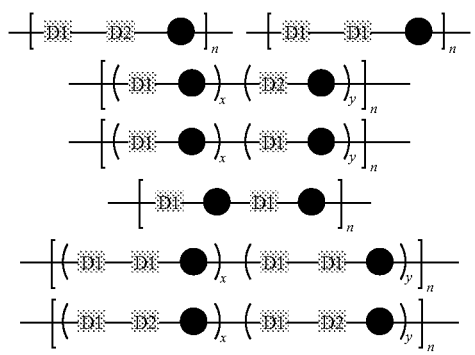

The acceptors, A1, A2, or both can comprise structure I, and can also comprise any of the acceptors listed in FIG. 2.

The donors can be selected from those listed in FIG. 1, for example. The structures shown in Chart I can be extended to further include additional donors, e.g., D3, D4, D5, and the like, or additional acceptors, e.g., A3, A4, A5, or the like.

In some embodiments, the conjugated backbone can comprise non-thiophene units in the chain of carbons subjected to the conjugation. For example, a benzene ring can form part of the conjugation structure via, for example, benzodithiophene units.

Ratio of Donor and Acceptor

The molar ratio of donor and acceptor can be one, less than one, or more than one. In other words, the polymer does not need to comprise equal molar amounts of donor and acceptor. The polymer can comprise more donor than acceptor, or more acceptor than donor. Chart I shows examples of this. For example, the ratio can be 2:1.

Random or Alternating Copolymers

Different copolymer microstructures can be prepared as known to those skilled in the polymer chemistry arts. For example, random copolymer structures can be produced. Mixed monomer polymerization can be carried out. Non-random copolymer structures can be produced.

For the random copolymer embodiment, one can use appropriate synthetic sequence to obtain good materials. Synthetic approaches include, for example, Yamamoto, Suzuki, Negishi or Stille couplings for polymerization. See, for example (a) *Cross-Coupling Reactions: A Practical Guide*, Ed. Miyaura, 2002; (b) *Handbook of Organopalladium Chemistry for Organic Synthesis*, Ed. Negishi, 2002; (c) Kuwano, R, Utsunomiya, M., Hartwig, J. F., *J. Org. Chem.*, 2002, 67, 6479-6486; (d) Yu et al. *J. Am. Chem. Soc.* 2009, 131, 56; (e) Hou, J.; Park; M.-H.; Zhang, S.; Yao, Y.; Chen, L.-M.; Li, J.-H.; Yang, Y. *Macromolecules*, 2008, 41 (16), 6012-6018; (0 Blouin, N.; Michaud, A.; Gendron, D.; Wakim, S.; Blair, E.; Neagu-Plesu, R.; Belletête, M.; Durocher, G.; Tao, Y.; Leclerc, M. *J. Am. Chem. Soc.* 2008 130 (2), 732-742; (g) Swager et al. *Adv. Mater.* 2001, 13, 1775; (h) Koeckelberghs et al. *Macromolecules.* 2007, 40, 4173; (i) High-Efficient-Low-Cost Photovoltaics, Springer Verlag Berlin Heidelberg, 2009, Editors: Petrova-Kock, V.; Goetzberger, A., 195-222.

For example, one embodiment provides:

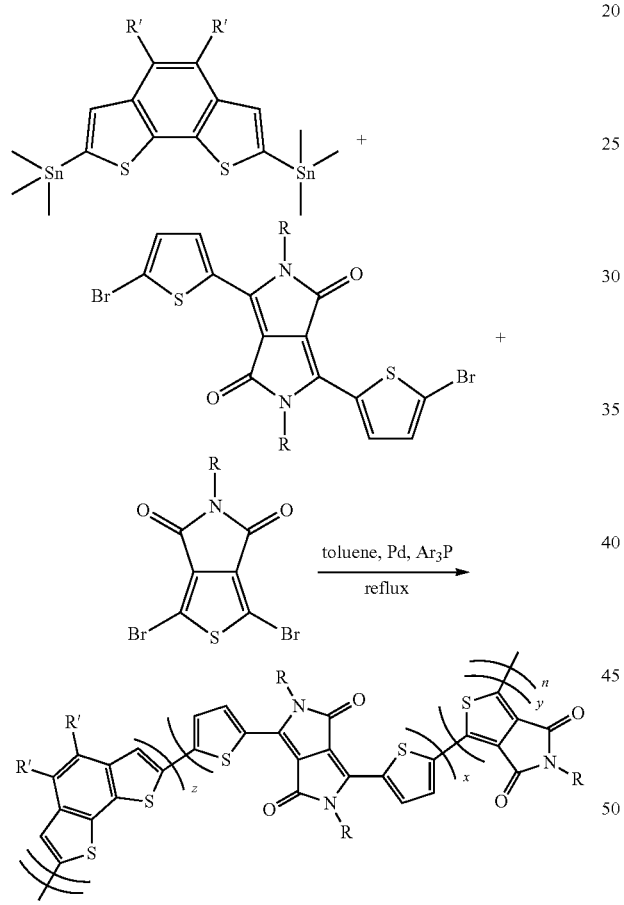

One embodiment provides for preparing high purity intermediates, such as trimers.

Regular alternating copolymer structures can be produced. Chart I shows examples of this.

Polymer Properties/Chromophore/Absorption Spectra

Polymer properties can be adapted to provide the good photovoltaic properties and to follow the design rules noted herein.

Lambda max can be, for example, greater than 600 nm.

Absorption edge can be extended into the red region.

Absorption spectra are important parameters for the polymers, particularly for photovoltaic applications. It is known to record absorption spectra, including UV-vis absorption spectra, for conjugated polymers. See, for example, Brown et al., *Phys. Rev. B,* 67, 064203 (2003) (describing spectra for different kinds of polythiophenes).

Polymers Comprising Structure V

In addition, polymers can be prepared wherein the polymer backbone comprises the moiety (V):

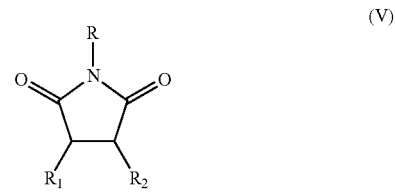

wherein moiety V is linked bivalently to the polymer backbone via the R1 and R2 groups, which can foam a ring. In structure V, the carbon atoms 3 and 4 of the pyrrole ring can be joined by a double bond to form part of an extended conjugated polymer chain, as shown in structure VA:

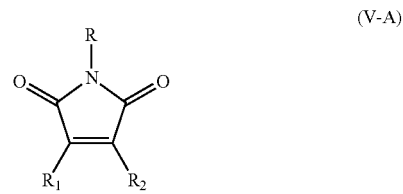

The R1 and R2 groups can link together to form a ring, including for example a five- or six-membered ring including an all-carbon ring or a ring comprising a heteroatom, including a heterocyclic ring, including, for example, a thiophene ring or a benzene ring. The ring formed by R1 and R2 can be aromatic or pseudoaromatic. The ring can be bivalently functionalized so it can be incorporated into the polymer backbone.

Structure I is an embodiment of structures V and V-A. Another example is structure VB:

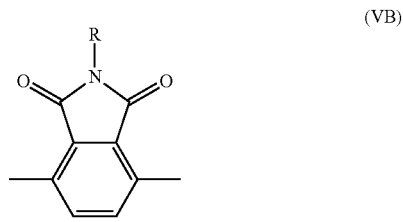

The R groups described herein for (I) can be used in (V) also.

For structure V, as with structure I, the R group in one or more polymers can be varied, and different R groups can be used such as, for example, R1, R2, R3, or R', R", R'", and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Structure V can be used in the analogous manner as Structure I is described herein.

In one embodiment, structure V is directly, covalently linked through the ring, which is formed from the R1 and R2 groups, to at least one fused ring system, or at least two fused ring systems. Examples of fused ring systems are shown throughout this application including, for example, donor moieties in FIG. 1. In one embodiment, structure V is not directly, covalently linked through the ring, which is formed from the R1 and R2 groups, to an unfused thiophene ring or an unfused benzene ring.

Polymers Comprising Structure VI

Polymers can be also prepared which comprise at least one backbone moiety represented by:

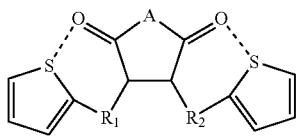

(VI)

wherein A can be an optionally substituted alkylene moiety (e.g., optionally substituted methylene or ethylene, —(CH$_2$)$_x$— or a heteroatom, and wherein the moiety V is bivalently linked to the polymer backbone via the illustrated thiophene rings linked to the R1 and R2 groups. In VI, although a non-covalent interaction is illustrated as a dashed line between the thiophene ring sulfur and the carbonyl oxygen, such interaction is optional and not required. The thiophene rings can be linked to the polymer at their 2- and 5-positions. The thiophene rings can be linked to additional thiophene rings.

As with structure V, in structure VI, the carbon atoms 3 and 4 of the top ring comprising alkylene or heteroatom A can be joined by a double bond to form part of an extended conjugated polymer chain, as shown in structure VI-B:

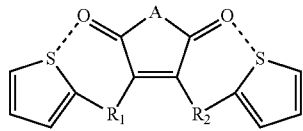

(VI-B)

In the heteroatom embodiment for A, A can be, for example, nitrogen, oxygen, sulfur, or selenium. The nitrogen, if the heteroatom A, can be functionalized as shown in I. The R group in structure I is adapted for bonding to a nitrogen atom. In other structures such as VI, described herein, R can bind to other atoms besides nitrogen, and R can be adapted accordingly.

In a manner similar to structure V, R$_1$ and R$_2$ can form five or six-membered rings, including aromatic or pseudoaromatic rings, including heterocyclic rings, including benzene ring or thiophene ring.

Aromatic rings structures including aromatic rings structures, including benzidine ring structures, and biphenyl structures, can be used.

Structures I, II, and V can be embodiments of structure VI.

As with Structures I and V, the R groups in structures VI (R1 and R2) in one or more polymers can be varied, and different R groups can be used such as, for example, R1, R2, R3, or R', R'', R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

In one embodiment, the illustrated thiophene rings in structure VI are part of at least one fused ring system, or at least two fused ring systems. Examples of fused ring systems are shown throughout this application including, for example, donor moieties in FIG. 1. In one embodiment, the illustrated thiophene rings in structure VI are not unfused thiophene rings.

Polymers Comprising Structure VII

Polymers can be also prepared wherein the backbone comprises a structure represented by VII:

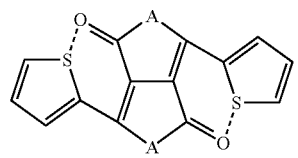

(VII)

Here, A can be an optionally substituted alkylene or heteroatom such as, for example, N, O, S, or Se, as described above for structure VI. The A group can comprise substituents such as the R group in structure I. For example, the R group in structure VII can be adapted for bonding to a nitrogen atom. In structures such as VII described herein, R can bind to other atoms besides nitrogen, and R can be adapted accordingly.

The structure VII can be linked into the polymer chain via the illustrated thiophene rings.

As with Structures I, V, and VI, the R groups in structure VII in one or more polymers can be varied, and different R groups can be used such as, for example, R1, R2, R3, or R', R'', R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

In Part IB below, structure VIII, substructure IX, and other structures in Part IB can be examples of VII and are described further below.

In one embodiment, the illustrated thiophene rings in structure VII are part of at least one fused ring system, or at least two fused ring systems. Examples of fused ring systems are shown throughout this application including, for example, donor moieties in FIG. 1. In one embodiment, the illustrated thiophene rings in structure VII are not unfused thiophene rings.

Methods of Making Monomers and Oligomers

Monomers, or low molecular weight compounds which can be used for further synthesis and polymerization, can be prepared as known in the art including the arts of organic synthesis and polymer chemistry. See, for example, *March's Advanced Organic Chemistry*, 6$^{th}$ Ed., Wiley, 2007; Nielsen, C. B. and Bjørnholm, T. *Org. Lett.*, 2004, V6, 338; Watson et al. *J. Am. Chem. Soc.* 2009 131, 7206-7207.

Examples of monomers include

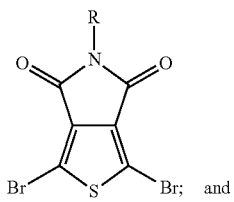

(IA)

and

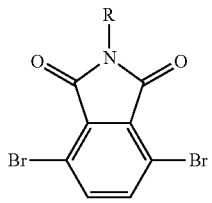

(VB)

For example, thiophene can be brominated at the 3- and 4-positions, and then the bromines converted to acyl chloride at the 3- and 4-positions. The thiophene can then be brominated at the 2- and 5-positions. Then reaction of both acyl-chlorides with a primary amine like n-butyl amine can result in imide formation and closure of the ring to form a structure shown in I with two bromine sites for polymerization. See Zhang et al. *J. Am. Chem. Soc.*, 120, 22, 1998, 5355-5362.

In general, difunctional monomers can be prepared which show donor or acceptor structures: X-D-X wherein a donor moiety D is provided with reactive groups X; or Y-A-Y wherein an acceptor A is provided with reactive groups Y; reactive groups X and Y can be adapted to react with each other and covalently couple the donor and acceptor into a dimer.

Dimers can be made and subsequently adapted as needed and polymerized.

Trimers can be made and subsequently adapted as needed and polymerized. For example, a difunctional unit can be reacted with two mono-functional units to prepare a trimer. Oligomers can be made. Oligomers are known in the art. See, for example, Radke et al. *Organic Letters*, 2005, 7, 23, 5253-5256, which describes Stille coupling.

Methods of Making Polymers

Polymerization reactions are known in the art including, for example, electrochemical or oxidative chemical polymerization, or metal promoted cross-coupling polymerizations, e.g., Yamamoto, Suzuki, Negishi, Horner-Emmons, or Stille coupling ((a) Stille, J. K. *Angew. Chem. Int. Ed. Engl.* 1986, 25, 508. (b) Farina, V. et al. *J. Am. Chem. Soc.* 1991, 113, 9585. (b) Bao, Z. et al. *J. Am. Chem. Soc.* 1995, 117, 12426.), and Yamamoto-type polymerization (Yamamoto, T. et al. *Macromolecules* 1992, 25, 1214.)

Difunctional monomers, dimers, trimers, and/or oligomers can be polymerized as represented by, for example (wherein A and B can couple to provide carbon-carbon bond formation and X and Y are a monomer, dimer, trimer, or the like): A-X-A+B-Y-B→x-Y (end groups not shown)

Part IB: Additional Embodiments Including Diketopyrrolopyrrole-Based Polymers

Diketopyrrolopyrrole-based compounds are known in the art. See, for example, U.S. Pat. No. 4,585,878 (Ciba-Geigy), U.S. Pat. No. 4,778,899 (Ciba-Geigy), U.S. Pat. No. 4,931,566 (Ciba-Geigy), PCT publication WO 2008/000664, and European patent applications EP 0962499A2, EP 0094911B1, EP 0181290 B1, EP 0302018 B1, EP 0672729 B1, and EP 0962499 B2. See, also, Yu Zhu Doctoral Dissertation, University of Koln, 2006. Diketopyrrolopyrrole also can be called DPP, as known in the art.

One embodiment provided herein comprises materials, including an oligomer or a polymer, having a donor-acceptor structure, wherein the donor comprises a fused ring system which is directly and covalently linked to an acceptor structure comprising diketopyrrolopyrrole structure. Particularly embodiments are provided, wherein the fused ring system comprises a fused thiophene ring which is directly, covalently linked to the acceptor structure.

Also provided is a composition comprising an oligomer or a polymer having a donor-acceptor structure, wherein the acceptor comprises a diketopyrrolopyrrole structure which is not directly and covalently linked to a donor structure by an unfused thiophene or an unfused benzene ring.

In addition to embodiments shown above, including structure VII, also provided are low molecular weight, oligomeric, and polymeric materials comprising at least one moiety represented by structure VIII and substructure IX:

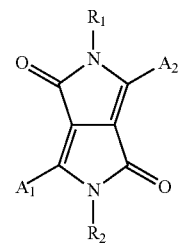

(VIII)

wherein A1 and A2 each independently comprise a fused ring system comprising at least two fused rings directly covalently linked to the substructure of VIII represented as substructure IX:

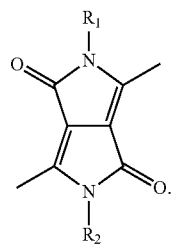

(IX)

A1 and A2 are moieties which form part of the copolymer repeat unit, binding the moiety VIII to a larger polymer backbone, and can comprise a donor moiety, for example.

Another embodiment provides low molecular weight, oligomeric, and polymeric materials comprising at least one moiety represented by:

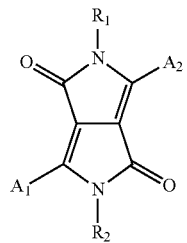

(VIII)

wherein A1 and A2 each independently do not comprise an unfused thiophene or unfused benzene ring directly covalently linked to the substructure of VIII represented as substructure IX:

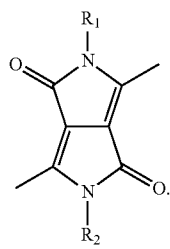

(IX)

Again, A1 and A2 are moieties which form part of the copolymer repeat unit, binding the moiety VIII into a larger polymer backbone, and can comprise a donor moiety, for example.

A1 and A2 can be the same or different. Symmetrical structures can be used or unsymmetrical structures. The following is a moiety which comprises one A1 moiety on the left side which can comprise a fused ring system directly and covalently linked to the substructure IX, or A1 can be adapted so it does not comprise an unfused thiophene or benzene ring:

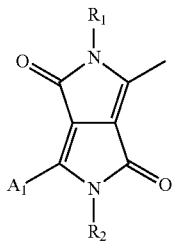

(VIII-C)

However, in VIII-C, the right side dangling bond extending out of the pyrrole ring need not be so limited. Structure VIII-C is an example of an unsymmetrical moiety.

Structure VIII-D through VIII-H below illustrate examples of an unfused thiophene ring which is directly, covalently linked to substructure IX.

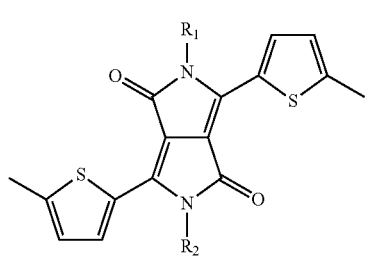

(VIII-D)

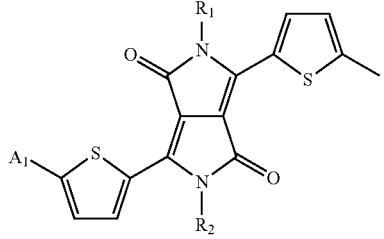

(VIII-E)

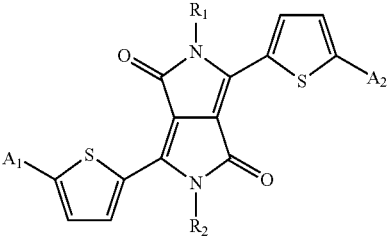

(VIII-F)

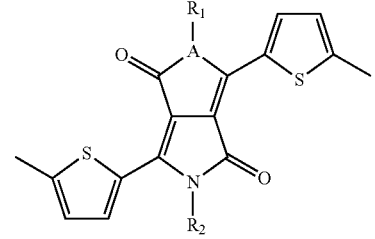

(VIII-G)

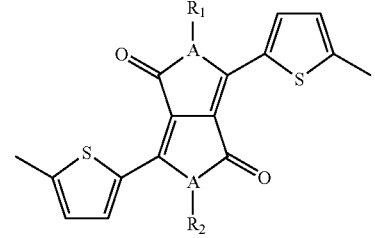

(VIII-H)

Polymers can be prepared which exclude such moieties as VIII-D to VIII-H, or use them as a minor component by molar ratio compared to the amount of a major acceptor component.

These materials, including polymeric materials, comprising moieties such as those shown in structures VIII and IX can be fabricated into solutions, inks, coated substrates, and organic electronic devices, including photovoltaic devices, as can the materials described above in Part IA. The lower molecular weight materials, including dimers, trimers, and oligomers, can be adapted to be polymerizable for use in polymerization reactions. They can be, for example, functionalized to comprise at least two polymerizable groups which are capable of participating in polymerization reactions. Polymerization reactions are described throughout this application including, for example, cross-coupling polymerization.

Polymers can be prepared which comprise both structures I and VIII. However, in some embodiments, the materials do not comprise the moiety of structure I.

In some embodiments, the materials, including oligomers and polymers, comprise a donor-acceptor structure, wherein the acceptor comprises (VIII).

In some embodiments, the materials, including the polymers, are soluble. In some embodiments, the R groups, R1 and R2, can be adapted to provide the polymer with solubility. In some embodiments, the R groups, R1 and R2, can each comprise optionally substituted alkyl, optionally substituted linear alkyl, optionally substituted branched alkyl, optionally substituted cycloalkyl, optionally substituted aryl, optionally substituted alkylaryl, optionally substituted arylalkyl, optionally substituted alkoxy, or optionally substituted aryloxy, and optionally, wherein R groups, R1 and R2, further comprises fluorine. Examples of fluorinated R groups include fluorinated alkyl and fluorinated aryl groups, including perfluorinated alkyl groups and perfluorinated aryl groups.

The structure VIII can be a symmetrical structure. For example, in some embodiments, the R groups, R1 and R2, are the same, and A1 and A2 are also the same. However, R1 and R2 can be different, and A1 and A2 can be different.

In some embodiments, the fused ring systems in VIII can comprise at least one thiophene fused ring, wherein the thiophene ring is directly linked to the substructure IX. For example, polymers can be also prepared wherein the backbone comprises a structure represented by VIII-B:

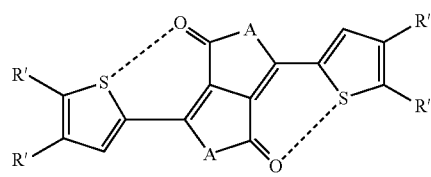

(VIII-B)

Here, A can be a heteroatom such as, for example, N, O, S, or Se and may be optionally substituted with alkyl, aryl, perfluoroalkyl, perfluoroaryl, alkyl-aryl as described above with respect to structure I and other structures. The R' groups in VIII-B can form additional ring systems, including fused ring systems, and the structure VI can be linked into the polymer chain via the illustrated thiophene rings. For example, the R' groups can form a benzene ring, a naphthalene ring, or a ring comprising silicon (silole). In structure VIII-B, a potential interaction is shown between carbonyl oxygen and thiophene sulfur, although the claimed inventions are not limited by the theory of this interaction.

Examples of polymers comprising the diketopyrrolopyrrole-based structure include polymers as represented by the following structures:

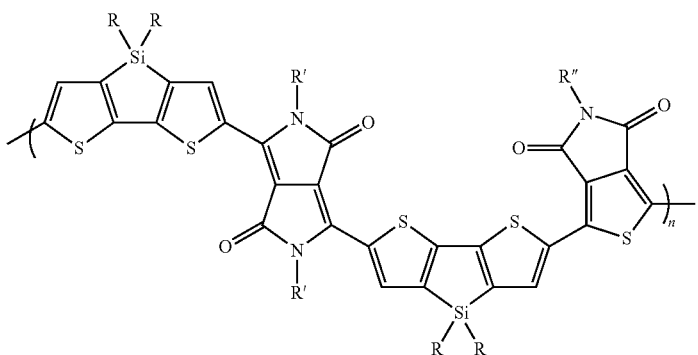

(X-A)

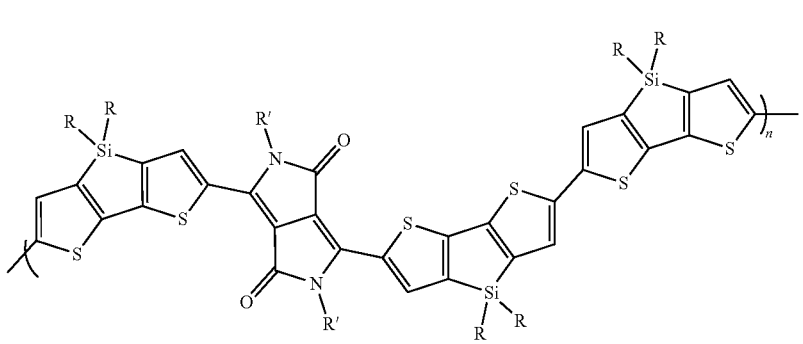

(X-B)

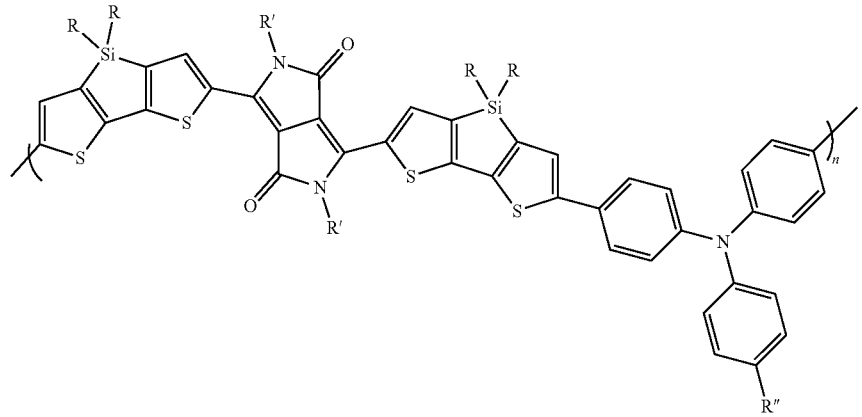
(X-C)
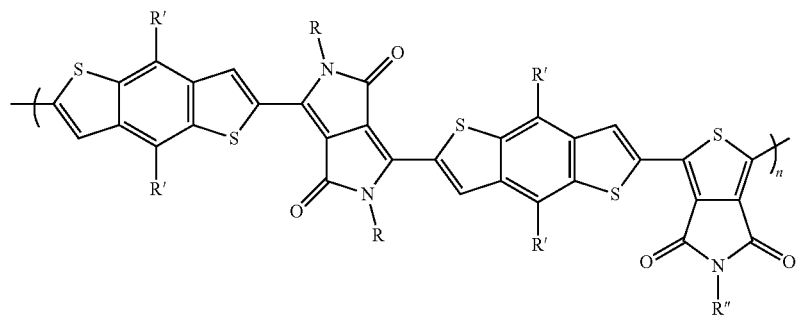
(X-D)
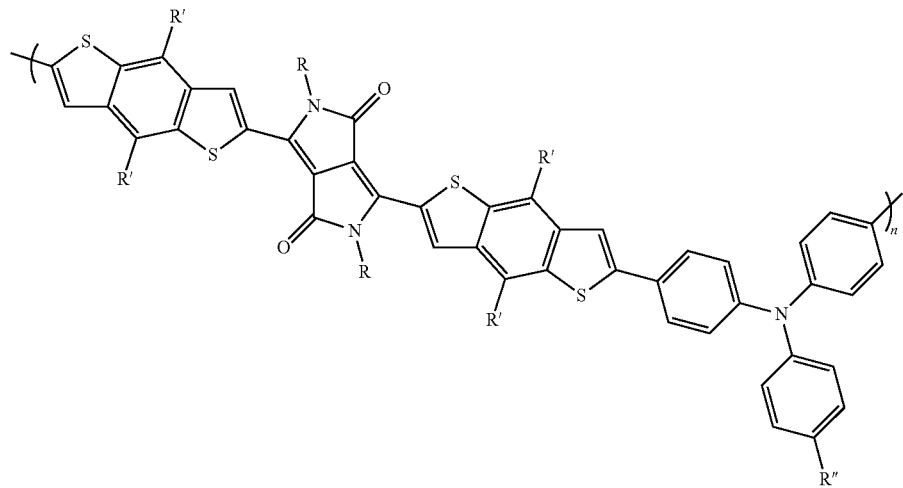
(X-E)
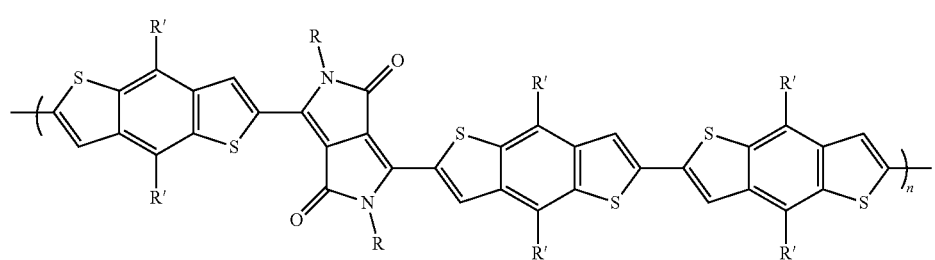
(X-F)

-continued
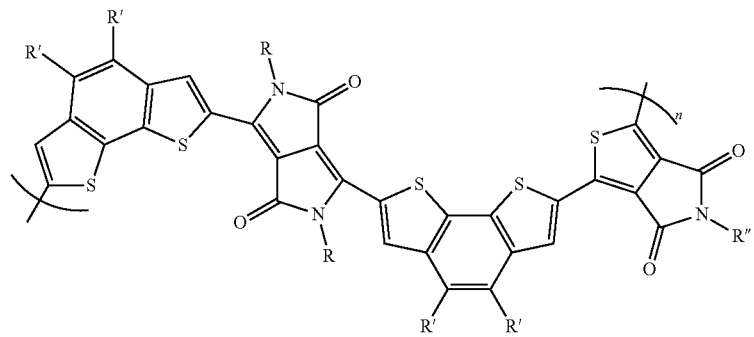
(X-G)
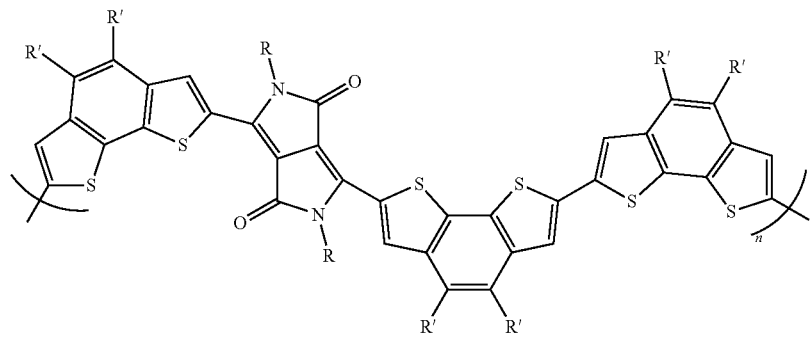
(X-H)
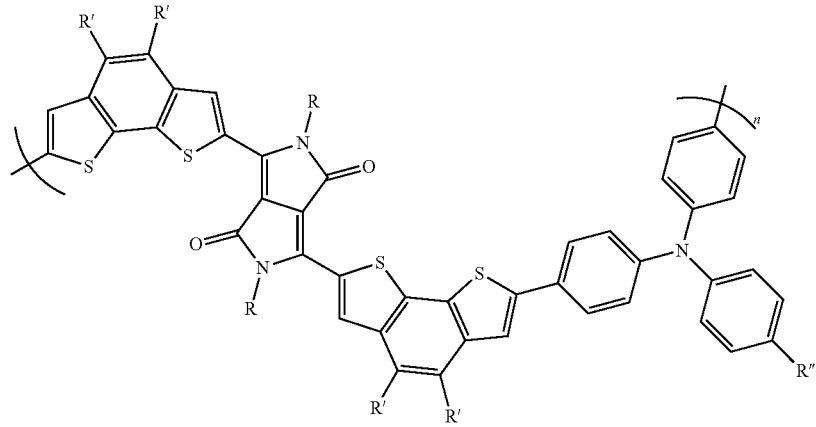
(X-I)
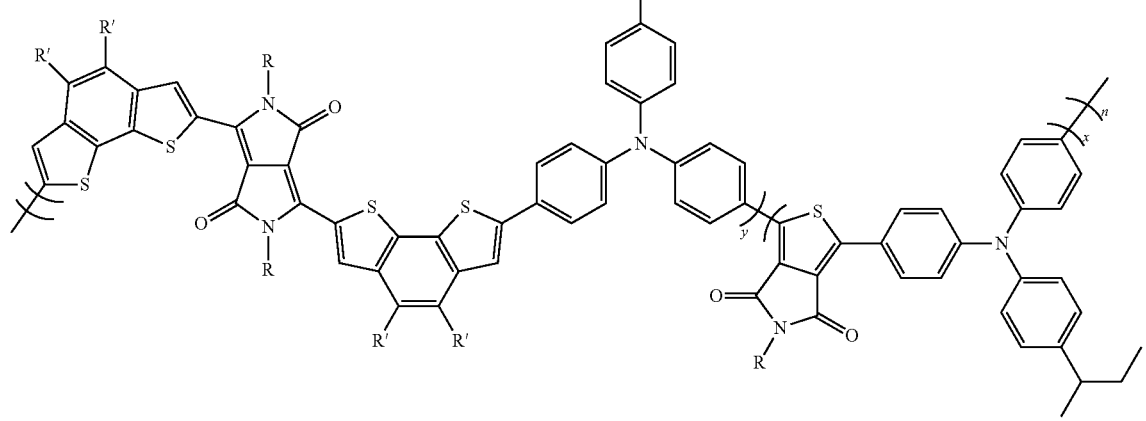
(X-J)
In structures X, the variables shown such as n, x, and y can be adapted according to the descriptions herein to control molecular weight and copolymer structure. Moreover, R, R', and R" can be the same or different for a given polymer chain and can be as described above for structure I and other polymer side groups described herein.

Additional embodiments for the diketopyrrolopyrrole-based materials include the following moieties, which can be found in dimers, trimers, oligomers, or high polymers:
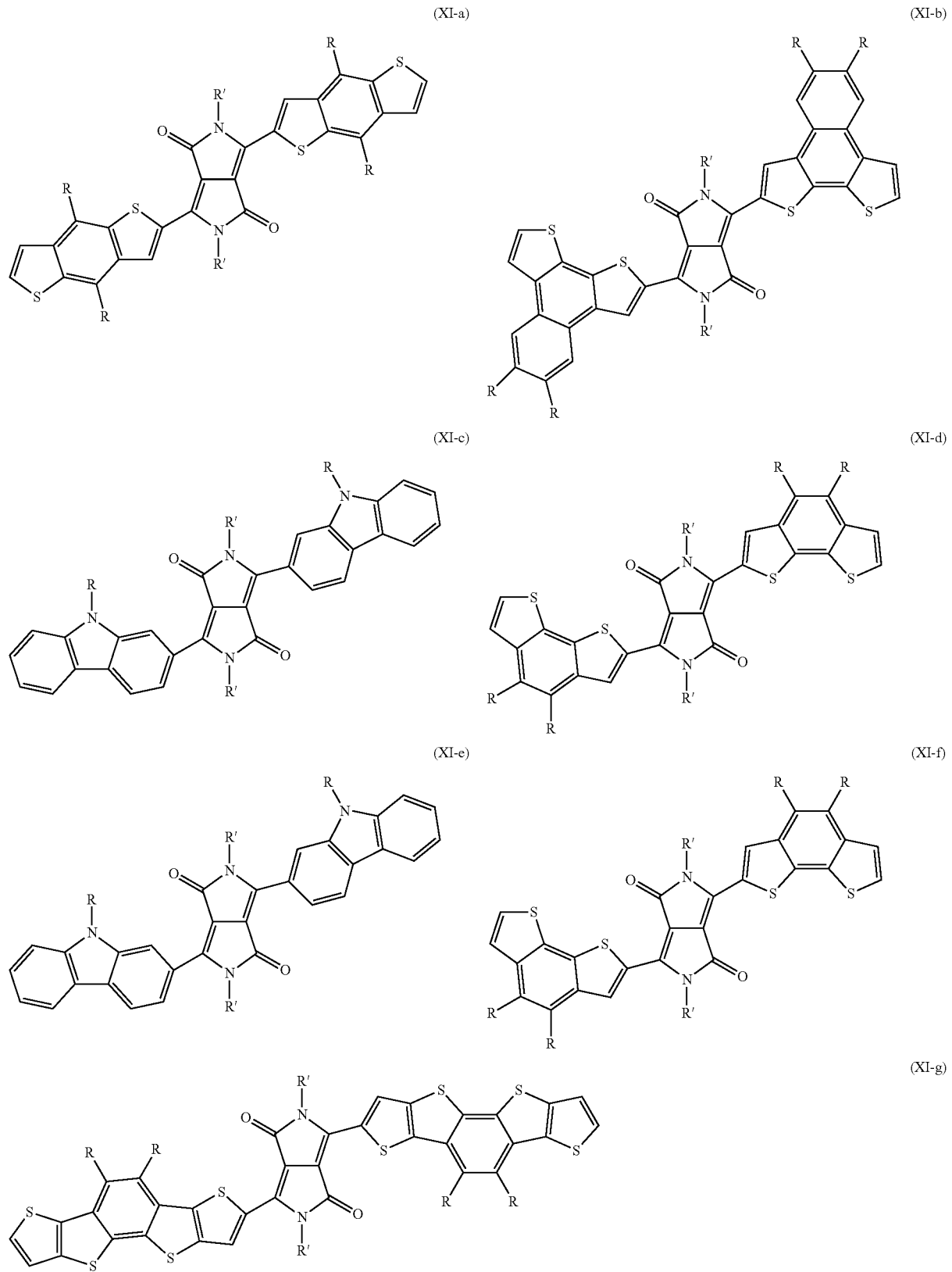

-continued
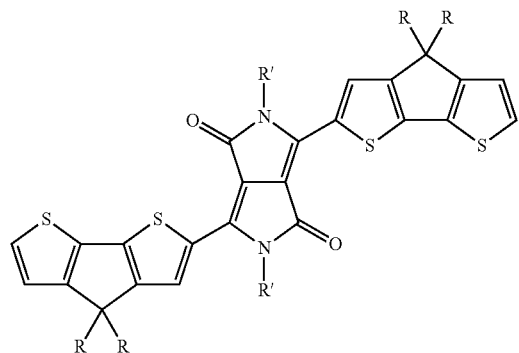
(XI-h)
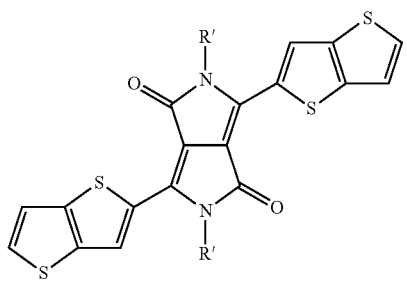
(XI-i)
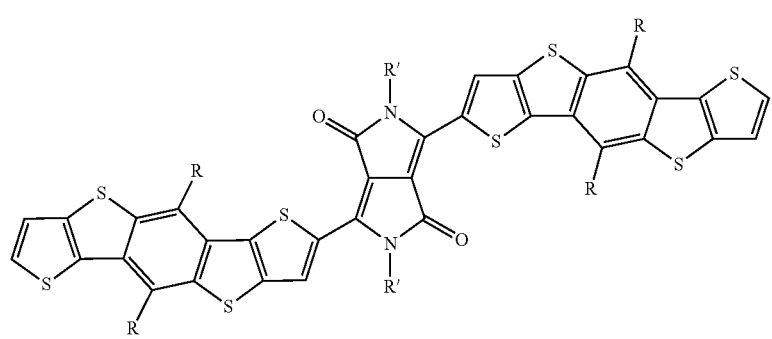
(XI-j)
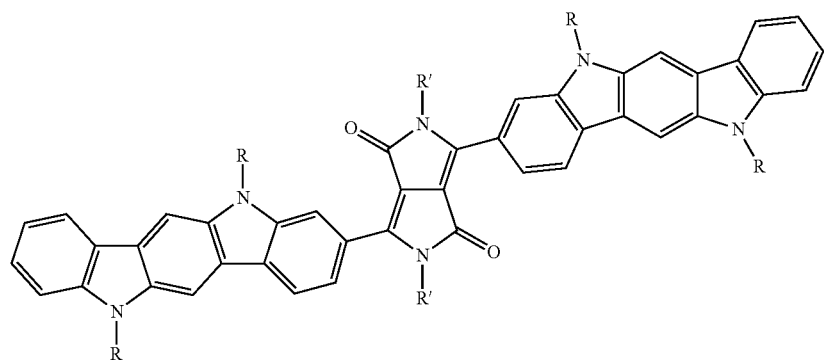
(XI-k)
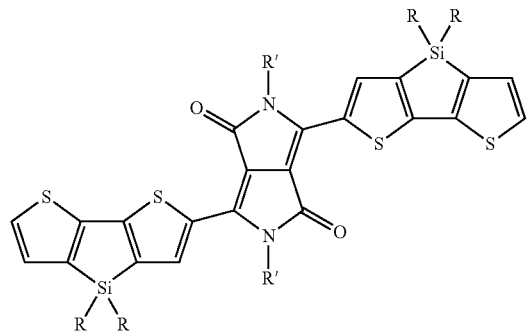
(XI-l)

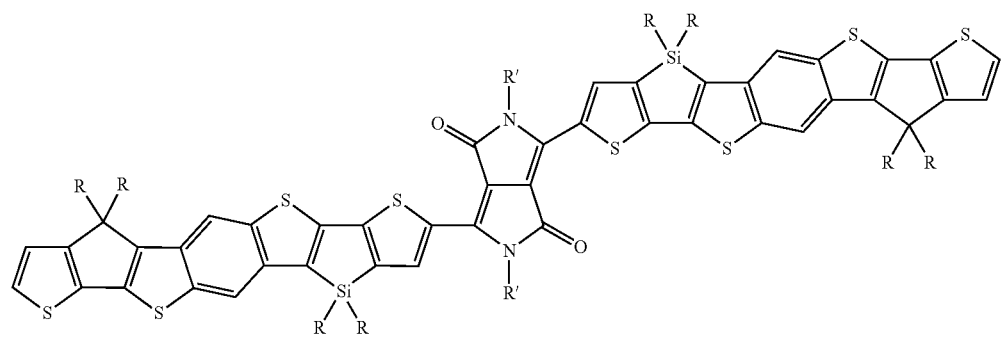
(XI-m)
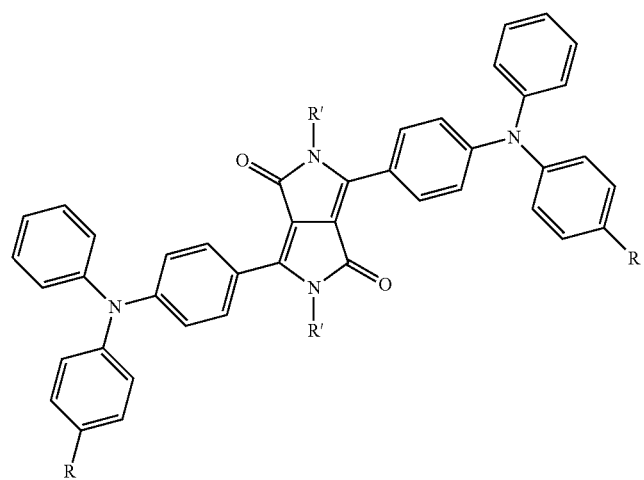
(XI-n)
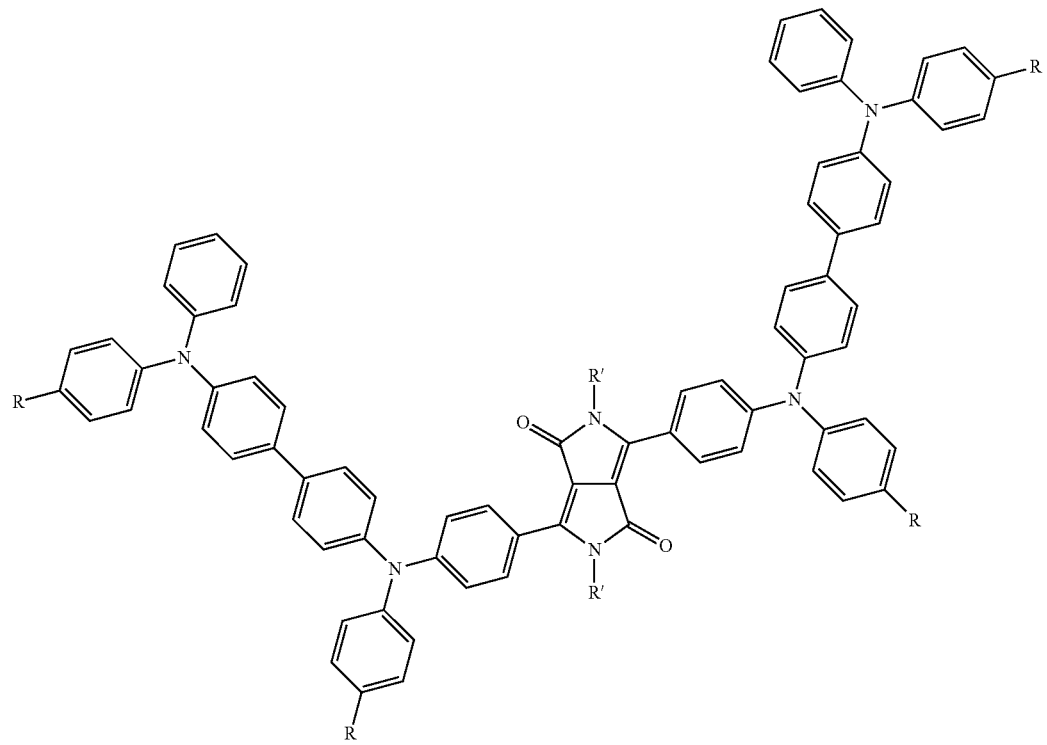
(XI-o)

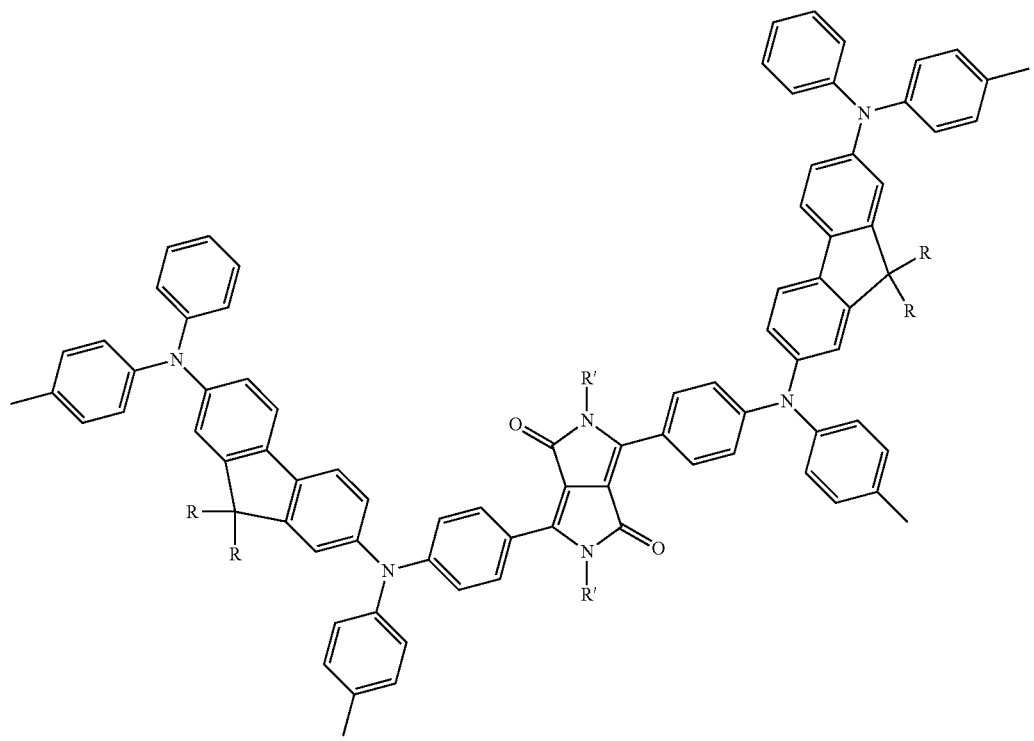

(XI-p)

In some embodiments, such as structures XI-n, XI-o, and XI-p, some of the DPP unit (structure IX) can be directly, covalently linked to the unfused phenyl ring of an arylamine moiety.

In structures XI, the side groups R and R' can be as described above, and the R and/or R' groups for a given polymer can be the same or different for a given polymer.

Polymers can be prepared which have a microstructure as shown in Chart I and can provide different copolymer microstructure based on multiple acceptors A1, A2, and the like, and/or multiple donors, D1, D2, and the like. Polymers can be prepared which have donors and acceptors IV as shown in FIGS. 1 and 2.

Polymers can be prepared which show an intramolecular non-covalent interaction, as described above, in, for example, a carbonyl interaction with an adjacent thiophene ring.

Polymers can be prepared wherein all or substantially all of the units shown in VIII are directly, covalently linked to the fused ring systems, or wherein only a fraction of the units shown in VIII are directly, covalently linked to the fused ring systems.

Diketopyrrole monomers can be made according to known procedures from extensive literature precedent. See, for example, Peet et al., *Appl. Phys. Lett.,* 2009, 93, 163306; Janssen et al. *Adv. Mat.,* 2008, 20, 2556; Zhu, Y. Ph.D. Dissertation, University of Koln, Germany, 2006; Yang et al. *J. App. Polymer Sci,* 2009, 111, 1976; EA00962499A2; EB0094911B1; EB00133156B1; EB00181290B1; EB00302018B1; EB00672729B1; EB 00962499B2; Tamayo et al., *J. Phys. Chem. C.,* 2008, 17402; Boens et al., *Int. J. Photoenergy,* 2004, V6, 2004, 159; Lunak et al., *J. Fluoresc Chem.* 2008, 18, 1181; Tamayo et al. *APL,* 2009, 94, 103301; Tamayo et al., *J. Phys. Chem. C,* 112, 11545; U.S. Pat. Nos. 4,585,878B1; 4,778,899B1; 4,921,566B1; WO08000664A1; Burgi et al., *Adv. Mater.* 2008, 20, 2217.

For example the new monomers can be prepared according to the following typical sequence:

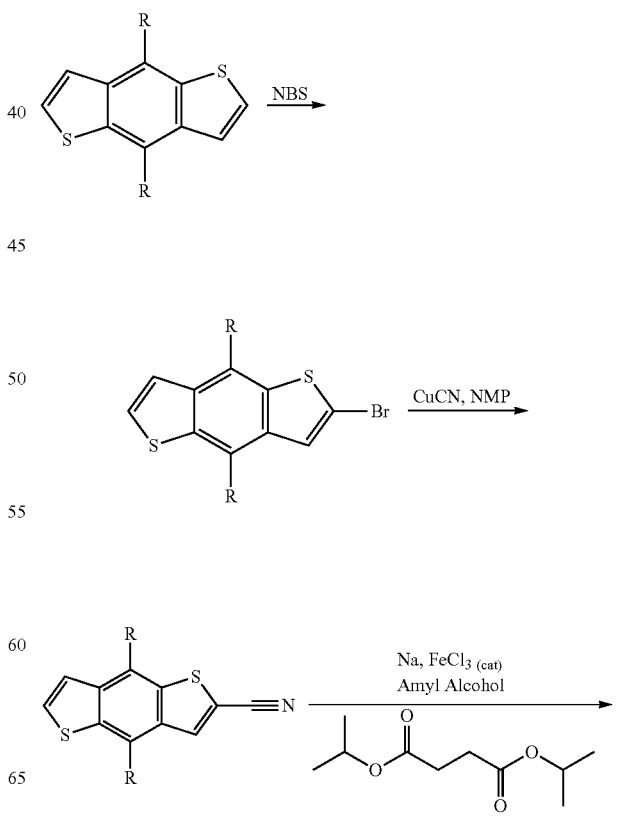

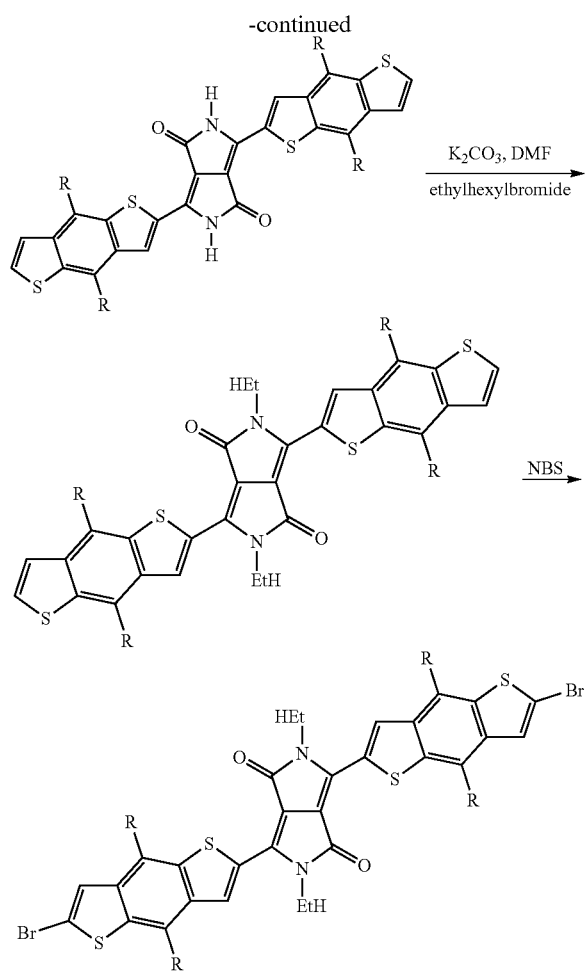

PART II. FURTHER EMBODIMENTS AND APPLICATIONS

Uses of Polymers

The materials, monomers, dimers, trimers, oligomers, polymers, and copolymers described herein in Part I, including Parts IA and IB, the working examples, and claims, can be used in organic electronic devices including, for example, OLEDs, OPVs including as OPV active layer, transistors, OFETs, batteries, and printed electronics generally, as well as sensors. The methods described in Part II can be adapted for the particular compounds and polymers being used.

For example, photovoltaic cells (solar cells) are known in the art. See, for example, Sun and Sariciftci, *Organic Photovoltaics, Mechanisms, Materials, and Devices,* 2005. The photovoltaic cell can comprise an active layer comprising a composition comprising at least one p-type material and at least one n-type material. One can engineer HOMO, LUMO, and band gaps for the p- and n-type materials for good performance. The morphology of the active layer can be adapted to provide good performance. For example, a nanoscale morphology can be prepared. An example is a bulk heterojunction.

The photovoltaic device can comprise at least one cathode, at least one anode, and at least one photovoltaic active layer disposed between the cathode and anode. The active layer can comprise a p-type material and an n-type material.

In an OPV active layer, the polymers described herein, which can be a p-type material, can be combined with n-type materials or acceptor moieties, such as, for example, fullerenes and fullerene derivatives. An example of a fullerene derivative is PCBM. Fullerenes can be also derivatized, for example, as described in PCT Patent Publication WO 2008/018931 filed May 2, 2007 and US Patent Publication 2008/0319207 published Dec. 25, 2008, both to Laird, et al. (Plextronics, Inc.). Other types of n-type materials known in the art can be used. If desired, larger area photovoltaics can be fabricated. See, for example, Bundgaard et al., *Solar Energy Materials and Solar Cells,* 2007, 91, 1019-1025.

Polymer solar cells, including polymer fullerene solar cells, are described in, for example, Hoppe et al., *Adv. Polym. Sci.* (2008), 214: 1-86; Zhu et al., "Design Rules for Efficient Organic Solar Cells," Chapter 13, 195-222 in *High-Efficient Low-Cost Photovoltaics,* Springer, 2009.

OLED devices are known in the art including white OLEDs, or WOLEDs. See, for example, Li and Meng, *Organic Light Emitting Materials and Devices,* CRC Taylor, 2006 and US Patent Publication 2006/0078761 published Apr. 13, 2006. The devices can comprise, for example, multilayer structures including, for example, an anode, including a transparent conductor, such as a transparent conductive oxide (TCO) on glass or PET or PEN; a hole injection layer; an electroluminescent layer, such as a polymer layer; a conditioning layer, such as LiF, and a cathode, such as for example Ca, Al, or Ba.

Methods known in the art can be used to fabricate organic electronic devices including for example OLED devices. Methods known in the art can be used to measure brightness, efficiency, and lifetimes. OLED patents include for example U.S. Pat. Nos. 4,356,429 and 4,539,507 (Kodak). Conducting polymers which emit light are described in for example U.S. Pat. Nos. 5,247,190 and 5,401,827 (Cambridge Display Technologies). See also Kraft et al., "Electroluminescent Conjugated Polymers—Seeing Polymers in a New Light," *Angew. Chem. Int. Ed.,* 1998, 37, 402-428, including device architecture, physical principles, solution processing, multilayering, blends, and materials synthesis and formulation, which is hereby incorporated by reference in its entirety.

In addition, printed electronics are generally known in the art. See, for example, *Printed Organic and Molecular Electronics,* Ed. D. Gamota et al., 2004. For example, Chapters 1 and 2 describe organic semiconductors, Chapter 3 describes manufacturing platforms for printing circuits, Chapter 4 describes electrical behavior of transistors and circuits, Chapter 5 describes applications, and Chapter 6 describes molecular electronics. See also Pope et al., *Electronic Processes in Organic Crystals and Polymers,* 1999.

Solutions and Ink Formulations

The materials, polymers, and copolymers can be put into solution or dispersion form, including ink formulations, for further processing, adapting to the particular application at hand including electronic devices, such as, OLED, solar cells and active layers of solar cells.

Lower cost electronic devices can be enabled because polymers, such as those described herein, can be processed into inks which can then be handled in the same manner as inks in conventional printing processes. Ink compositions used for forming, for example, the active layer of an organic photovoltaic device can be made by dissolving p-type and n-type materials in a solvent system, optionally containing other additives.

The solvents and conjugated polymer inks can be formulated or adapted for use in a particular application such as a solar cell that may include additional additives, such as electron acceptors. The additive(s) and solvents can be adapted to provide good dispersability of the n- and p-type materials, solubility of the n- and p-type materials, and stability of the ink formulation. For example, solvents can be used which provide good solubility or dispersability for fullerenes or fullerene derivative n-type compounds. Solvents can be adapted to be environmentally friendly in view of regulations, and can be, for example, halogen free. In other embodiments, additives can be included in the ink that improve the final film morphology or other properties. For example, solvent additives disclosed in US Patent Publication entitled "Processing Additives for Fabricating Organic Photovoltaic Cells" 2009/0108255 to Bazan et al., published on Apr. 30, 2009 can be included.

Solvent(s) and solvent additive(s) can be removed from the ink compositions, and films can be formed. Solid films can be formed that either comprise solvent(s) and solvent additive (s), are substantially free of solvent(s) and solvent additive(s), or are free of solvent(s) and solvent additive(s). For example, the amount of remaining solvent can be less than about 5% by weight, or less than about 1% by weight, or less than about 0.1% by weight. For example, the amount of remaining solvent additive can be less than about 5% by weight, or less than about 1% by weight, or less than about 0.1% by weight.

Conventional methods can be used to east polymer materials from the compositions to provide solid forms, including thin film forms and printed forms. For example, the p-type and n-type polymers of the active layer can be dissolved in the solvent to form an ink, and then allowed to dry. Suitable coating methods are known. These include roll coating, screen printing, spin casting, spin coating, doctor blading, dip coating, spray coating, or ink jet printing, and other known coating and printing methods.

Ink Components

Ink components known in the art can be used including, for example, solvents and n-type materials. The amounts of the components can be adapted to improve performance.

N-Type Materials

The active layer composition in, for example, a solar cell may include an n-type component or electron acceptor, or an electron acceptor moiety. These can be materials with a strong electron affinity and good electron accepting character. The n-type component should provide fast transfer, good stability, and good processability. The n-type material is desirably soluble in, dispersible in, or otherwise miscible with the solvents in order to provide for solution processing. The n-type component may take the form of particles, including microparticles and nanoparticles, inorganic particles, organic particles, and/or semiconductor particles.

For example, the active layer can comprise an n-type material comprising at least one fullerene structure. Fullerenes are known in the art. Fullerenes can be described as spheroidal carbon compounds. For example, the fullerene surface can present [6,6] bonding and [6,5] bonding as known in the art. The fullerene can have a surface comprising six-membered and five-membered rings. Fullerenes can be for example C60, C70, or C84, and additional carbon atoms can be added via derivative groups. See for example Hirsch, A.; Brettreich, M., *Fullerenes: Chemistry and Reactions*, Wiley-VCH Verlag, Weinheim, 2005, which is hereby incorporated by reference including teachings for fullerene nomenclature and synthesis, derivatization, reduction reactions (Chapter 2), nucleophilic additions (Chapter 3), cycloadditions (Chapter 4), hydrogenation (Chapter 5), radical additions (Chapter 6), transition metal complex formation (Chapter 7), oxidation and reactions with electrophiles (Chapter 8), halogenation (Chapter 9), regiochemistry (Chapter 10), cluster modification (Chapter 11), heterofullerenes (Chapter 12), and higher fullerenes (Chapter 13). Methods described herein can be used to synthesize fullerene derivatives and adducts.

In particular, the active layer can comprise at least one n-type material, wherein the n-type material comprises at least one derivatized fullerene or fullerene derivative. The derivative compound can be for example an adduct. The terms "derivatized fullerene," "fullerene derivative" as used herein, can be used interchangeably and can be, for example, fullerenes comprising, from 1 to 84, or 1 to 70, or 1 to 60, from 1 to 20, from 1 to 18, from one to ten, or from one to six, or from one to five, or from one to three substituents each covalently bonded to, for example, one or two carbons in the spheroidal carbon compounds. The derivatized fullerene can comprise a fullerene covalently bonded by [4+2] cycloaddition to at least one derivative moiety, R.

An example of an n-type material is PCBM.

Examples of n-type materials are described in, for example, International Patent Publication No. WO/2008/018931 published on Feb. 14, 2008 and US Patent Publication 2008/0319207 published Dec. 25, 2008, both to Laird, et al.

Solvent

The solvents useful for the presently claimed inventions can include, for example, halogenated benzenes, alkyl benzenes, halogenated methane, and thiophenes derivatives, and the like. More specifically, solvent can be for example chlorobenzene, dichlorobenzene, xylenes, toluene, chloroform, 3-methylthiophene, 3-propylthiphene, 3-hexylthiophene, and mixtures thereof. At least two solvents can be used.

The solvent system can include at least two solvents, at least one first solvent and at least one second solvent (e.g., a solvent additive), which are different from each other. They can be organic solvents. Particularly useful solvent systems can be used as described in co-pending U.S. patent application entitled "Solvent System for Conjugated Polymers," Ser. No. 12/113,058 filed on May 2, 2007, to Sheina et al., and co-pending U.S. patent application entitled "Improved Solvent System," Ser. No. 12/541,500 filed Aug. 14, 2009, which are hereby incorporated by reference in their entirety.

Solvent Additives

Solvent additives can be used, wherein a relatively small addition of a component (e.g., 1-3 wt %) can have a large impact on performance. For example, a primary or first solvent can be used in conjunction with a solvent additive. Solvent additives can be volatile and can be removed upon solvent removal. Or solvent additives can be less volatile and stay in the film upon solvent removal.

Different examples exist for solvent additives. For example, a solvent additive can comprise at least one heterocyclic ring. The heterocyclic ring can be, for example, at least one thiophene ring. The second solvent can be for example an alkylthiophene. In some instances the heterocyclic ring is not a nitrogen-containing ring. Or it can be a nitrogen containing ring. Thus, in some embodiments the second solvent is or is not a pyridine, pyrazine, pyrimidine, or a pyrrolidinone. In some embodiments, the heterocyclic ring includes at least one S atom and at least one O atom. Examples of suitable solvent additives include, but are not limited to, thiophene derivatives (i.e., substituted thiophenes). The thiophene ring may be substituted or unsubstituted in different positions on the ring. However, in some instances the thiophene derivatives do not contain halogen atoms. Alkylthiophenes and combinations thereof may be used as the second solvent. The alkyl group can be, for example, C1, C2, C3, C4, and the like up to and including C8, C12, C16, and C20. The alkyl group can be linear or branched. Specific examples of suitable alkylthiophenes include methylthiophene, ethylthiophene, propylthiophene, butylthiophene, pentylthiophene, hexylthiophene, heptylthiophene, octylthiophene, nonylthiophene, and decylthiophene.

Other examples of solvent systems can be used as described in the aforementioned co-pending US patent applications, in US Patent Publication entitled "Processing Additives for Fabricating Organic Photovoltaic Cells" 2009/0108255 to Bazan et al., published on Apr. 30, 2009 or in Peet, et al., "Efficiency enhancement in low-bandgap polymer solar cells by processing with alkane dithiols," *Nat. Mater.*, 2007, 6, 497-500.

Device Preparation

Devices can be made comprising one or more layers comprising the polymers described herein and one or more electrodes, including anode and cathode. Layers can be built up on a substrate. See, for example, Chen et al., *Advanced Materials*, 2009, 21, 1-16.

Devices using the presently claimed inventions can be made using for example ITO as an anode material on a substrate. Other anode materials can include for example metals, such as Au, carbon nanotubes, single or multiwalled, and other transparent conducting oxides. The resistivity of the anode can be maintained below, for example, 15 Ω/sq or less, 25 or less, 50 or less, or 100 or less, or 200 or less, or 250 or less. The substrate can be rigid or flexible and can be, for example, glass, plastics (PTFE, polysiloxanes, thermoplastics, PET, PEN and the like), metals (Al, Au, Ag), metal foils, metal oxides, (TiOx, ZnOx) and semiconductors, such as Si. The ITO on the substrate can be cleaned using techniques known in the art prior to device layer deposition.

A variety of layers can be included between the anode and the active layer of a solar cell or the emissive layer of an OLED. These layers are generally referred to as hole transport layer (HTL), hole injection layers (HIL), hole collection (HCL), electron blocking layers (EBL) and/or interlayers.

Various kinds of hole transport layers, hole injection layers, hole collection layers, and/or hole extraction layers can be used. For example, hole transport layers of various kinds are described in the following references: 1) U.S. Pat. No. 7,569,159, issued Aug. 4, 2009 to Hammond et al.; U.S. Ser. No. 11/826,394, filed Jul. 13, 2007, published Oct. 9, 2008 as 2008/0248313; U.S. Ser. No. 12/422,159, filed Apr. 9, 2009; U.S. Ser. No. 61/108,851, filed Oct. 27, 2008; and U.S. Ser. No. 61/115,877, filed Nov. 18, 2008.

Hole transport layers (HTL) can be added using, for example, spin casting, ink jetting, doctor blading, spray casting, dip coating, vapor depositing, or any other known deposition method.

The HTLs can be formed as films from, for example, PEDOT, PEDOT/PSS or TBD, or NPB, or PLEXCORE® OC inks (Plextronics, Pittsburgh, Pa.).

The thickness of the HTL or HIL layer can be for example from about 10 nm to about 300 nm thick, or from 30 nm to 60 nm, 60 nm to 100 nm, or 100 nm to 200 nm. The film then can be optionally dried/annealed at 110 to 200° C. for 1 min to an hour, optionally in an inert atmosphere.

Active layer thickness can be, for example, about 50 nm to about 250 nm, including for an OPV device.

The active layer can be formulated from a mixture of n-type and p-type materials. The n- and p-type materials can be mixed in a ratio of for example from about 0.1 to 4.0 (p-type) to about 1 (n-type) based on a weight, or from about 1.1 to about 3.0 (p-type) to about 1 (n-type) or from about 1.1 to about 1.5 (p-type) to about 1 (n-type). The amount of each type of material or the ratio between the two types of components can be varied for the particular application.

The active layer can be then deposited by spin casting, ink jetting, doctor blading, spray casting, dip coating, vapor depositing, or any other known deposition method, on top of the HTL or HIL film. The film is then optionally thermally annealed at, for example, about 40 to about 250° C., or from about 150 to 180° C., for about 10 min to an hour in an inert atmosphere. Solvent annealing can be also carried out as needed.

A cathode layer can be added to the device, generally using for example thermal evaporation of one or more metals. For example, a 1 to 15 nm Ca layer is thermally evaporated onto the active layer through a shadow mask, followed by deposition of a 10 to 300 nm Al layer. A variety of layers can be included between the cathode and the active layer of a solar cell or the emissive layer of an OLED. These layers are generally referred to as electron transport layers (ETL), electron injection layers (EIL), hole blocking layers (HBL) and/or interlayers.

In some embodiments, an optional interlayer may be included between the active layer and the cathode, and/or between the HTL or HIL and the active layer. This interlayer can be, for example, from 0.5 nm to about 100 nm, or from about 1 to 3 nm, thick. The interlayer can comprise an electron conditioning, a hole blocking, or an extraction material, such as LiF, BCP, bathocuprine, fullerenes or fullerene derivatives, such as C60, C70, C84 and other fullerenes and fullerene derivatives discussed herein.

Electron transport layers can be used in, for example, solar cell devices. See, for example, U.S. patent application No. 61/116,963 filed Nov. 21, 2008.

The devices can be then encapsulated using a glass cover slip sealed with a curable glue, or in other epoxy or plastic coatings. Cavity glass with a getter/desiccant may also be used.

In addition, the active layer can comprise additional ingredients including for example surfactants, dispersants, oxygen and water scavengers.

The active layer can comprise multiple layers or be multilayered.

The active layer composition can be formed from an ink comprising a mixture as a film. Films and devices can be annealed before use and testing. Thermal annealing and solvent annealing can be carried out.

Inverted solar cells can be made. See, for example, Chen et al. *Advanced Materials*, 2009, 21, 1-16. Tandem solar cells can be made.

Device Testing

Known solar cell parameters can be measured including for example $J_{SC}$ (mA/cm$^2$) and Voc (V) and fill factor (FF) and power conversion efficiency (%, PCE) by methods known in the art. See for example Hoppe article cited above and references cited therein.

Oriel Solar Simulators can be used to determine PV properties including for example FF, Jsc, Voc, and efficiencies. The simulator can be calibrated by methods known in the art including for example calibration with a KG5-Si reference cell. External quantum efficiency (EQE) can be measured.

Other properties for the inks, films, and devices can be measured by methods known in the art.

Power conversion efficiency (PCE) can be, for example, at least about 1%, or at least about 2%, or at least about 3%, or at least about 4%, or at least about 5%, or at least about 6%, or at least about 7%, or at least about 8%, or higher.

Fill factor, which can be expressed as a number between 0 and 1, or a percentage between 0 and 100%, can be, for example, at least about 0.4 (40%), or at least about 0.5 (50%), or at least about 0.6, or at least about 0.7, or at least about 0.8, or at least about 0.9 or higher.

Open circuit voltage ($V_{oc}$) in V can be, for example, at least about 0.3, or at least about 0.4, or at least about 0.5, or at least about 0.6 V, or higher.

Short circuit current ($J_{sc}$) can be, for example, at least about 0.5, or at least about 0.6, or at least about 0.7, or at least about 0.8, or at least about 0.9, or at least about 1.0, or at least about 2.0, or at least about 3.0, or at least about 4.0, or at least about 5.0, or higher (mA/cm$^2$).

PART III: WORKING AND PROPHETIC EXAMPLES

Additional embodiments are provided by way of non-limiting working and prophetic examples.

I. Synthesis: Monomers and Polymers

The following synthetic examples are illustrative and not intended to be limiting. Unless specified, reactions were conducted under prepurified nitrogen or argon, using oven-dried and/or flame-dried glassware. Ice/water, dry ice/acetone were used for 0° and −78° C. baths, respectively. Commercial chemicals were purchased from commercial sources (e.g., Aldrich Chemical Co., Inc., Fisher Scientific, Acros, etc.) and used without further purification unless specified otherwise. Titration of the Grignard/organolithium reagents was performed following the procedure described by Love, B. E. et al. *J. Org. Chem.* 1999, 64, 3755. Reagent grade solvents were dried and/or purified by distillation or else when necessary.

Materials.

Synthesis of 4,4'-bis(2-ethylhexyl)dithieno[3,2-b:2',3'-d] silole [Lit. Ref.: Hou et al., *J. Am. Chem. Soc.* 2008, 130, 16144];

Synthesis of 4,8-dioctyloxybenzo[1,2-b;3,4-b] dithiophene and of modified 2,5-di-alkyl-2,5-dihydropyrrolo [3,4-c]-pyrrole-1,4-dione were adapted from published procedures, [Lit. Ref.: (1) Hou et al., *Macromolecules* 2008, 41, 6012, (2) Zou et al., *Macromolecules,* 2009, 42, 289, (3) Tamayo et al., *J. Phys. Chem. C,* 2008, 112, 15543], Synthesis of 2,5-diethylhexyl-3,6-bis(5-bromothiophen-2-yl)pyrrolo[3,4-c]-pyrrole-1,4-dione [Lit. Ref.: Tamayo et al., *J. Phys. Chem. C* 2008, 112, 15543], Synthesis of 4,7-dibromo-benzo[1,2,5]thiadiazole [Lit. Ref.; Hou, Q.; Xu, Y.; Yang, W.; Yuan, M.; Peng, J. Cao, Y. *Mater. Chem.* 2002, 10, 2887] were adapted from the published procedures.

Synthesis of 1,3-Dibromo-5-(2-ethylhexyl)thieno[3,4-c] pyrrole-4,6-dione; was received from Acoris, Inc. (synthesis was adapted from Zhang, Q. T.; Tour, J. M. *J. Am. Chem. Soc.* 1997, 119, 5065).

Example 1

2,6-bis(trimethyltin)-4,8-diethylhexyloxybenzo[1,2-b;3,4-b]dithiophene

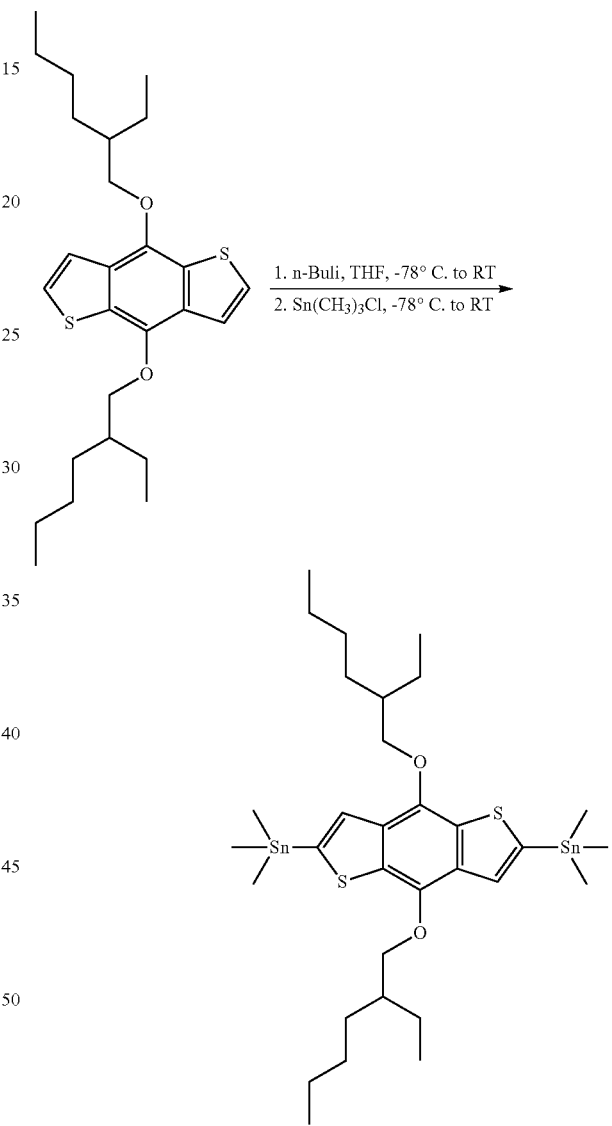

A dry 500-mL three-neck flask was flushed with N$_2$ and was charged with 4,8-diethylhexyloxybenzo[1,2-b;3,4-b] dithiophene (6.9 g, 0.015 mol) and diethyl ether (Et$_2$O) (150 mL, 0.1 M) via deoxygenated syringe. The reaction flask was cooled to −78° C. and a 1.7 M solution of tert-butyllithium in hexanes (23 mL, 0.038 mol) was added dropwise via deoxygenated syringe. After 30 minutes of stirring at −78° C., the solution was chilled to 0° C. and stirring was continued for 5 minutes, at which point the reaction mixture was chilled back to −78° C. A 1 M solution of thrimethyltin chloride in THF (39 mL, 0.038 mol) was added to the reaction flask dropwise and stirring continued for 1 hour at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with hexanes (150 mL) three times. The combined organic layer was washed with water two times and dried over anhydrous magnesium sulfate (MgSO$_4$). After the product was filtered, the solvent was removed by rotary evaporation. The crude product was purified by recrystallization three times from THF/methanol to yield white crystalline solid (7.3 g, 61%).

Spectral data: $^1$H NMR (300 MHz, CDCl$_3$): δ$_H$ 7.15 (s, 2H), 4.18 (d, 4H), 1.81 (m, 4H), 1.60 (m, 14H), 1.08 (t, 6H), 0.95 (t, 6H), 0.45 (s, 18H).

Example 2

4,4'-bis(2-ethylhexyl)-5,5'-bis(trimethyltin)dithieno[3,2-b:2',3'-d]silole

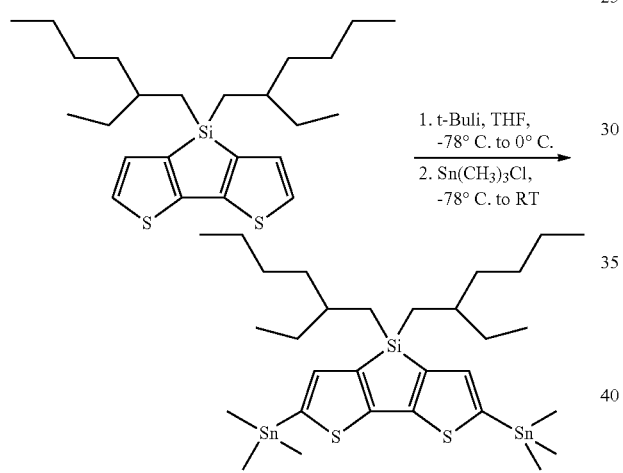

A dry 500-mL three-neck flask was flushed with N$_2$ and was charged with 4,4'-bis(2-ethylhexyl)dithieno[3,2-b:2',3'-d]silole (10.4 g, 0.025 mol) and THF (250 mL, 0.1 M) via deoxygenated syringe. The reaction flask was cooled to −78° C. and a 1.6 M solution of tert-butyllithium in hexanes (37 mL, 0.062 mol) was added dropwise via deoxygenated syringe. After 30 minutes of stirring at −78° C., the solution was chilled to 0° C. and stirring was continued for 5 minutes, at which point the reaction mixture was chilled back to −78° C. A 1 M solution of thrimethyltin chloride in THF (62 mL, 0.062 mol) was added to the reaction flask dropwise and stirring continued for 1 hour at −78° C. The cooling bath was removed and the reaction mixture was allowed to warm up to ambient temperature. As the reaction was completed, cool DI water (50 mL) was slowly added to the reaction flask. Then, the reaction mixture was poured into 200 mL of cool water and extracted with hexanes (200 mL) three times. The combined organic layer was washed with water two times and dried over anhydrous magnesium sulfate (MgSO$_4$). After the product was filtered, the solvent was removed by rotary evaporation. The product was obtained as yellow-greenish oil (17.5 g, 96%).

Spectral data: $^1$H NMR (300 MHz, CDCl$_3$): δ$_H$ 7.09 (s, 2H), 1.25 (m, 18H), 0.80 (m, 16H), 0.45 (s, 18H).

Example 3

2-trimethyltin-4,8-diethylhexyloxybenzo[1,2-b;3,4-b]dithiophene

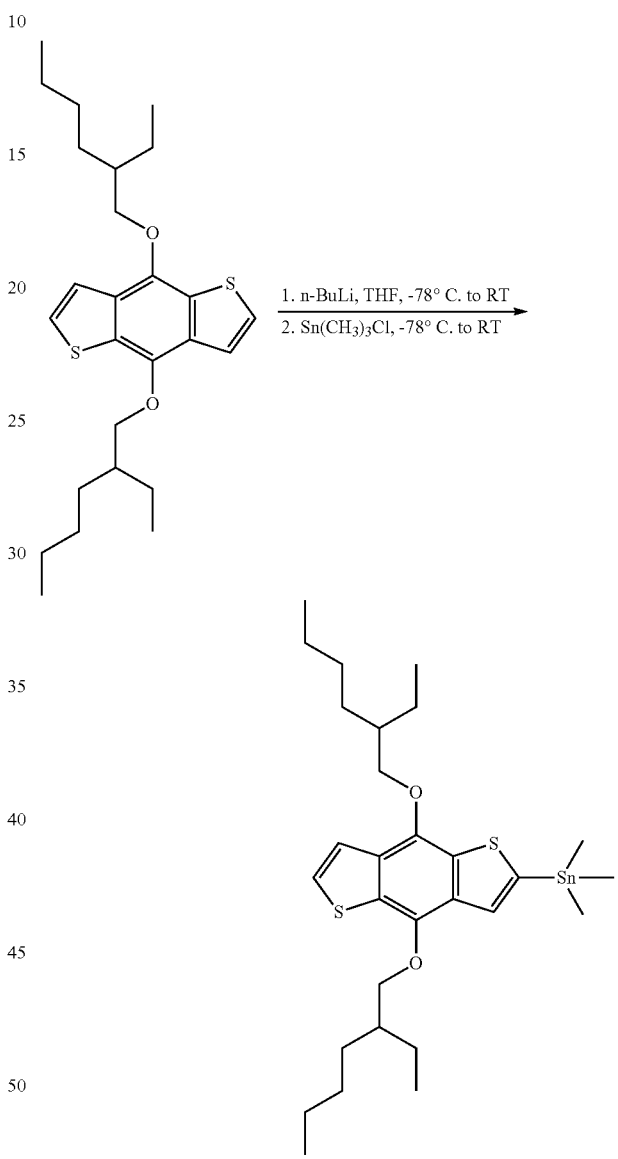

A dry 250-mL three-neck flask was flushed with N$_2$ and was charged with 4,8-diethylhexyloxybenzo[1,2-b;3,4-b]dithiophene (4.0 g, 9.0 mmol) and THF (100 mL, 0.10 M) via deoxygenated syringe. The reaction flask was cooled to −78° C. and a 2.17 M solution of n-butyllithium in hexanes (4.1 mL, 9.0 mmol) was added dropwise via deoxygenated syringe. After 30 minutes of stirring at −78° C., the solution was chilled to 0° C. and stirring was continued for 5 minutes, at which point the reaction mixture was chilled back to −78° C. A 1 M solution of thrimethyltin chloride in THF (13.5 mL, 13.5 mmol) was added to the reaction flask dropwise and stirring continued for 1 hour at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with hexanes (150 mL) three times. The combined organic layer was washed with water two times and dried over anhydrous magnesium sulfate ($MgSO_4$). After the product was filtered, the solvent was removed by rotary evaporation. The product was obtained as yellow oil (5.3 g, 96%).

Spectral data: $^1$H NMR (300 MHz, $CDCl_3$): $\delta_H$ 7.50 (d, 2H), 7.35 (s, 1H), 4.20 (s, 4H), 1.28-1.92 (bm, 20H), 0.98 (d, 12H), 0.46 (t, 9H).

Example 4

1,3-bis(4,8-diethylhexyloxybenzo[1,2-b;3,4-b] dithiophene)-5-(2-ethylhexyl)thieno[3,4-c]pyrrole-4,6-dione

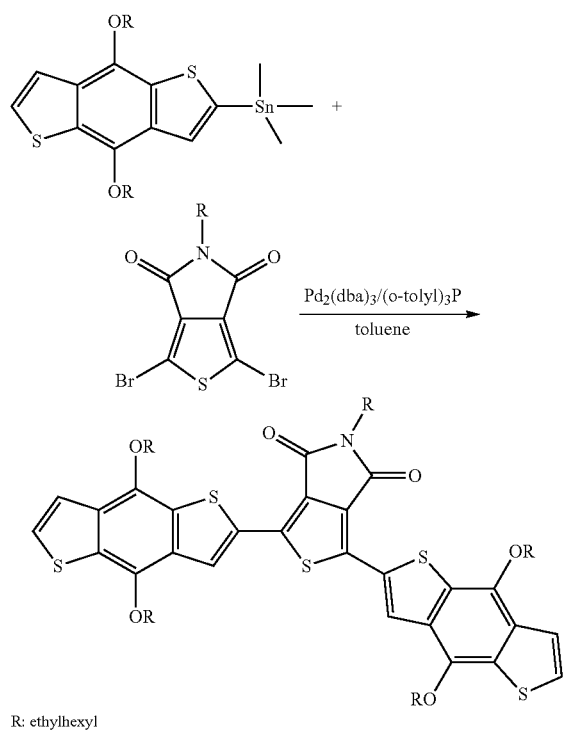

R: ethylhexyl

In a glove box, 2-trimethyltin-4,8-diethylhexyloxybenzo [1,2-b;3,4-b]dithiophene (1.0 g, 1.64 mmol), 1,3-dibromo-5-(2-ethylhexyl)thieno[3,4-c]pyrrole-4,6-dione (0.33 g, 0.78 mmol), tris(dibenzylideneacetone)dipalladium(0) (0.018 g, 0.020 mmol) and tris(o-tolyl)phosphine (0.024 g, 0.080 mmol) were weighted out into a flame dried 50 mL Schlenk flask. Reaction flask was removed from the glove box and 10 mL of deoxygenated toluene were added via syringe. The mixture was evacuated and refilled with argon five times. The reaction flask was immersed into a preheated to 110° C. oil bath and was left stirring under an argon stream for 2 hours. The oil bath was removed and after cooling to room temperature, the final mixture was poured into 40 mL of methyl tert-butyl ether (MTBE) and extracted with it (3×50 mL). The combined organic layer was washed with water two times and dried over anhydrous magnesium sulfate ($MgSO_4$). After the product was filtered, the solvent was removed by rotary evaporation. The product was first passed through a flash silica gel chromatography column with hexanes/chloroform (gradient), and then through a biobeads SX-1 column with chloroform. It was obtained as an orange waxy in appearance solid paste (0.40 g, 60%).

Spectral data: $^1$H NMR (300 MHz, $CDCl_3$): $\delta_H$ 8.76 (s, 2H), 7.47 (d, 2H), 7.42 (d, 2H), 4.32 (d, 4H), 4.20 (d, 4H), 3.63 (d, 2H), 1.25-1.94 (bm, 55H), 0.86-1.08 (bm, 30H).

Example 5

Bromination of 1,3-bis(4,8-diethylhexyloxybenzo[1,2-b;3,4-b]dithiophene)-5-(2-ethylhexyl)thieno[3,4-c]pyrrole-4,6-dione

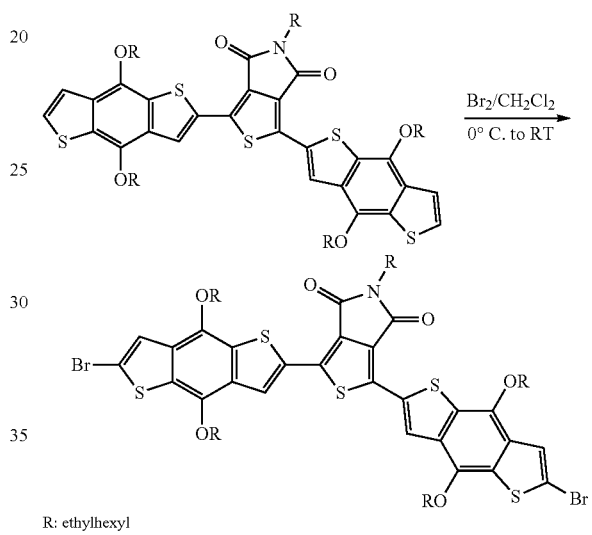

R: ethylhexyl

A dry 50-mL three-neck flask equipped with a condenser, a stir bar, addition funnel, and a gas (HBr) outlet was charged with 1,3-bis(4,8-diethylhexyloxybenzo[1,2-b;3,4-b] dithiophene)-5-(2-ethylhexyl)thieno[3,4-c]pyrrole-4,6-dione (0.20 g, 0.17 mmol). The flask was charged with anhydrous methylene chloride ($CH_2Cl_2$) (10 mL). The reaction flask was cooled down to 0° C. and bromine (0.06 mL, 0.37 mmol) in 10 mL of methylene chloride was added dropwise to the reaction flask via addition funnel. The solution mixture was stirred at 0° C. for 2 hours, and then at room temperature (RT) for an additional 6 hours. If necessary, a second portion of bromine solution could be added to the reaction flask and the reaction could proceed for additional 2 hours. Upon completion, the reaction was added to a $NaOH/NaHSO_3$ solution (5%). The layers were separated and the aqueous layer/ was extracted three times with MTBE, the organic layers collected, washed with NaOH, water, and dried over anhydrous $MgSO_4$. After the product was filtered, the solvent was removed by rotary evaporation. The crude product was first passed through a flash silica gel chromatography column with hexanes/chloroform (gradient), and then through a biobeads SX-1 column with chloroform. It was obtained as an orange viscous solid paste with yields ranging between 70 and 80%. The purity was checked by NMR.

Example 6 poly{2,6'-4,8-diethylhexyloxybenzo[1,2-b;3,4-b]dithiophene-ah-(5-(2-ethylhexyl)thieno[3,4-c]pyrrole-4,6-dione}

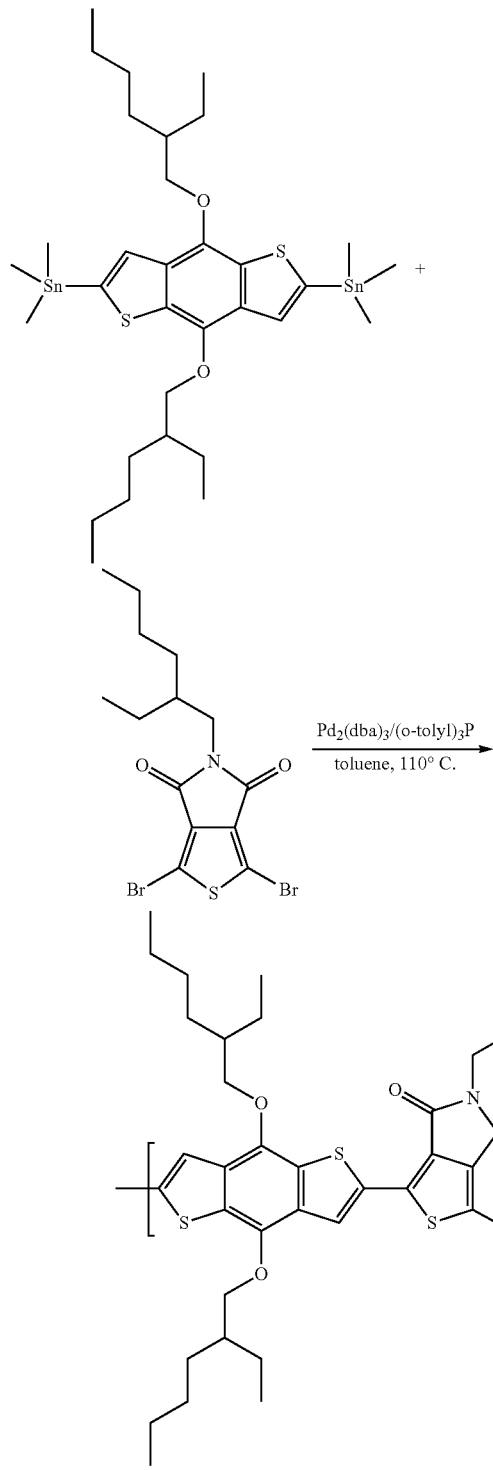

In a glove box, 2,6-bis(trimethyltin)-4,8-diethylhexyloxy-benzo[1,2-b;3,4-b]dithiophene (0.4 g, 0.52 mmol), 1,3-di-bromo-5-(2-ethylhexyl)thieno[3,4-c]pyrrole-4,6-dione (0.22 g, 0.52 mmol), tris(dibenzylideneacetone)dipalladium(0) (0.012 g, 0.013 mmol) and tris(o-tolyl)phosphine (0.016 g, 0.052 mmol) were weighted out into a flame dried 50 mL Schlenk flask. Reaction flask was removed from the glove box and 6 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.18 g, 50%). Molecular weight was determined by GPC in 1,3,5-trichlorobenzene (1 mL/min at 150° C.) vs. polystyrene standards: $M_n$=24,700, $M_w$=49,100, PDI=2.0.

Example 7 poly{4,4'-bis(2-ethylhexyl)dithieno[3,2-b:2',3'-d]silole-alt-5-(2-ethylhexyl)thieno[3,4-c]pyrrole-4,6-dione}

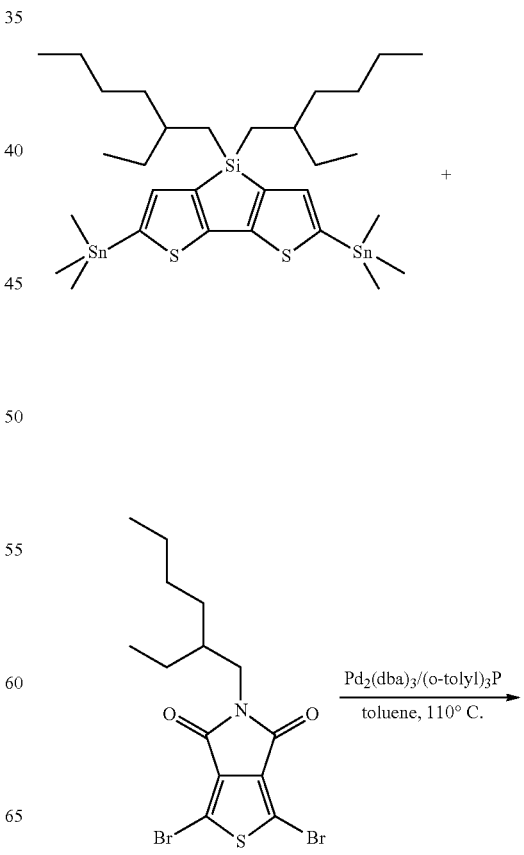

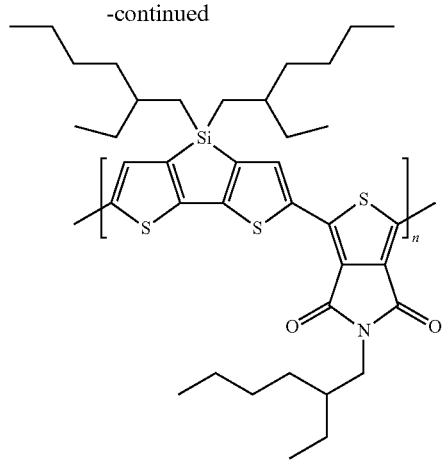

In a glove box, 4,4'-bis(2-ethylhexyl)-5,5'-bis(trimethyltin)dithieno[3,2-b:2',3'-d]silole (0.98 g, 1.3 mmol), 1,3-dibromo-5-(2-ethylhexyl)thieno[3,4-c]pyrrole-4,6-dione (0.50 g, 1.2 mmol), tris(dibenzylideneacetone)dipalladium(0) (0.030 g, 0.033 mmol) and tris(o-tolyl)phosphine (0.040 g, 0.13 mmol) were weighted out into a flame dried 100 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 36 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 500 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.14 g, 20% of chloroform soluble fraction). Molecular weight was determined by GPC in chloroform (1 mL/min at 35° C.) vs. polystyrene standards: $M_n$=9,900, $M_w$=16,000, PDI=1.6.

Example 8 poly{(4,4'-bis(2-ethylhexyl)dithieno[3,2-b:2',3'-d]silole-alt-5-(2-ethylhexyl)thieno[3,4-c]pyrrole-4,6-dione)-alt-(4,4'-bis(2-ethylhexyl)dithieno[3,2-b:2',3'-d]silole-alt-5-diethylhexyl-3,6-dithiophen-2-ylpyrrolo[3,4-c]pyrrole-1,4-dione)}

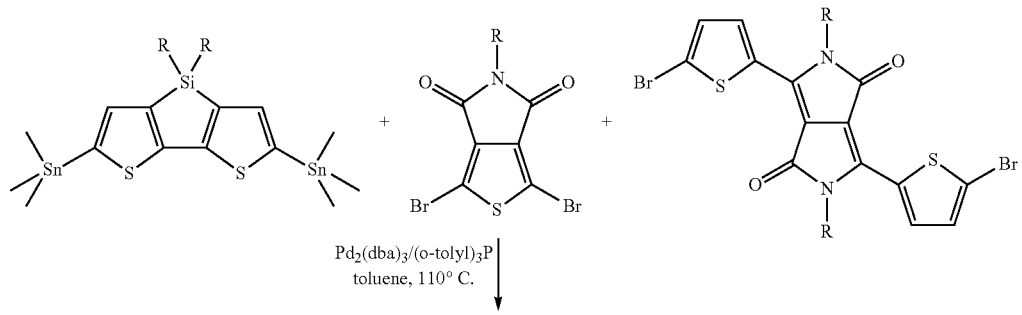

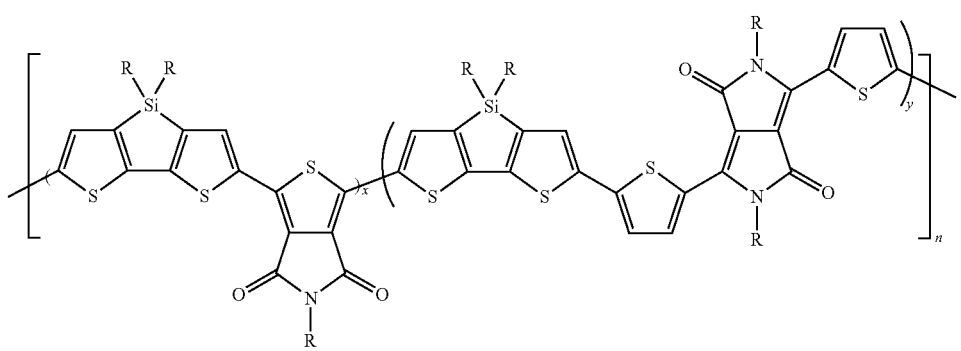

R: ethylhexyl

In a glove box, 4,4'-bis(2-ethylhexyl)-5,5'-bis(trimethyltin)dithieno[3,2-b:2',3'-d]silole (0.44 g, 0.60 mmol), 1,3-dibromo-5-(2-ethylhexyl)thieno[3,4-c]pyrrole-4,6-dione (0.12 g, 0.28 mmol), 2,5-diethylhexyl-3,6-bis(5-bromothiophen-2-yl)pyrrolo[3,4-c]-pyrrole-1,4-dione (0.19 g, 0.28 mmol), tris (dibenzylideneacetone)dipalladium(0) (0.014 g, 0.015 mmol) and tris(o-tolyl)phosphine (0.018 g, 0.059 mmol) were weighted out into a flame dried 50 mL Schlenk flask. Reaction flask was removed from the glove box and 8 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.38 g, 55%). Molecular weight was determined by GPC in chloroform (1 mL/min at 35° C.) vs. polystyrene standards: $M_n$=12,900, $M_w$=95,700, PDI=7.4.

Example 9 poly{(2,6'-4,8-diethylhexyloxybenzo[1,2-b;3,4-b]dithiophene-alt-(5-(2-ethylhexyl)thieno[3,4-c]pyrrole-4,6-dione)-alt-(2,6'-4,8-diethylhexyloxybenzo[1,2-b;3,4-b]dithiophene-alt-5-diethylhexyl-3,6-dithiophen-2-ylpyrrolo[3,4-c]pyrrole-1,4-dione)}

In a glove box, 2,6-bis(trimethyltin)-4,8-diethylhexyloxybenzo[1,2-b;3,4-b]dithiophene (0.4 g, 0.52 mmol), 1,3-dibromo-5-(2-ethylhexyl)thieno[3,4-c]pyrrole-4,6-dione (0.11 g, 0.26 mmol), 2,5-diethylhexyl-3,6-bis(5-bromothiophen-2-yl)pyrrolo[3,4-c]-pyrrole-1,4-dione (0.18 g, 0.26 mmol), tris (dibenzylideneacetone)dipalladium(0) (0.012 g, 0.013 mmol) and tris(o-tolyl)phosphine (0.016 g, 0.052 mmol) were weighted out into a flame dried 50 mL Schlenk flask. Reaction flask was removed from the glove box and 6 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.29 g, 67%). Molecular weight was determined by GPC in 1,3,5-trichlorobenzene (1 mL/min at 150° C.) vs. polystyrene standards: $M_n$=26,100, $M_w$=74,100, PDI=2.8.

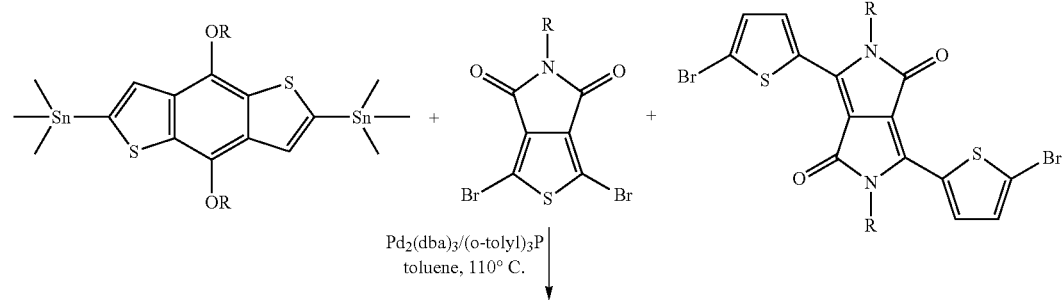

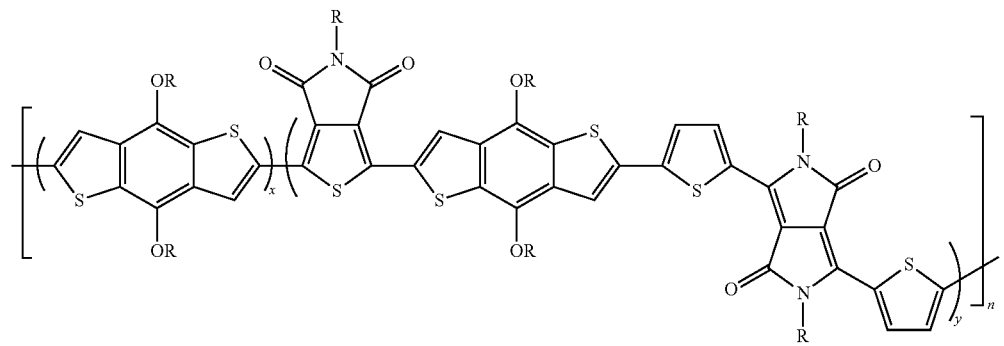

R: ethylhexyl

Example 10

Structure IIIG. poly{(4,4'-bis(2-ethylhexyl)dithieno[3,2-b:2',3'-d]silole-alt-5-(2-ethylhexyl)thieno[3,4-c]pyrrole-4,6-dione)-alt-(4,4'-bis(2-ethylhexyl)dithieno[3,2-b:2',3'-d]silole-alt-2-benzo[1,2,5]thiadiazole)}

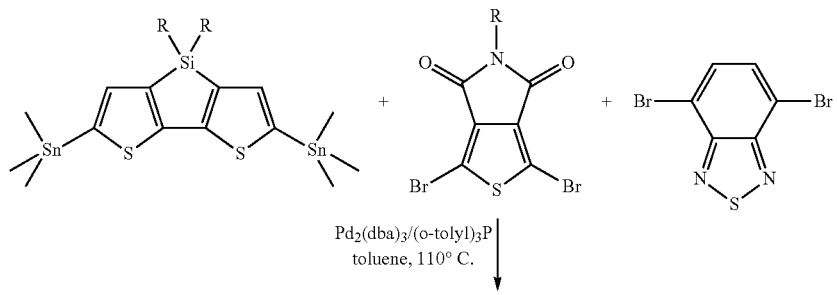

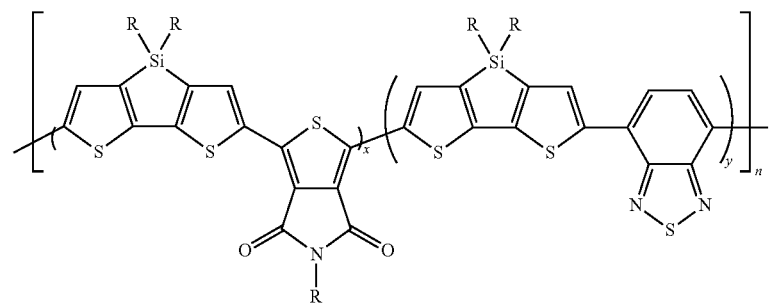

R: ethylhexyl

In a glove box, 4,4'-bis(2-ethylhexyl)-5,5'-bis(trimethyltin)dithieno[3,2-b:2',3'-d]silole (0.40 g, 0.54 mmol), 1,3-dibromo-5-(2-ethylhexyl)thieno[3,4-c]pyrrole-4,6-dione (0.11 g, 0.26 mmol), 4,7-dibromo-benzo[1,2,5]thiadiazole (0.075 g, 0.26 mmol), tris(dibenzylideneacetone)dipalladium(0) (0.012 g, 0.013 mmol) and tris(o-tolyl)phosphine (0.016 g, 0.053 mmol) were weighed out into a flame dried 50 mL Schlenk flask. Reaction flask was removed from the glove box and 7 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, and hexane. The hexanes fraction was passed through celite, to remove catalyst residuals, and solvent was removed under vacuum to yield a brown-copper colored polymer (0.15 g, 37%). Molecular weight was determined by GPC in chloroform (1 mL/min at 35° C.) vs. polystyrene standards: $M_n$=4,910, $M_w$=10,700, PDI=2.2.

Prophetic Examples

Example 11 (Prophetic)

General Procedure for the Synthesis of 4,8-diethylhexyloxybenzo[1,2-b;3,4-b]dithiophene-enriched poly{bis(2,6'-4,8-diethylhexyloxybenzo[1,2-b;3,4-b]dithiophene)-alt-(5-(2-ethylhexyl)thieno[3,4-c]pyrrole-4,6-dione} via Stille cross-coupling polymerization

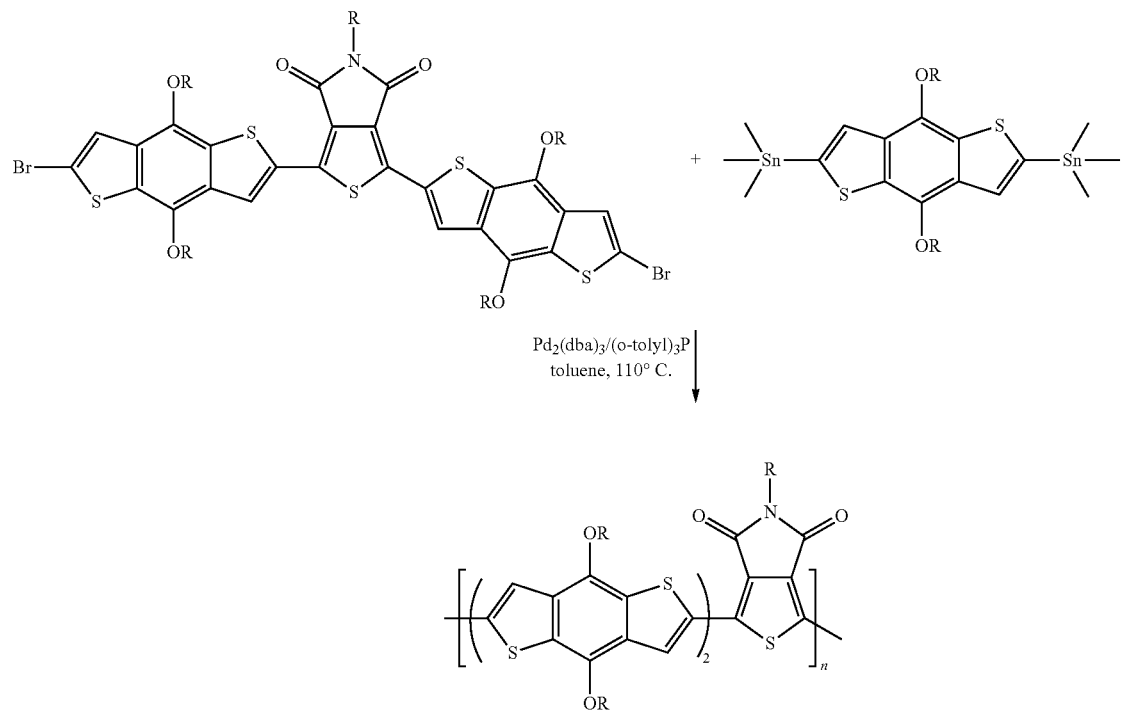

R: ethylhexyl

In a glove box, dibromo-(1,3-bis(4,8-diethylhexyloxybenzo[1,2-b;3,4-b]dithiophene)-5-(2-ethylhexyl)thieno[3,4-c]pyrrole-4,6-dione) (0.50 mmol), 2,6-bis(trimethyltin)-4,8-diethylhexyloxybenzo[1,2-b;3,4-b]dithiophene (0.50 mmol), tris(dibenzylideneacetone)dipalladium(0) (2.5 mol %) and tris(o-tolyl)phosphine (0.050 mmol) are charged into a flame dried 50 mL Schlenk flask. The reaction flask is removed from the glove box and 6 mL of deoxygenated toluene are added via syringe. The mixture is evacuated and refilled with argon five times. The reaction flask is immersed into a preheated to 110° C. oil bath and left stirring under an argon stream for 12 hours. The polymerization is quenched with 0.3 mL of 2-iodothiophene and stirred at 110° C. for additional two hours. The oil bath is removed and after cooling to room temperature, 40 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Hexanes and chloroform fractions are concentrated, re-precipitated in methanol, isolated via filtration, and analyzed by gel permeation chromatography (GPC) and NMR.

Furthermore, in addition to Example 11, a number of other complementary procedures based on transition metal-assisted/catalyzed cross-coupling reactions for the synthesis of alternating dioxopyrrolo-based donor-acceptor polymers that would preserve regular alternation of a monomer sequence in the polymer backbone can be successfully extended to many other organometallic species. Several exemplary synthetic schemes are presented below that involve the use of Grignard (Kumada cross-coupling; lit. ref.: Yamamoto, T.; Morita, A.; Miyazaki, Y.; Maruyama, T.; Wakayama, H.; Zhou, Z.-H.; Nakamura, Y.; Kanbara, T.; Sasaki, S.; Kubota, K. *Macromolecules* 1992, 25, 1214.; Scheme A) and/or organozinc (Negishi cross-coupling; lit. ref: Knochel, P.; Dohle, W.; Gommermann, N.; Kneisel, F. F.; Kopp, F.; Korn, T.; Sapountzis, I.; Vu, V. A.; Scheme B) reagents, and/or organitin intermediates (Woo, C. H.; Thompson, B. C.; Kim, B. J.; Toney, M. F.; Frechet, J. M. J. *J. Am. Chem. Soc.* 2008, 130, 16324.; Scheme C).

Scheme A. General synthetic scheme for the synthesis of 4,8-diethylhexyloxybenzo[1,2-b;3,4-b]dithiophene enriched poly{bis(2,6'-4,8-diethylhexyloxybenzo[1,2-b;3,4-b]dithiophene)-alt-(5-(2-ethylhexyl)thieno[3,4-c]pyrrole-4,6-dione} via Kumada cross-coupling polymerization

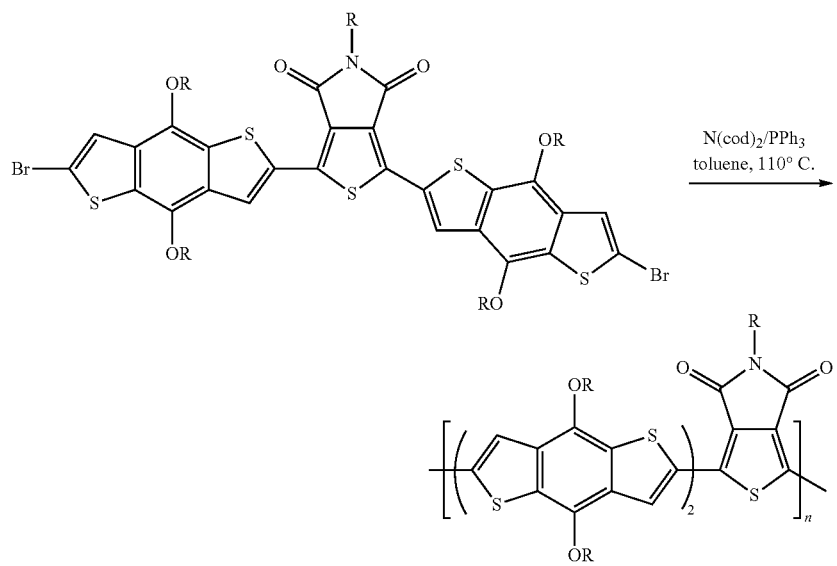
R: ethylhexyl
Scheme B. General procedure for the synthesis of 1,3-bis(4,8-diethylhexyloxybenzo[1,2-b;3,4-b]dithiophene)-5-(2-ethylhexyl)thieno[3,4-c]pyrrole-4,6-dione (top) and 4,8-diethylhexyloxybenzo[1,2-b;3,4-b]dithiophene enriched poly{bis(2,6'-4,8-diethylhexyloxybenzo[1,2-b;3,4-b]dithiophene)-alt-(5-(2-ethylhexyl)thieno[3,4-c]pyrrole-4,6-dione} (bottom) via Negishi cross-coupling reaction
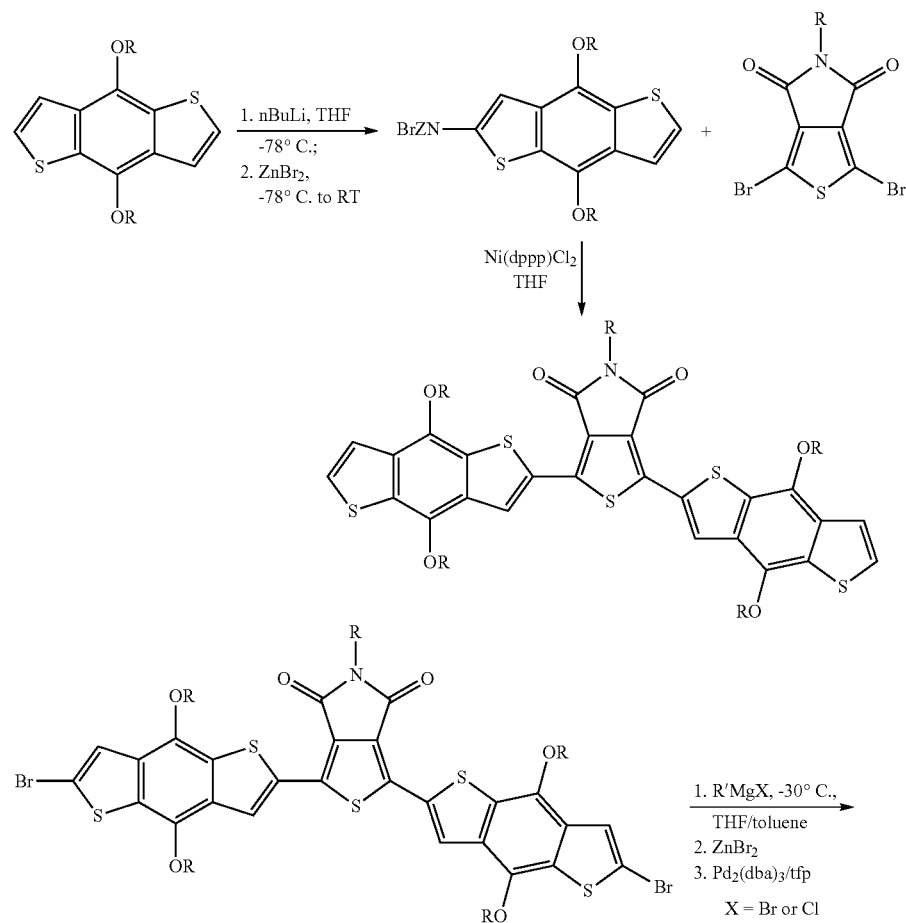

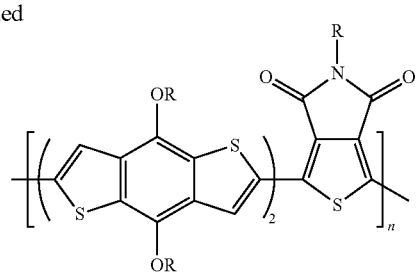

R: ethylhexyl

Scheme C. General procedure for the synthesis of 1,3-bis(4,8-diethylhexyloxybenzo[1,2-b;3,4-b]dithiophene)-5-(2-ethylhexyl)thieno[3,4-c]pyrrole-4,6-dione via Stille cross-coupling reaction

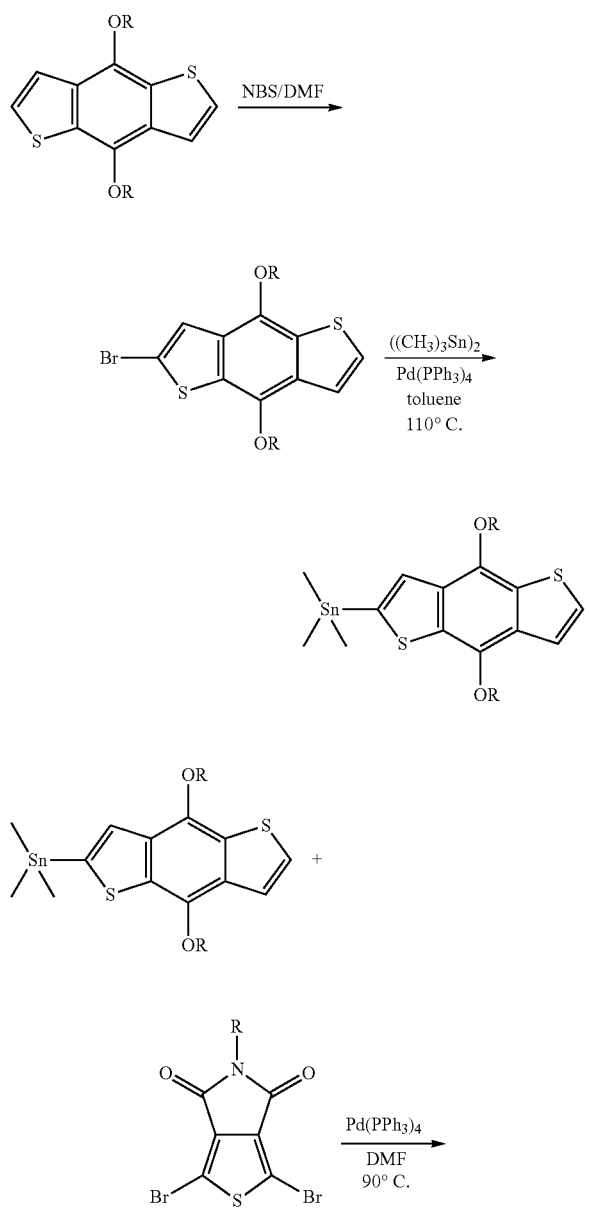

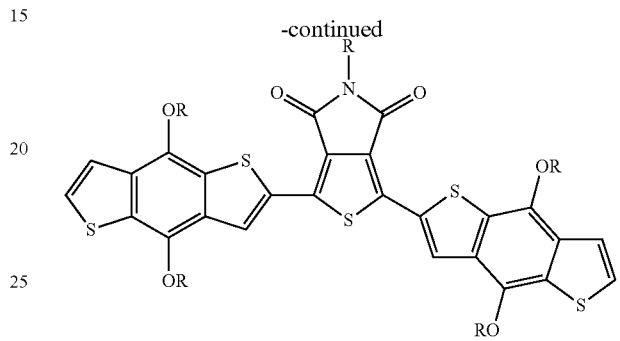

All polymer samples are precipitated in methanol, filtered, and purified by Soxhlet extractions utilizing successively methanol, acetone, hexanes, and chloroform and/or passing through a bed of celite. Hexanes and chloroform fractions are concentrated, re-precipitated in methanol, isolated via filtration, and analyzed by gel permeation chromatography (GPC) and NMR.

II. Testing of Polymers Including Device Fabrication and Testing

Figure 3:
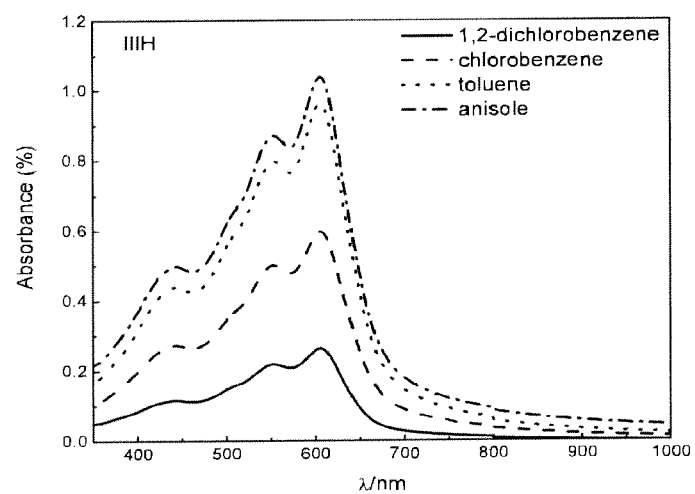
FIG. 3 shows absorption spectra for four films of donor-acceptor polymer prepared from four solutions with four different solvents (no n-type material).

FIG. 3. UV-Vis absorption profile of Polymer IIIH (Example 6) Donor-Acceptor polymer containing dioxypyrrolo-functionality in thin films spin cast from different solvents.

FIG. 3 shows the absorption spectrum for a series of films of Polymer IIIH/C60-PCBM (Example 6). The important observation in all of these films is the presence of vibronic structure which is indicative of a well-defined chromophore. While not limited by theory, this can result from the presence of strong oxygen-sulfur interactions that can help to rigidify and/or significantly planarize the donor-acceptor units thus reducing dihedral angles between the adjacent thiophene rings. This planarizing non-covalent binding interaction can serve to rigidify the chromophore which presumably helps to increase extinction due to increased packing density, charge transport and yield well-behaved photophysics (e.g., long exciton diffusion lengths and excited state lifetimes). Dihedral twisting is often a consequence of excited state relaxation. Elimination of such effect can yield the aforementioned improved chemico-physical properties. This vibronic structure effect can be seen in rigid chromophores like porphyrin and less so in semi-crystalline conjugated polymers like P3HT. The effect is believed to be non-existent or almost non-existent in most of amorphous D-A conjugated polymers synthesized in the prior art.

Fabrication of Solar Cell Devices Using Polymers and Fullerene Acceptors

Inks were formulated with a fullerene derivative acceptor and solvent.

Indium tin oxide ("ITO") coated glass substrates were purchased from Thin Film Devices ("TFD", Anaheim, Calif.). These substrates were cleaned in a Class 10,000 clean room by sonicating for 20 min in a soap solution, followed by 20 min of sonication in water, 20 min of sonication in acetone and 20 min of sonication in IPA. Finally the substrates were exposed to UV ozone (300 W) for 10 min. After cleaning, each substrate was then coated with a ~30 nm thick layer of Baytron AI4083 (H.C Stark) by spin coating for 5 seconds at 400 rpm in air, followed by a 1 minute at 6000 rpm. The devices were then transferred to a $N_2$ atmosphere glovebox and annealed on a hot plate at 175° C. for 30 min.

The active layer was then spin-coated on top of the PEDOT:PSS layer on a Headway spinner at spin speeds ranging from 300-1000 rpm to obtain the required active layer thickness. The active layer films were either allowed to dry in the glovebox or were annealing on the hot plate to dry. Finally, after annealing, the cathode was vapor deposited from a base pressure of ~$7\times10^{-7}$. In all of the following working examples, the cathode for the devices was a bilayer of Ca (25 nm) and Al (200 nm). The Ca and Al were deposited at rates of 0.3 A/s and 4 A/s respectively. The devices were then encapsulated via a glass cover slip (blanket) encapsulation sealed with EPO-TEK OG112-4 UV curable glue. The encapsulated device was cured under UV irradiation (80 mW/cm$^2$) for 4 minutes and tested as follows.

The photovoltaic characteristics of devices under white light exposure (Air Mass 1.5 Global Filter) were measured using a system equipped with a Keithley 2400 source meter and an Oriel 300 W Solar Simulator based on a Xe lamp with output intensity of 100 mW/cm$^2$ (AM1.5G). The light intensity was set using an NREL-certified Si-KG5 silicon photodiode.

Power Conversion Efficiency Determinations

Devices were prepared as described above were tested using an Oriel Solar Simulator and the voltage was swept from reverse to forward bias. From the resulting current that was measured, the power conversion efficiency of each device was determined. Data for each device are summarized in Table 1 as well as relevant processing parameters for each device.

TABLE 2

Comparison in Absorption coefficients, Alpha, for poly(3-hexylthiophene) and Donor-Acceptor polymers comprising dioxypyrrolo-functionality

| Polymer | Abs | b (cm) | b (nm) | Alpha* (cm$^{-1}$) |
|---|---|---|---|---|
| P3HT | 0.270 | $6.40 \times 10^{-6}$ | 64 | $0.97 \times 10^5$ |
| Ex. 9 | 0.196 | $2.25 \times 10^{-6}$ | 22 | $2.01 \times 10^5$ |
| Ex. 6 | 0.409 | $5.70 \times 10^{-6}$ | 57 | $1.65 \times 10^5$ |

*$\alpha = 2.3 \times Abs_{(at\ \lambda max)}/b_{(film\ thickness\ in\ cm)}$ [in thin films]

The new polymers exhibit approximately 2× increase in absorptivity (based on alpha) vs. P3HT suggesting more planar structure, dense/small interchain distance that could result in increase in $J_{SC}$ and, thus, superior OPV performance (P3HT is poly(3-hexylthiophene)).

Figure 4:
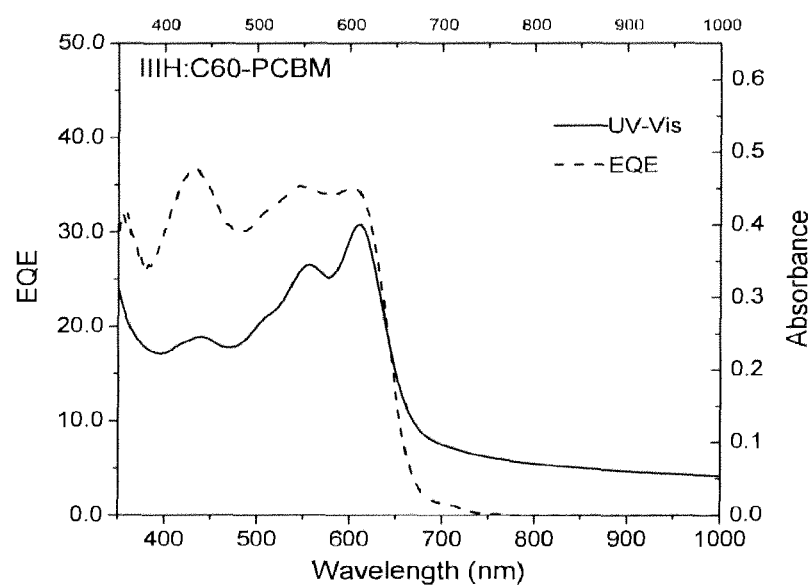
FIG. 4 shows EQE and absorption spectra for donor-acceptor polymer (Example 6) mixed with n-type material (C60 derivative) in a photovoltaic device active layer.

FIG. 4: Comparison of absorption and EQE spectra of device with III-H:C60-PCBM blend. It is evident from the data that the devices based on III-H (Ex. 6) exhibit a relatively broad response range covering from about 400 nm to about 650 nm. The absorption is relatively flat without substantial gaps.

Figure 5:
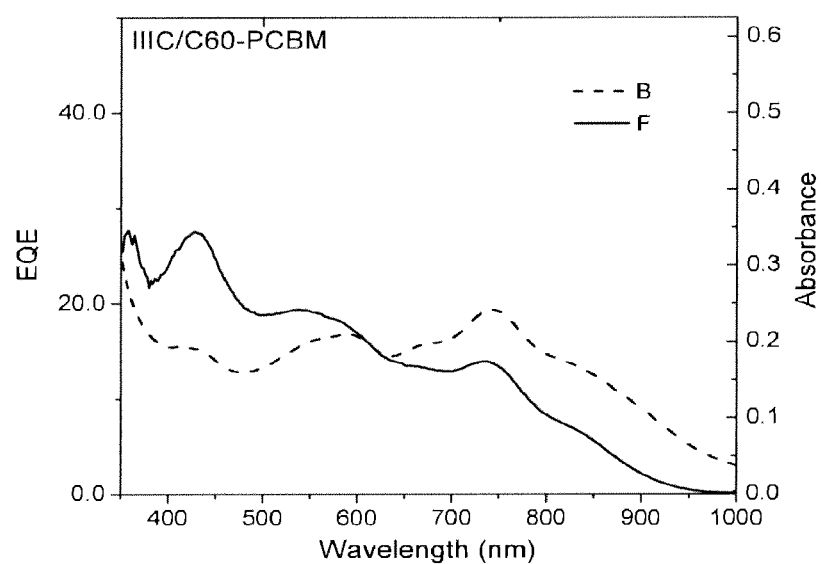
FIG. 5 shows EQE and absorption spectra for donor-acceptor polymer (Example 9) mixed with n-type material (C60 derivative) in a photovoltaic device active layer.

FIG. 5: Comparison of absorption and EQE spectra of device with III-C:C60-PCBM blend (Ex. 9 is Structure III-C). The absorption is broader into the red region compared to FIG. 4.

Part III: Additional Working and Prophetic Examples

Diketopyrrole monomers can be made according to known procedures, and procedures adapted therefrom, from the literature. See, for example, Peet, J.; Tamayo, A. B.; Dang, X.-D.; Seo, J. H.; Nguyen, T.-Q. *Appl. Phys. Lett.*, 2009, 93, 163306; Janssen et al. *Adv. Mater.*, 2008, 20, 2556; Zhu, Y. Ph.D. Dissertation, University of Koln, Germany, 2006; Yang et al. *J. App. Polymer Sci.* 2009, 111, 1976; EA00962499A2; EB0094911B1; EB00133156B1; EB00181290B1; EB00302018B1; EB00672729B1; EB 00962499B2; Tamayo et al., *J. Phys. Chem. C.*, 2008, 17402; Boens et al. *Int. J. Photoenergy* 2004, V6, 159; Lunak et al., *J. Fluoresc. Chem.* 2008, 18, 1181; Tamayo et al. *App. Phys. Lett.* 2009, 94, 103301; Tamayo et al., *J. Phys. Chem. C*, 2008, 112, 11545; U.S. Pat. Nos. 4,585,878B1; 4,778,899B1; 4,921,566B1; WO08000664A1; Burgi, L; Turbiez, M.; Pfeiffer, R.; Bienewald, F.; Kirner, H.-J.; Winnewisser, C. *Adv. Mater.*

TABLE 1

Photovoltaic Performance of single layer OPVs based on Donor-Acceptor polymers comprising dioxypyrrolo-functionality.

| Polymer | N-type | P:N ratio | Solvent (volume solids) | Drying Conditions | Jsc (mA/cm$^2$) | Voc (V) | FF | PCE (%) |
|---|---|---|---|---|---|---|---|---|
| Ex. 6 | C70-PCBM | 1:1 | dichlorobenzene (0.0157) | No anneal | 8.11 | 0.78 | 0.57 | 3.6 |
| Ex. 9 | C70-PCBM | 1:4 | trichlorobenzene (0.011) | Anneal at 60° C. for 18 minutes | 10.12 | 0.69 | 0.53 | 3.6 |

2008, 20, 2217; Derong Cao, D.; Liu, Q.; Zeng, W.; Han, S.; Peng, J.; Liu, S. *J. Polymer Sci., Part A* 2006, 44, 2395.

Working Example 12

Synthesis of 8-(2-ethylhexoxy)-4-(2-ethylhexyl)thieno[2,3-f]benzothiophene

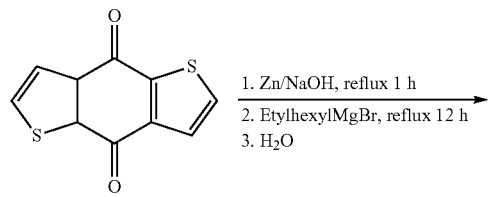

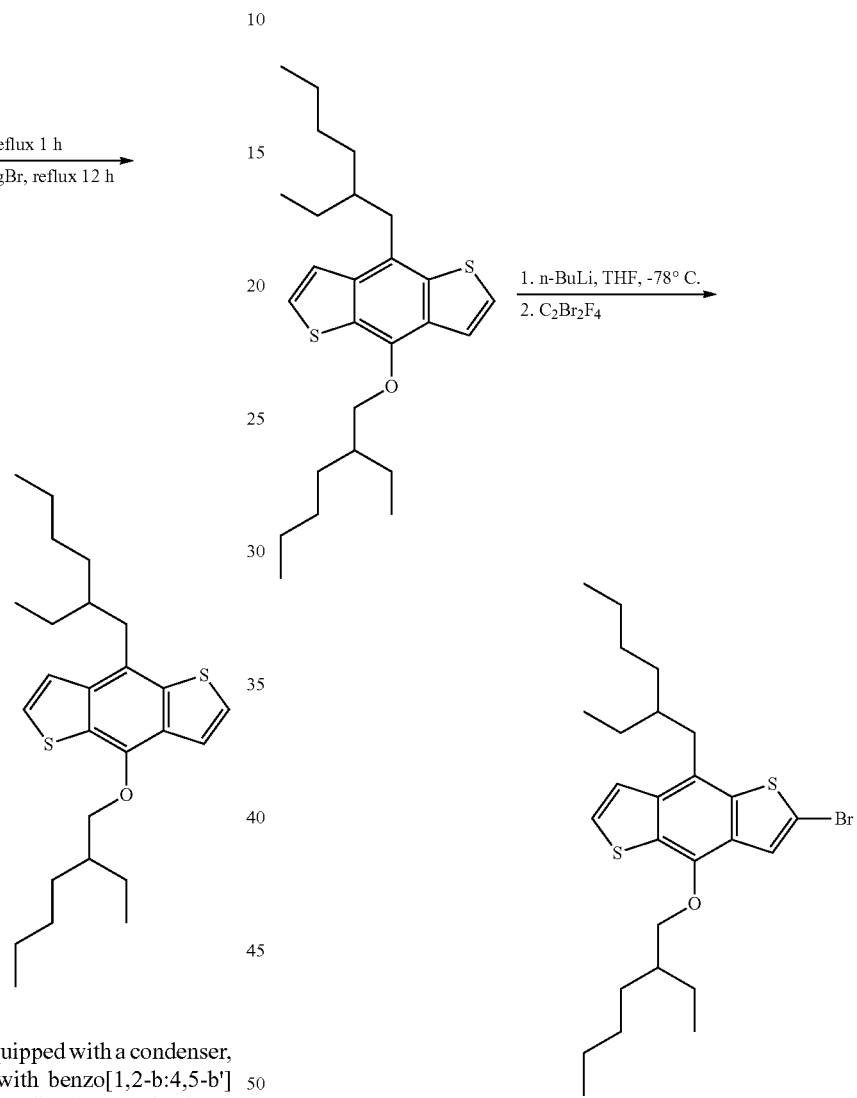

A dry 500-mL three-neck flask, equipped with a condenser, was flushed with $N_2$ and charged with benzo[1,2-b:4,5-b']dithiophene-4,8-dione (22.0 g, 0.10 mol), zinc powder (14.4 g, 0.22 mol), sodium hydroxide (NaOH) (30 g, 1.5 mol), and water (330 mL, 0.3 M). The reaction flask was heated to reflux for 1 hour, followed by addition of ethylhexyl bromide (53.3 mL, 0.30 mol) and stirring continued for additional 1 hour at reflux. The reaction was monitored by TLC that indicated a slow conversion, thus double amounts of zinc powder and ethylhexyl bromide were added. The reaction was left stirring at reflux for additional 12 hours. The heating was stopped and the reaction mixture was allowed to warm to ambient temperature, and stirring continued for another 12 hours. As the reaction was completed, the reaction mixture was poured into 300 mL of water and extracted with MTBE (200 mL) three times. The combined organic layer was washed with water two times and dried over anhydrous magnesium sulfate ($MgSO_4$). After the product was filtered, the solvent was removed by rotary evaporation. The product was purified using column chromatography on silica gel with hexanes/chloroform (gradient) to yield yellow oil with yields ranging between 70 and 80%.

Working Example 13

Synthesis of 6-bromo-8-(2-ethylhexoxy)-4-(2-ethylhexyl)thieno[2,3-f]benzothiophene

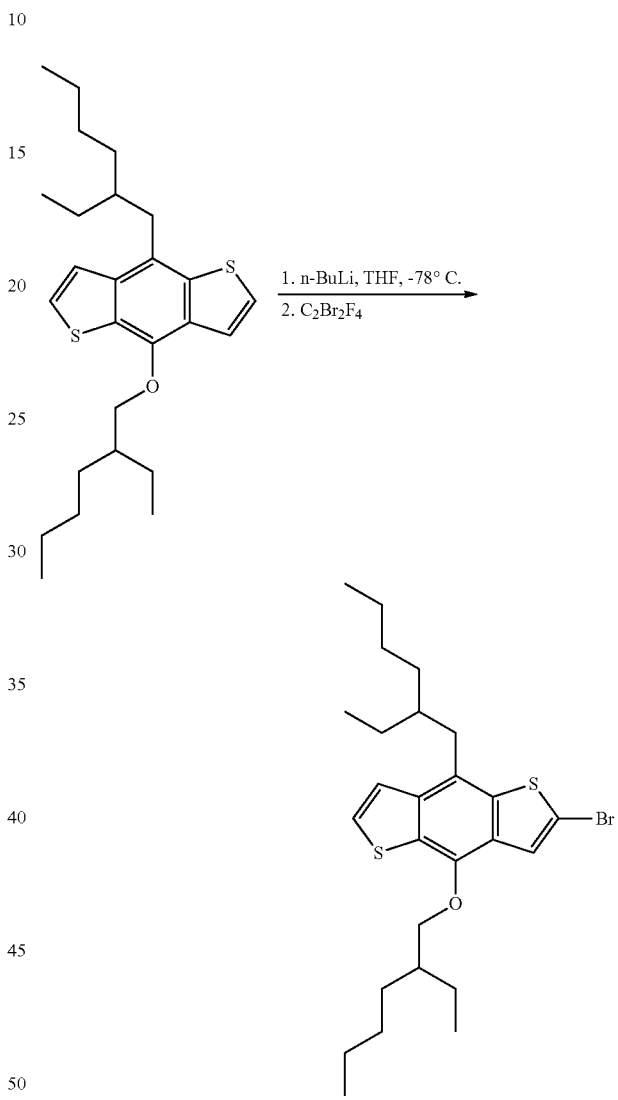

A dry 500-mL three-neck flask was flushed with $N_2$ and was charged with 8-(2-ethylhexoxy)-4-(2-ethylhexyl)thieno[2,3-f]benzothiophene (8.4 g, 0.020 mol) and THF (200 mL, 0.1 M) via deoxygenated syringe. The reaction flask was cooled to −78° C. and a 2.0 M solution of n-butyllithium in hexanes (10 mL, 0.020 mol) was added dropwise via deoxygenated syringe. After 30 minutes of stirring at −78° C., dibromotetrafluoroethane (7.8 g, 0.030 mol) was added to the reaction flask and stirring continued for 1 hour at −78° C. The cooling bath was removed and the reaction mixture was allowed to warm up to ambient temperature. As the reaction was completed, cool DI water (50 mL) was slowly added to the reaction flask. Then, the reaction mixture was poured into 150 mL of cool water and extracted with hexanes (200 mL) three times. The combined organic layer was dried over anhydrous magnesium sulfate (MgSO₄). After the product was filtered, the solvent was removed by rotary evaporation. The product was purified using column chromatography on silica gel with hexanes/chloroform (gradient) to yield colorless oil (4.2 g, 42%).

Spectral data: ¹H NMR (300 MHz, CDCl₃): $\delta_H$ 7.46 (s, 1H), 7.38 (s, 1H), 4.15 (s, 2H), 2.9 (s, 2H), 1.14-1.95 (bm, 18H), 0.78-1.08 (bm, 12H).

Working Example 14

Synthesis of 4-(2-ethylhexoxy)-8-(2-ethylhexyl)thieno[2,3-f]benzothiophene-2-carbonitrile

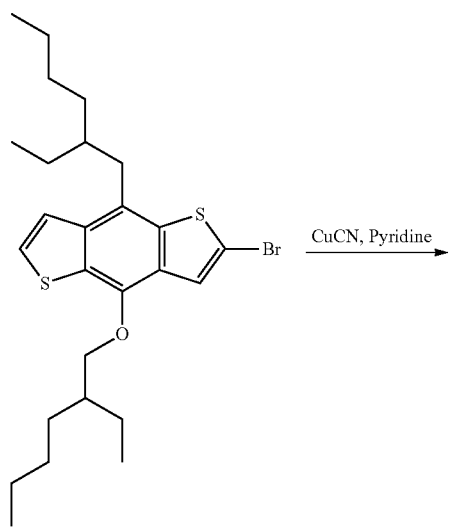

A dry 100-mL three-neck flask, equipped with a condenser, charged with 6-bromo-8-(2-ethylhexoxy)-4-(2-ethylhexyl)thieno[2,3-f]benzothiophene (4.2 g, 8.2 mmol) and flushed with N₂. Deoxygenated pyridine (15 mL, 0.5 M) was then added via syringe. Copper (I) cyanide (2.2 g, 25 mmol) was added to the reaction flask and the mixture was evacuated and refilled with nitrogen three times. The reaction flask was heated to reflux for 48 hours. As the reaction was completed, the reaction mixture was poured into 50 mL of water and extracted with MTBE (50 mL) three times. The combined organic layer was washed with water two times and dried over anhydrous magnesium sulfate (MgSO₄). After the product was filtered, the solvent was removed by rotary evaporation. The product was purified using column chromatography on silica gel with hexanes/ethyl acetate (gradient) to yield oil (1.4 g, 38%).

Working Example 15

Synthesis of 4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione

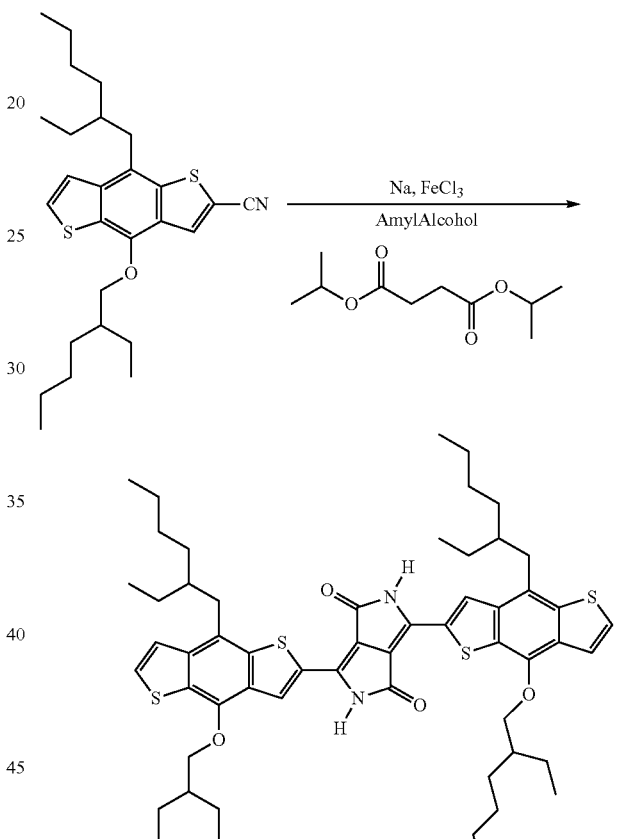

A dry 100-mL three-neck flask, equipped with an addition funnel, a condenser, and a thermometer, was charged with sodium (0.13 g, 5.6 mmol), t-amyl alcohol (3 mL), and flushed with N₂. A catalytic amount of anhydrous FeCl₃ was added and the reaction solution was heated to 90° C. until the sodium metal completely dissolved. The reaction was allowed to cool down to 50° C. and 4-(2-ethylhexoxy)-8-(2-ethylhexyl)thieno[2,3-f]benzothiophene-2-carbonitrile (1.3 g, 2.8 mmol) was added to the flask. The reaction mixture was warmed back to 90° C. followed by addition of diisopropyl succinate (0.29 g, 1.4 mmol) in 5 mL of t-amyl alcohol which was added dropwise over 1 hour. The reaction was stirred for another 20 hours at 90° C. and cooled to 50° C. Acetic acid (5 mL) was slowly added to the reaction flask and the reaction was briefly heated to reflux and then cooled down. The reaction mixture was filtered by vacuum. The residue was redispersed in hot methanol, collected, washed several times with hot methanol and water, and dried. The final product yields ranged between 70 and 80%.

Working Example 16

Alkylation of 4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione

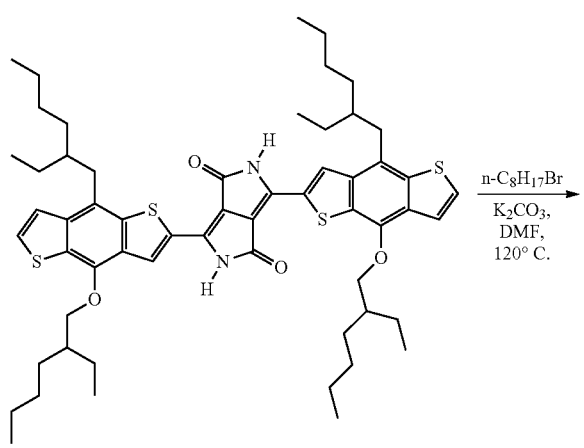

A dry 100-mL three-neck flask, equipped with a condenser, charged with 4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione (1.0 g, 1.0 mmol), anhydrous potassium carbonate ($K_2CO_3$) (0.55 g, 4.0 mmol), and flushed with $N_2$. Anhydrous N,N-dimethylformamide (10 mL, 0.1 M) was then added via syringe. The reaction flask was heated to 120° C. for 1 hour. N-octyl bromide (0.58 g, 3.0 mmol) was added and the reaction mixture was left stirring at 130° C. for 12 hours. As the reaction was completed, the reaction mixture was cooled down to ambient atmosphere, then poured into vigorously stirring 50 mL of water and stirred for 2 hours. The reaction residue was extracted with MTBE (50 mL) three times. The combined organic layer was washed with water/methanol two times and dried over anhydrous magnesium sulfate ($MgSO_4$). After the product was filtered, the solvent was removed by rotary evaporation. The product was purified using column chromatography on silica gel with hexanes/ethyl acetate (gradient) with yields ranging between 70 and 80%.

Prophetic Examples

Example 17 (Prophetic)

Bromination of 4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione

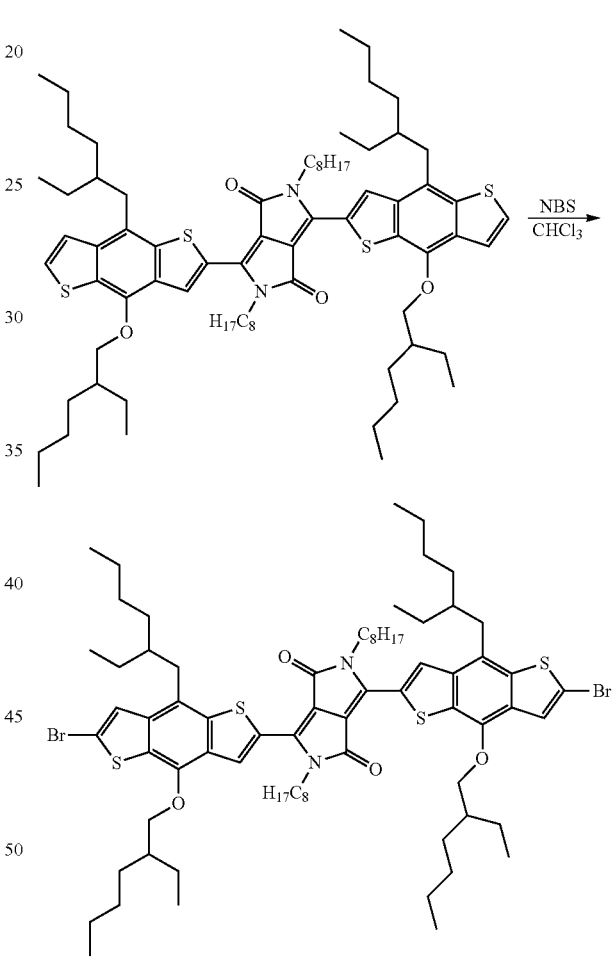

A dry 100-mL three-neck flask is charged with bis-alkylated-4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione (0.5 mmol) and flushed with $N_2$. Anhydrous chloroform (0.3 M) is added to the reaction flask via syringe followed by addition of N-bromosuccinimide (1.1 mmol). The reaction flask is covered with aluminum foil and left stirring for 12 hours at ambient temperature under nitrogen. The reaction is then poured into methanol and stirred for 1 hour. The residue is collected and purified.

Example 18 (Prophetic)

General Procedure for the Synthesis of Alternating Copolymers Via Stille Cross-Coupling Polymerization

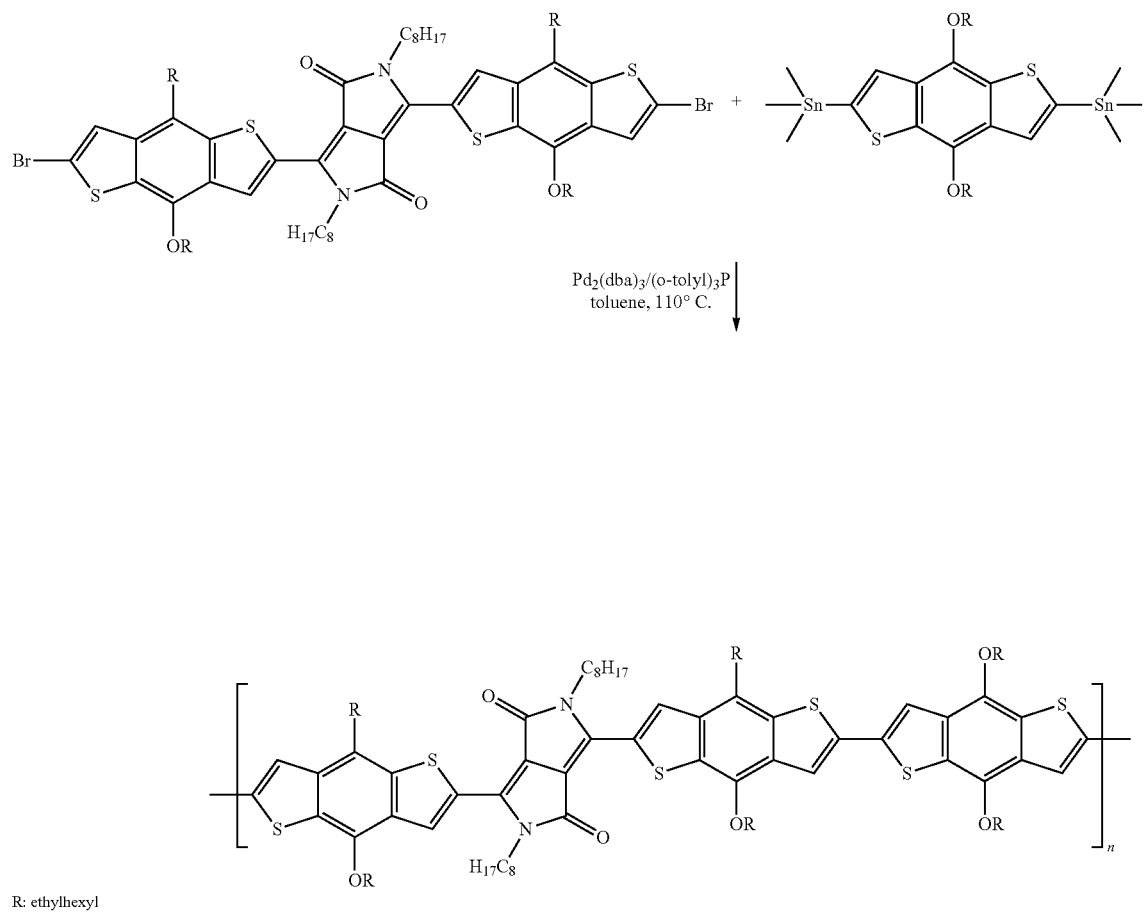

R: ethylhexyl

In a glove box, dibromo-4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione (0.50 mmol), 2,6-bis(trimethyltin)-4,8-diethylhexyloxybenzo[1,2-b;3,4-b]dithiophene (0.50 mmol), tris(dibenzylideneacetone)dipalladium(0) (2.5 mol %) and tris(o-tolyl)phosphine (0.050 mmol) are charged into a flame dried 50 mL Schlenk flask. The reaction flask is removed from the glove box and 6 mL of deoxygenated toluene are added via syringe. The mixture is evacuated and refilled with argon five times. The reaction flask is immersed into a preheated to 110° C. oil bath and left stirring under an argon stream for 12 hours. The polymerization is quenched with 0.3 mL of 2-iodothiophene and stirred at 110° C. for additional two hours. The oil bath is removed and after cooling to room temperature, 40 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Hexanes and chloroform fractions are concentrated, re-precipitated in methanol, isolated via filtration, and analyzed by gel permeation chromatography (GPC) and NMR.

Example 19 (Prophetic)

Furthermore, a number of other complementary procedures based on transition metal-assisted/catalyzed cross-coupling reactions for the synthesis of alternating dioxopyrrolo-based donor-acceptor polymers that would preserve regular alternation of a monomer sequence in the polymer backbone can be successfully extended to many other organometallic species. Several prophetic synthetic schemes are presented below that involve the use of Grignard (Kumada cross-coupling; lit. ref.: Yamamoto et al., Macromolecules 1992, 25, 1214.; Scheme A) and/or organozinc (Negishi cross-coupling; lit. ref: Knochel, P. et al.; Scheme B) reagents, and/or organitin intermediates (Woo et al., J. Am. chem. Soc. 2008, 130, 16324.; Scheme C).

Scheme A. General Synthetic Scheme for the Synthesis of Alternating Copolymers Via Kumada Cross-Coupling Polymerization
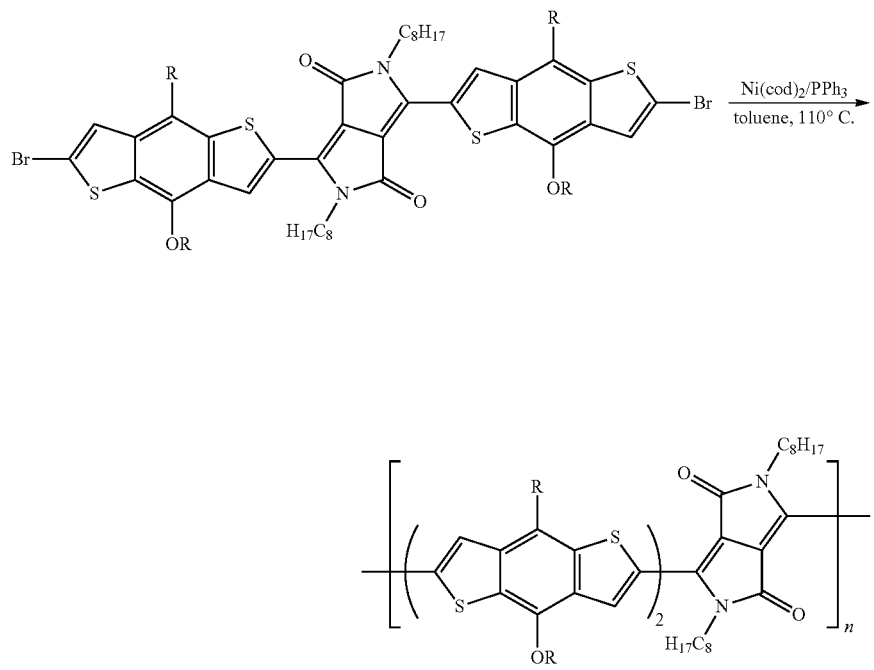
R: ethylhexyl
Scheme B. General Procedure for the Synthesis of Alternating Copolymers Via Negishi Cross-Coupling Reaction
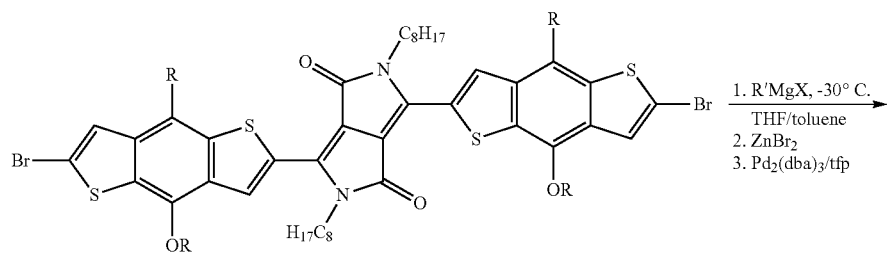
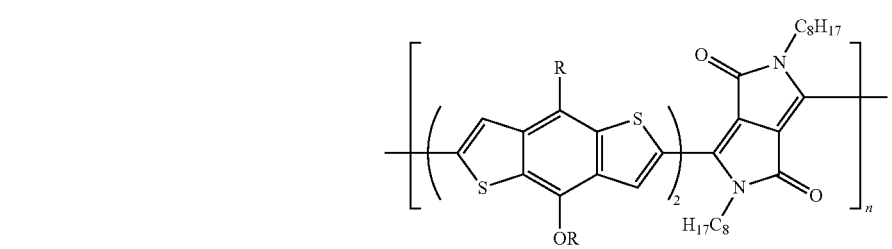
R: ethylhexyl
X = Br or Cl

Example 20 (Prophetic)

General Procedure for the Synthesis of Alternating Copolymers Via Stille Cross-Coupling Polymerization

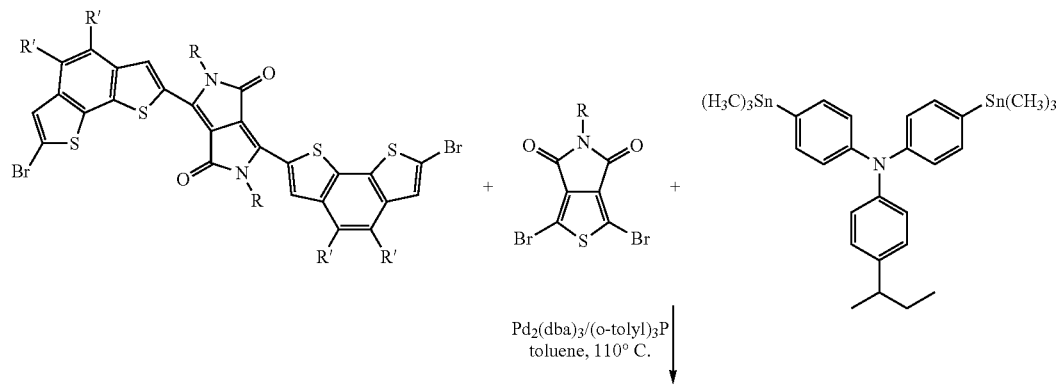

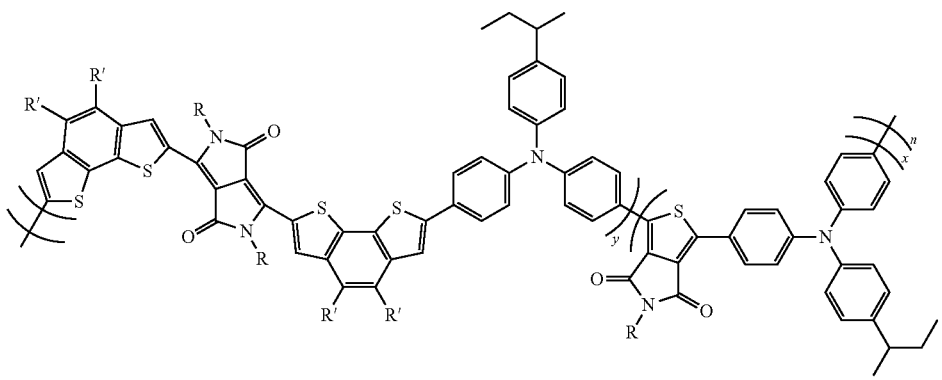

R': ethylhexyl
R: n-C$_8$H$_{17}$

In a glove box, dibromo-1,4-bis[4,5-bis(2-ethylhexyl)thieno[3,2-g]benzothiophen-2-yl]-2,5-dioctyl-pyrrolo[3,4-c]pyrrole-3,6-dione (0.50 mmol), 1,3-dibromo-5-(n-octyl)thieno[3,4-c]pyrrole-4,6-dione (0.50 mmol), N-(4-sec-butylphenyl)-4-trimethylstannyl-N-(4-trimethylstannylphenyl)aniline (1.0 mmol), tris(dibenzylideneacetone)dipalladium(0) (2.5 mol %) and tris(o-tolyl)phosphine (0.050 mmol) are charged into a flame dried 50 mL Schlenk flask. The reaction flask is removed from the glove box and 15 mL of deoxygenated toluene are added via syringe. The mixture is evacuated and refilled with argon five times. The reaction flask is immersed into a pre-heated to 110° C. oil bath and left stirring under an argon stream for 12 hours. The polymerization is quenched with 0.3 mL of 2-iodothiophene and stirred at 110° C. for additional two hours. The oil bath is removed and after cooling to room temperature, 15 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Hexanes and chloroform fractions are concentrated, re-precipitated in methanol, isolated via filtration, and analyzed by gel permeation chromatography (GPC) and NMR.

All polymer samples are precipitated in methanol, filtered, and purified by Soxhlet extractions utilizing successively methanol, acetone, hexanes, and chloroform and/or passing through a bed of celite. Hexanes and chloroform fractions are concentrated, re-precipitated in methanol, isolated via filtration, and analyzed by gel permeation chromatography (GPC) and NMR.

Inks, Solutions, and Devices

Inks, solutions, and photovoltaic devices are prepared and tested by methods described herein.

PART IV: ADDITIONAL EMBODIMENTS

PART IVA:

A synthetic scheme is provided for preparing a moiety to build into a polymer backbone.

Example

Synthesis of 2,6-Dibromo-4,8-bis(3-ethylheptyl)benzo[1,2-b:4,5-b']dithiophene

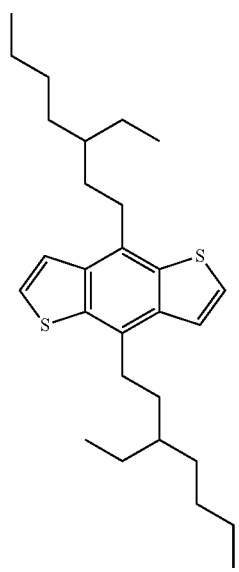
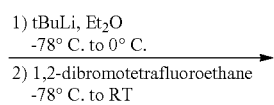

A dry 500-mL three-neck flask was flushed with $N_2$ and was charged with 4,8-bis(3-ethylheptyl)benzo[1,2-b:4,5-b']dithiophene (5.9 g, 0.013 mol) and diethyl ether ($Et_2O$) (133 mL, 0.1 M) via deoxygenated syringe. The reaction flask was cooled to −78° C. and a 1.3 M solution of tert-butyllithium in hexanes (28 mL, 0.036 mol) was added dropwise via deoxygenated syringe. After 30 minutes of stirring at −78° C., the solution was chilled to 0° C. and stirring was continued for 5 minutes, at which point the reaction mixture was chilled back to −78° C. 1,2-dibromotetrafluoroethane (6.3 mL, 0.053 mol) was added to the reaction flask dropwise and stirring continued for 30 minutes at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with MTBE (150 mL) three times. The combined organic layer was washed with water two times and dried over anhydrous magnesium sulfate ($MgSO_4$). After the product was filtered, the solvent was removed by rotary evaporation. The crude product was purified by Silica column chromatography using hexanes to yield a yellow solid (7.0 g, 88%).

$^1$H NMR (300 MHz, $CDCl_3$): $\delta_H$ 7.39 (s, 2H), 3.0-2.9 (m, 4H), 1.7-1.6 (m, 4H), 1.5-1.3 (m, 18H), 1.0-0.9 (t, 12H).

Example

Synthesis of 6-bromo-4,8-bis(3-ethylheptyl)benzo[1,2-b:4,5-b']dithiophene-2-carbonitrile

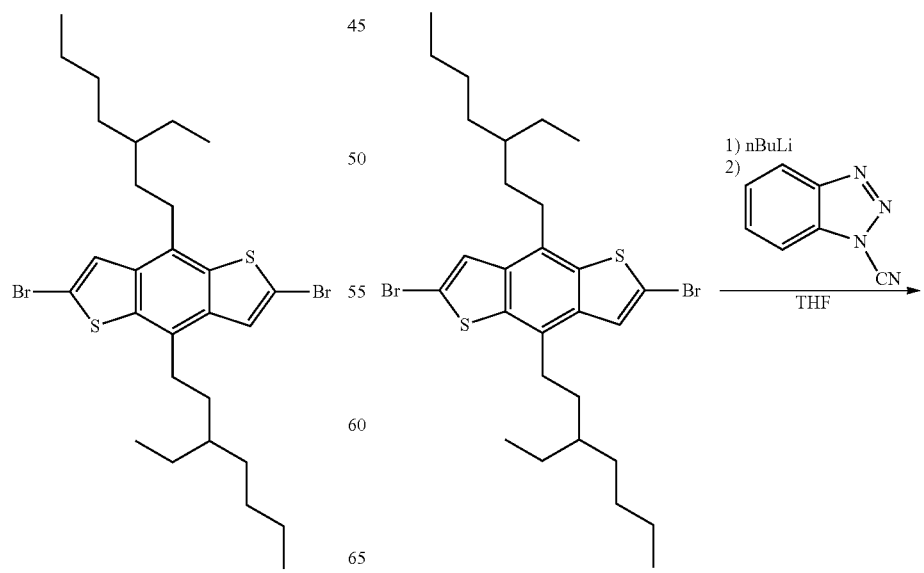

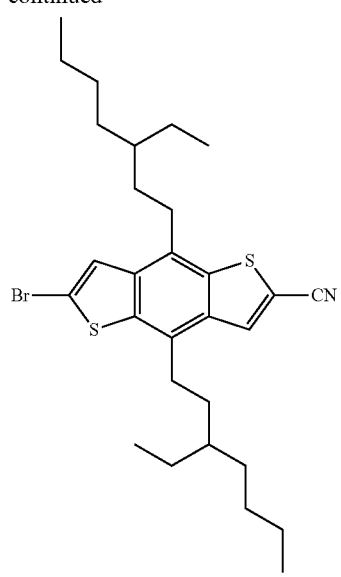

2,6-dibromo-4,8-bis(1-ethylheptyl)benzo[1,2-b:4,3-b']dithiophene (6.7 g, 0.011 mol) was dissolved in 56 mL dry THF and cooled to −78° C. A 2.1 M solution of n-BuLi (5.2 mL) in hexanes was added drop-wise and the reaction was monitored for completion. The suspension was then transferred into another flask containing 1-cyanoimidazole (2.07 g, 0.022 mol) dissolved in THF and pre-cooled to −78° C. The reaction was monitored by TLC and when complete, the reaction mixture was poured into a saturated ammonium chloride solution and stirred for 30 min. The mixture was extracted with MTBE and the organic layers dried over MgSO$_4$. The solvent was evaporated and the crude product was purified by column chromatography (75%).

Prophetic Example

Synthesis of 3,6-bis(6-bromo-4,8-bis(3-ethylheptyl)benzo[1,2-b:4,5-b']dithiophen-2-yl)pyrrolo[3,4-c]pyrrole-1,4(2H,5H)-dione

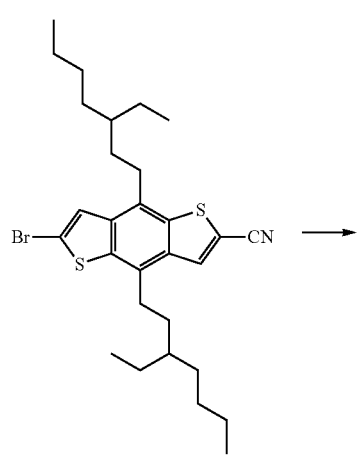 →

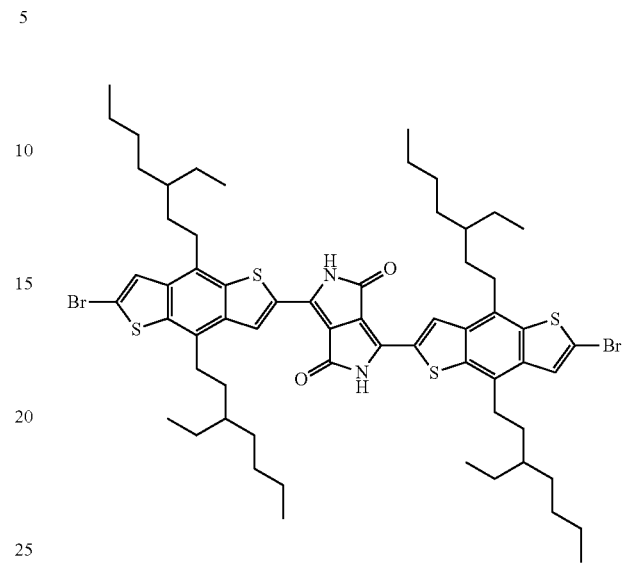

Sodium metal (0.71 g, 0.031 mol) and amyl alcohol (20 mL) are added to a 100 mL 3 neck flask with an attached thermometer and reflux condenser. A catalytic amount of FeCl$_3$ is added and the mixture is set to 90° C. until the sodium is completely melted. The mixture is cooled to 50° C. and the nitrile is added portion-wise (0.015 mol). The mixture is again warmed to 90° C. and a solution of amyl alcohol (5 mL) and isopropyl succinate (1.17 mL) are added over 30 min by a syringe pump. The reaction is stirred at 90° C. overnight and then cooled to 50° C. Glacial acetic acid (20 mL) is added to the flask and the mixture is set back to reflux for 30 min. After cooling to RT, the reaction is diluted with water and the product is extracted with MTBE. Combined organic fractions are dried over anhydrous MgSO$_4$, filtered, and solvent is removed by rotary evaporation. The product is purified by column chromatography.

Prophetic Example

Synthesis of 3,6-bis(6-bromo-4,8-bis(3-ethylheptyl)benzo[1,2-b:4,5-b']dithiophen-2-yl)-2,5-bis(2-ethylhexyl)pyrrolo[3,4-c]pyrrole-1,4(2H,5H)-dione

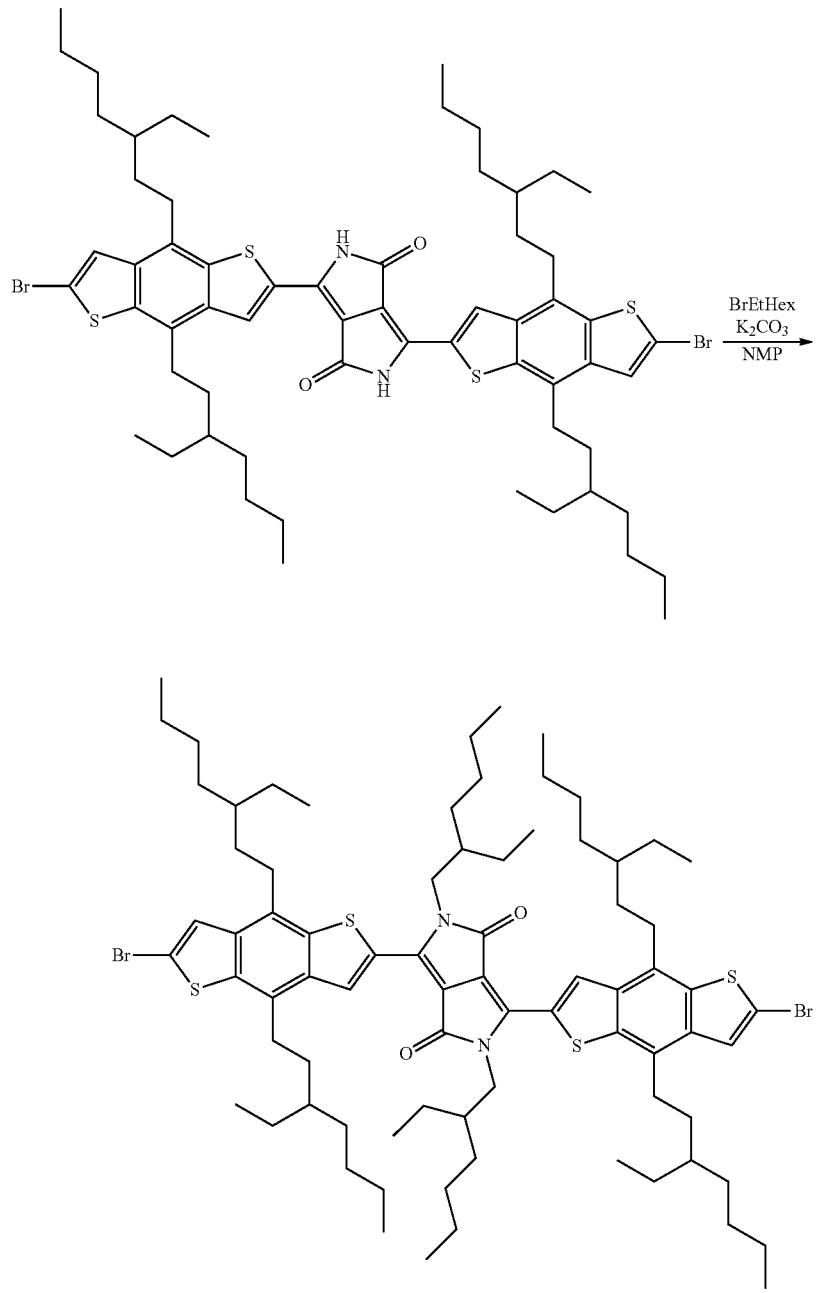

An oven dried 100 mL flask is charged with 3,6-bis(6-bromo-4,8-bis(3-ethylheptyl)benzo[1,2-b:4,5-b']dithiophen-2-yl)pyrrolo[3,4-c]pyrrole-1,4(2H,5H)-dione (0.0017 mol), $K_2CO_3$ (0.005 mol), and 20 mL of NMP. The mixture is warmed to 120° C. for 1 hour. 2-Ethylhexylbromide is added drop-wise to the reaction flask and stirred at 120° C. for 12 hours. The mixture is cooled to room temperature, poured into water, and followed by extraction with $CHCl_3$. The combined organic layers are dried over $MgSO_4$, filtered, and solvent removed by rotary evaporation. The product is purified by column chromatography with a hexanes:$CHCl_3$ (1:1) mixture.

The monomer can be incorporated into polymer structures as described herein.

PART IVB:

In part IVB, reference is made to cofiled application Ser. No. 12/874,137 filed Sep. 1, 2010, assigned to Plextronics, Sheina et al., which is hereby incorporated by reference ("Organic Electronic Devices and Polymers, including Photovoltaic Cells and Diketone-Based Polymers"), which is hereby incorporated by reference.

The structure described herein as (I) can be linked to itself to form larger structures such as (I)-(I) or (I)-(I) or (I)-(I)-(I). The side group R can be the same or different as (I) is linked to itself. These can be used as acceptors in the donor-acceptor polymers.

For example, other groups which can be included in monomers, oligomers, and polymers include:

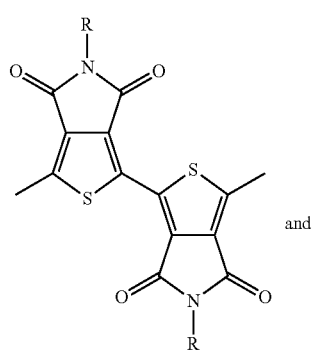

PP-1 and

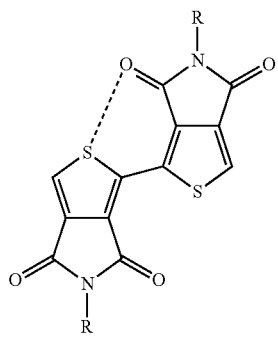

PP-2, showing an interaction between oxygen and sulfur, wherein R can be a solubilizing group as described herein,

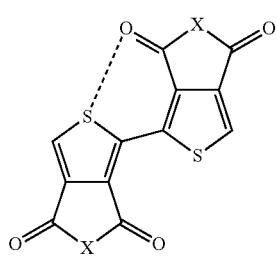

PP-3, wherein X can be, for example, nitrogen, a bivalent carbon, or two carbons of an optionally substituted phenyl ring linking the two carbonyls and forming the optionally substituted phenyl ring.

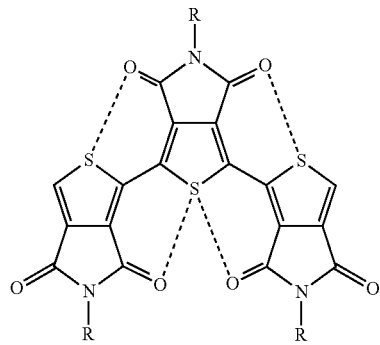

PP-4

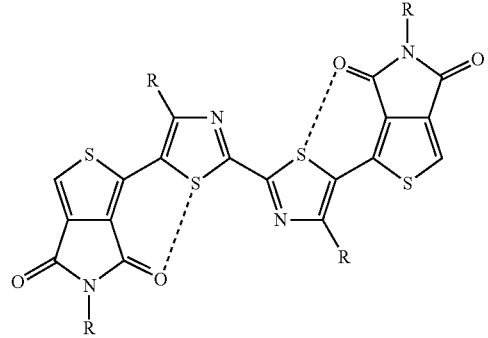

PP-5

Example

Synthesis of 1-bromo-5-(2-ethylhexyl)-4H-thieno[3,4-c]pyrrole-4,6(5H)-dione

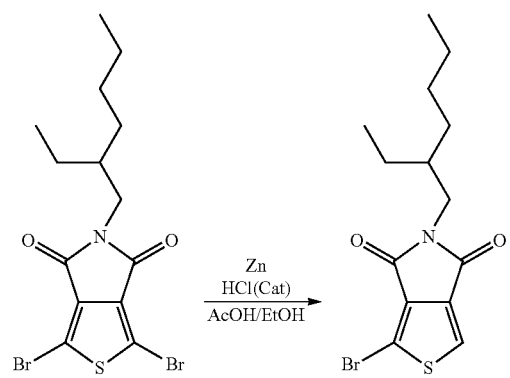 [SMILES: CCCCC(CC)CN1C(=O)c2c(Br)sc(Br)c2C1=O ; CCCCC(CC)CN1C(=O)c2csc(Br)c2C1=O]

1,3-Dibromo-5-(2-ethylhexyl)-4H-thieno[3,4-c]pyrrole-4,6(5H)-dione (2.6 g, 5 mmol) was placed in a three neck round-bottom flask equipped with a water condenser with ethanol (35 mL), acetic acid (10 mL) and three drops of 1 M HCl. The mixture was heated until the starting material was fully dissolved. At this point, zinc (310 mg, 5 mmol) was added in one portion. Mixture was refluxed for one hour after which an aliquot was taken for GC analysis and NMR, indicating reaction completion. After cooling, the solution was filtered through fitted glass to eliminate remaining Zn particles and solvent was evaporated under vacuum. Product was obtained by silica chromatography (1.1 g, 52%), using a 100% hexane to 100% CHCl$_3$ gradient.

Spectral data: $^1$H NMR (300 MHz, CDCl$_3$): $\delta_H$ 0.88 (t, 3H, 6.8 Hz), 0.9 (t, 3H, 7.4 Hz), 1.2-1.4 (m, 8H), 1.72-1.84 (m, 1H), 3.5 (d, 2H, 7.2 Hz), 7.72 (s, 1H).

Spectral data: $^1$H NMR (300 MHz, CDCl$_3$): $\delta_H$ 0.82-0.96 (m, 12H), 1.16-1.46 (m, 16H), 1.72-1.87 (m, 2H), 3.54 (d, 4H), 7.88 (s, 2H).

Example

Synthesis of 5,5'-bis(2-ethylhexyl)-4H,4'H-[1,1'-bithieno[3,4-c]pyrrole]-4,4',6,6'(5H,5'H)-tetraone Example Synthesis of 3,3'-dibromo-5,5'-bis(2-ethylhexyl)-4H,4'H-[1,1'-bithieno[3,4-c]pyrrole]-4,4',6,6'(5H,5'H)-tetraone

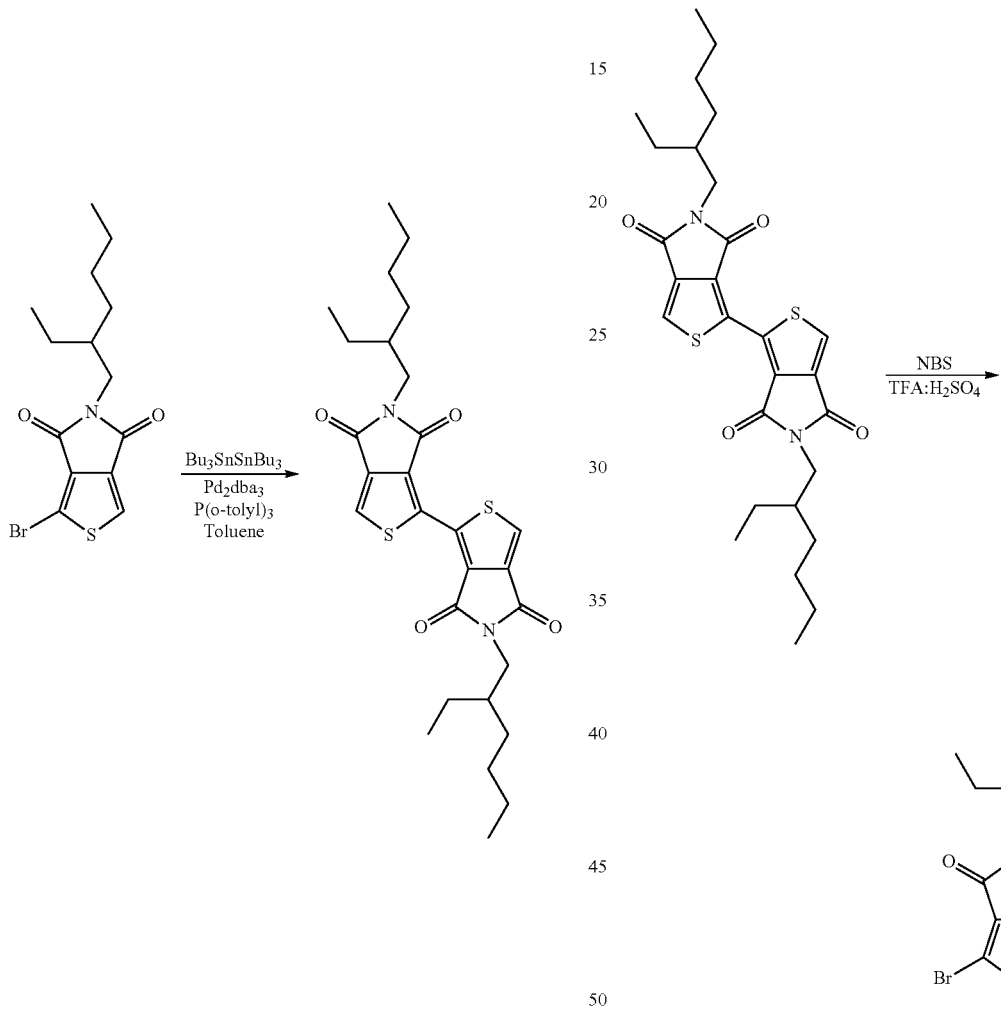

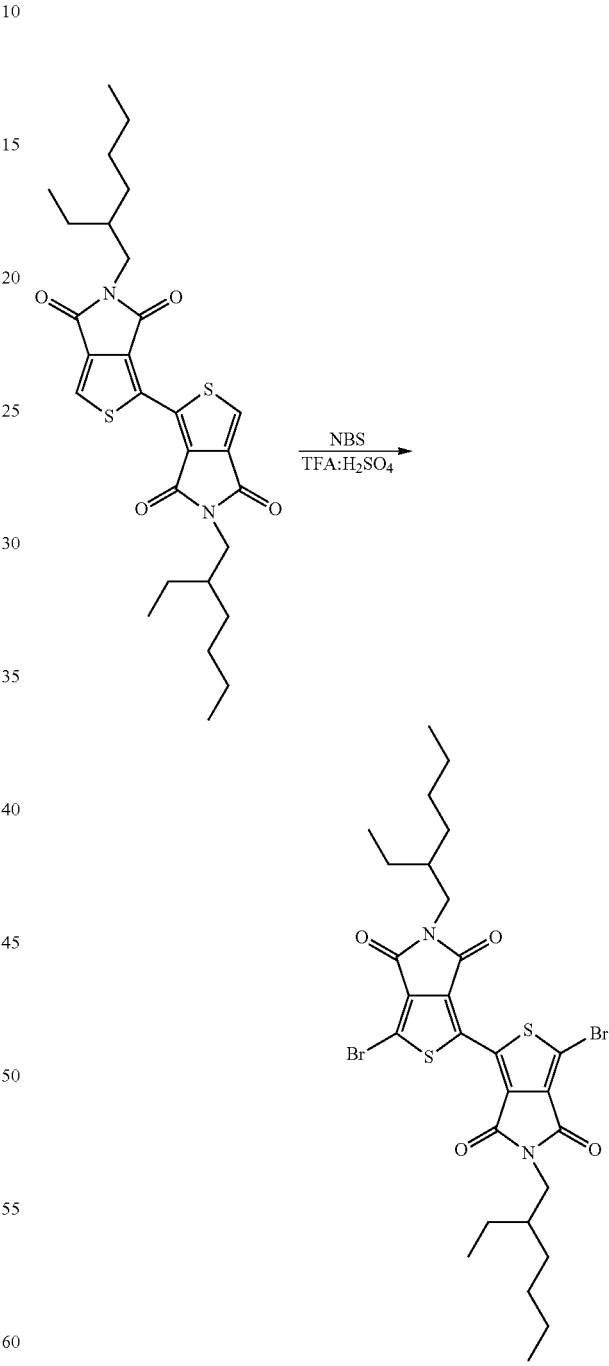

1-Bromo-5-(2-ethylhexyl)-4H-thieno[3,4-c]pyrrole-4,6(5H)-dione (2.2 g, 6 mmol), Pd$_2$dba$_3$ (137 mgs, 0.15 mmol), P(o-tolyl)$_3$ (182 mg, 0.6 mmol) and bis(tributyltin) (1.7 g, 3 mmol) were charged in a schlenk flask. Outside of the glove box, the flask was connected to argon line and toluene (40 ml, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with MgSO$_4$ and the solvent was evaporated after filtration. The final product is obtained as a yellow solid by Silica chromatography using a 100% hexane/100% chloroform gradient.

5,5'-Bis(2-ethylhexyl)-4H,4'H-[1,1'-bithieno[3,4-c]pyrrole]-4,4',6,6'(5H,5'H)-tetraone (1.7 g, 3.21 mmol) was dissolved in a 3:1 mixture of trifluoracetic acid (53 ml) and sulfuric acid (12 mL) in a 3-neck round bottom flask under nitrogen atmosphere, wrapped with aluminum foil and equipped with internal thermometer. N-bromosuccinimide (NBS) (1.26 g, 7.1 mmol, recrystallized before use) was added in one portion. An exotherm was observed immediately after addition, and the reaction was allowed to stir until the temperature was returned to room temperature. An aliquot was taken for NMR, which confirmed reaction was complete. The mixture was poured in ice-cold water and the aqueous solution was then extracted with $CHCl_3$. The organic phase was washed with water, dried with anhydrous $MgSO_4$ and the solvent was removed under vacuum. The mixture was purified by Silica column chromatography using a 100% hexane to 100% $CHCl_3$ gradient to yield a yellow solid (1.5 g, 70%).

Spectral data: $^1H$ NMR (300 MHz, $CDCl_3$): $\delta_H$ 0.82-0.96 (m, 12H), 1.2-1.4 (m, 16H), 1.72-1.86 (m, 2H), 3.54 (d, 4H).

Example

Synthesis of 1-bromo-5-(heptadecan-9-yl)-4H-thieno[3,4-c]pyrrole-4,6(5H)-dione under vacuum. Product was obtained by silica chromatography, using a 100% hexane to 100% $CHCl_3$ gradient.

Spectral data: $^1H$ NMR (300 MHz, $CDCl_3$): $\delta_H$ 0.8-0.9 (t, 6H), 1.13-1.34 (m, 24H), 1.56-1.72 (m, 2H), 1.92-2.08 (m, 2H), 4.02-4.16 (m, 1H), 7.7 (s, 1H).

Example

Synthesis of 5,5'-di(heptadecan-9-yl)-4H,4'H-[1,1'-bithieno[3,4-c]pyrrole]-4,4',6,6'(5H,5'H)-tetraone

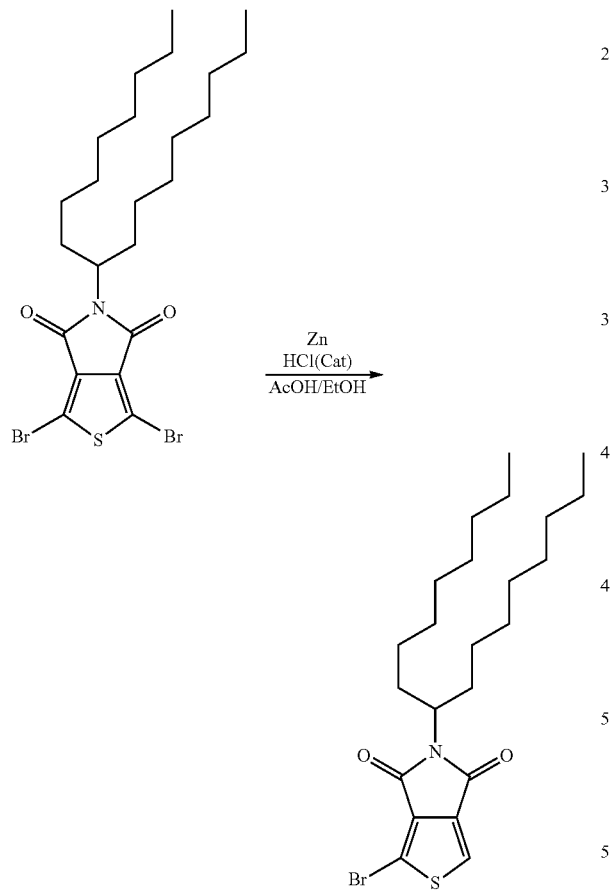

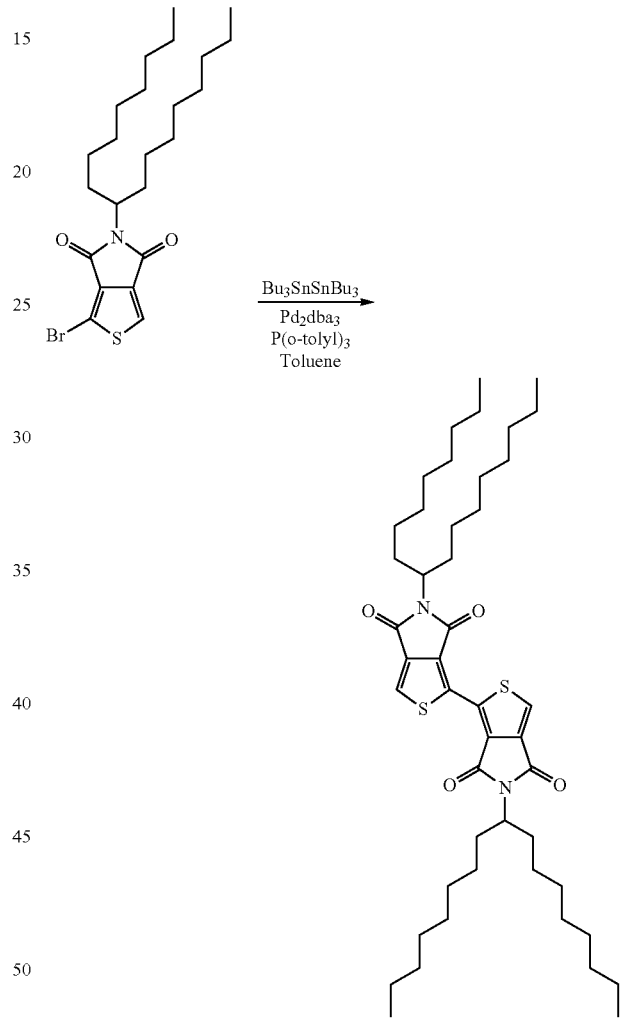

1-bromo-5-(heptadecan-9-yl)-4H-thieno[3,4-c]pyrrole-4,6(5H)-dione (575 mg, 1.22 mmol), $Pd_2dba_3$ (28 mg, 0.03 mmol), (o-tolyl)$_3$P (37.2 mg, 0.122 mmol) and bis(tributyltin) (0.31 mL, 0.61 mmol) were charged in a schlenk flask. Outside of the glove box, the flask was connected to argon line and toluene (10 mL, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with anhydrous $MgSO_4$ and the solvent was evaporated after filtration. The final product is 1,3-Dibromo-5-(heptadecan-9-yl)-4H-thieno[3,4-c]pyrrole-4,6(5H)-dione (9.43 g, 20.04 mmol) and zinc (1.31 g, 20.04 mmol) were placed in a 3 neck round-bottom flask equipped with a water condenser with ethanol (130 mL), acetic acid (40 mL) and 1 M HCl (2.5 mL). Mixture was refluxed for one hour after which an aliquot was taken for NMR analysis, which indicated reaction was complete. After cooling, the solution was filtered through fritted glass to eliminate remaining Zn particles and solvent was evaporated obtained as a yellow solid by Silica chromatography using a 100% hexane/100% chloroform gradient (347 mg, 36% yield).

Spectral data: $^1$H NMR (300 MHz, CDCl$_3$): $\delta_H$ 0.85 (broad t, 12H, 6.92 Hz), 1.12-1.36 (m, 48H), 1.58-1.76 (m, 4H), 1.95-2.13 (m, 4H), 4.07-4.2 (m, 2H), 7.86 (s, 2H).

$^{13}$C NMR (CDCl$_3$, 75 MHz): δ 14.31, 22.86, 26.92, 29.43, 29.5, 29.66, 32.04, 32.49, 53.26, 126.43, 132.55, 136.84.

Example

Synthesis of 3,3'-dibromo-5,5'-di(heptadecan-9-yl)-4H,4'H-[1,1'-bithieno[3,4-c]pyrrole]-4,4',6,6'(5H,5'H)-tetraone

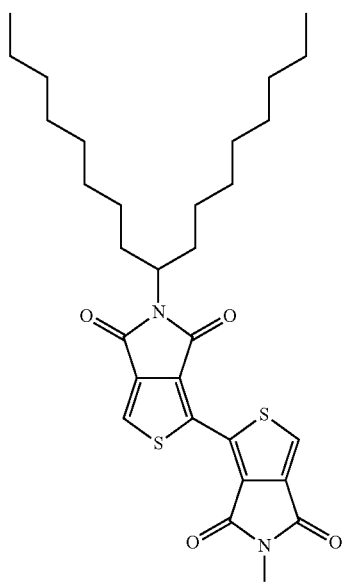

NBS
TFA:H$_2$SO$_4$

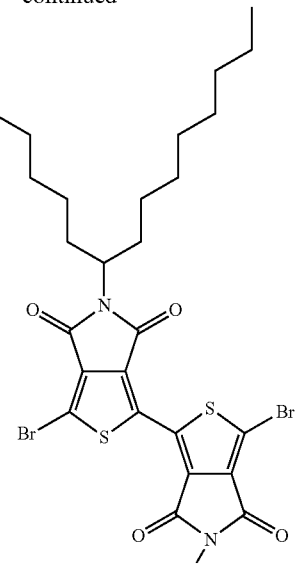

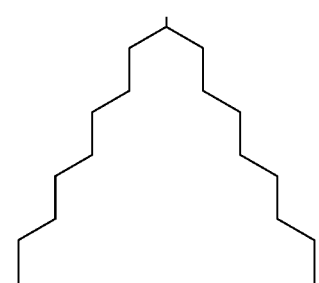

5,5'-Di(heptadecan-9-yl)-4H,4'H-[1,1'-bithieno[3,4-c]pyrrole]-4,4',6,6'(5H,5'H)-tetraone (347 mg, 0.444 mmol) was dissolved in a 4:1 mixture of trifluoroacetic acid (16 mL) and sulfuric acid (4 mL) in a 3-neck round bottom flask under nitrogen atmosphere, wrapped with aluminum foil and equipped with internal thermometer. N-bromosuccinimide (178 mg, 1 mmol, recrystallized before use) was added in one portion. An exotherm was observed immediately after addition, and the reaction was allowed to stir until the temperature was returned to room temperature. An aliquot was taken for NMR, which confirmed reaction was complete. The mixture was poured in ice-cold water and the aqueous solution was then extracted with CHCl$_3$. The organic phase was washed with water, dried with anhydrous MgSO$_4$ and the solvent was removed under vacuum. The mixture was purified by Silica column chromatography using a 100% hexane to 100% CHCl$_3$ gradient (406 mg, 97%).

Spectral data: $^1$H NMR (300 MHz, CDCl$_3$): $\delta_H$ 0.83 (t, 12H, 6.94); 1.1-1.32 (m, 48H), 1.57-1.73 (m, 4H), 1.9-2.08 (m, 4H), 4.02-4.17 (m, 2H).

$^{13}$C NMR (CDCl$_3$, 75 MHz): $\delta_H$ 14.06, 22.6, 26.66, 29.16, 29.21, 29.37, 31.77, 32.16, 53.67, 115.98, 132.57, 133.75, 134.04.

Example

Synthesis of 5-(heptadecan-9-yl)-1,3-di(thiophen-2-yl)-4H-thieno[3,4-c]pyrrole-4,6(5H)-dione

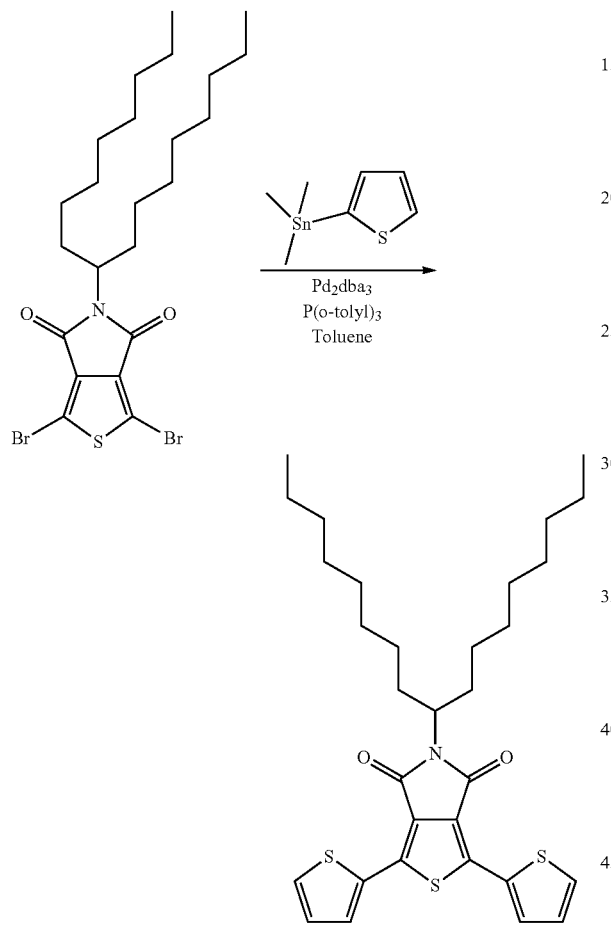

1,3-Dibromo-5-(heptadecan-9-yl)-4H-thieno[3,4-c]pyrrole-4,6(5H)-dione (2 g, 3.64 mmol), Pd$_2$dba$_3$ (167 mg, 0.18 mmol), (o-tolyl)$_3$P (221 mg, 0.72 mmol) and 2-trimethyltin-thiophene (3.4 g, 9.1 mmol) were charged in a schlenk flask. Outside of the glove box, the flask was connected to argon line and toluene (70 mL, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with MgSO$_4$ and the solvent was evaporated after filtration. The product was first purified by silica chromatography using a 100% hexane/100% chloroform gradient. The final product, a yellow solid was further purified by dissolution in chloroform followed by precipitation with methanol (1.2 g, 56%).

Spectral data: $^1$H NMR (300 MHz, CDCl$_3$): $\delta_H$ 0.8 (t, 6H, 7.22 Hz), 1.13-1.35 (m, 24H), 1.62-1.77 (m, 2H), 1.97-2.17 (m, 2H), 4.1-4.24 (m, 1H), 7.13 (dd, 2H, 3.7 Hz, 5.1 Hz), 7.44 (dd, 5.1 Hz, 1.1 Hz).

Example

Synthesis of 1,3-bis(5-bromothiophen-2-yl)-5-(heptadecan-9-yl)-4H-thieno[3,4-c]pyrrole-4,6(5H)-dione

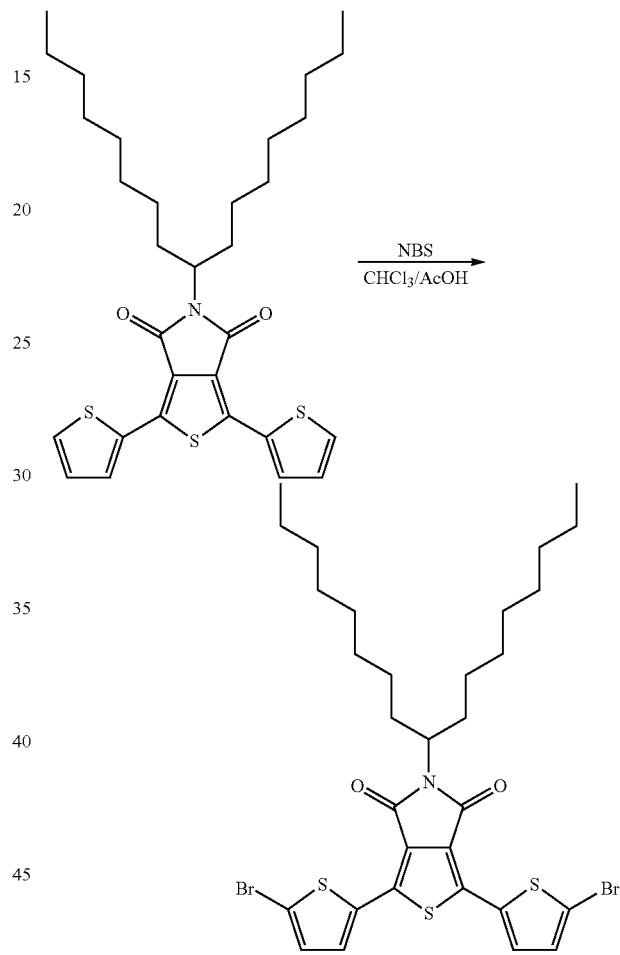

5-(Heptadecan-9-yl)-1,3-di(thiophen-2-yl)-4H-thieno[3,4-c]pyrrole-4,6(5H)-dione (0.62 g, 1.115 mmol) was dissolved in a 1:1 mixture of acetic acid (20 mL) and chloroform (20 mL) in a 3-neck round bottom flask under nitrogen atmosphere, wrapped with aluminum foil and equipped with internal thermometer. N-bromosuccinimide (0.4 g, 2.23 mmol, recrystallized before use) was added in one portion. An exotherm was observed immediately after addition, and the reaction was allowed to stir until the solution returned to room temperature. An aliquot was taken for NMR, which confirmed reaction was complete. The mixture was poured in ice-cold water and the aqueous solution was then extracted with CHCl$_3$. The organic phase was washed with water, dried with anhydrous MgSO$_4$ and the solvent was removed under vacuum. The mixture was purified by Silica column chromatography using a 100% hexane to 100% CHCl$_3$ gradient. The product is then further purified by first dissolving in the minimum amount of chloroform followed by a large amount of methanol to precipitate the pure product, obtained as a yellow solid after filtration (0.5 g, 63%).

Spectral data: $^1$H NMR (300 MHz, CDCl$_3$): $\delta_H$ 0.85 (t, 6H, 7 Hz), 1.17-1.31 Hz (m, 24H), 1.6-1.78 (m, 2H), 1.95-2.15 (m, 2H), 4.07-4.21 (m, 1H), 7.08 (d, 2H, 4.25 Hz), 7.64 (d, 2H, 4.25 Hz).

Example

Synthesis of 1,1'-(thiophene-2,5-diyl)bis(5-(2-ethylhexyl)-4H-thieno[3,4-c]pyrrole-4,6(5H)-dione)

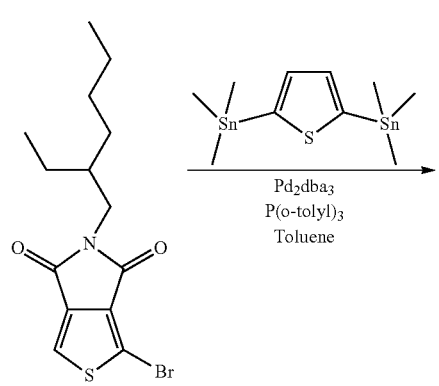

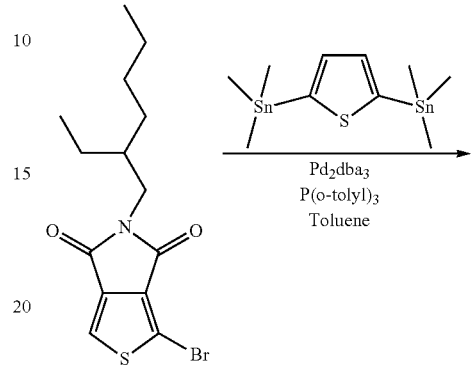

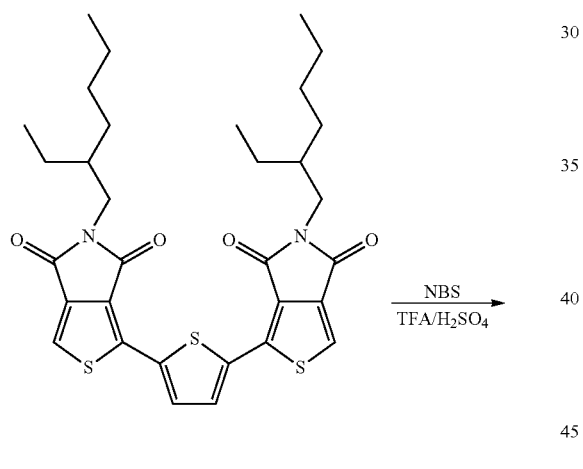

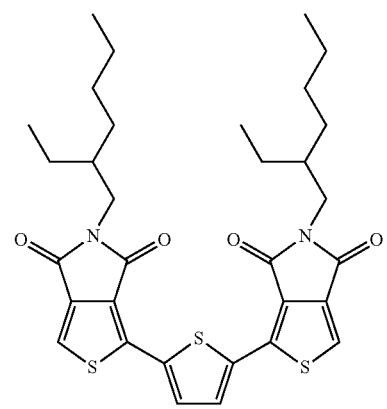

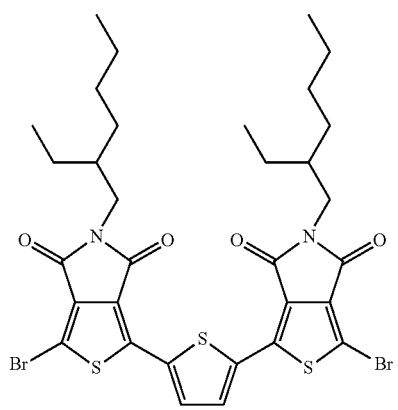

In a glove box, 1-bromo-5-(2-ethylhexyl)-4H-thieno[3,4-c]pyrrole-4,6(5H)-dione (1.55 g, 4.5 mmol), 2,5-bis(trimethyltin)-thiophene (0.74 g, 1.8 mmol), Pd$_2$dba$_3$ (41 mg, 0.045 mmol) and tris(o-tolyl)phosphine (55 mg, 0.18 mmol) were charged in a schlenk flask. Outside of the glove box, the flask was connected to argon line and toluene (11 mL, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with anhydrous MgSO$_4$ and the solvent was evaporated after filtration. The product was first purified by silica chromatography using a 100% hexane/100% chloroform gradient. The final product, a yellow solid was further purified by dissolution in chloroform followed by precipitation with methanol.

Spectral data: $^1$H NMR (300 MHz, CDCl$_3$): $\delta_H$ 0.92 (t, 12H, 7.33 Hz), 1.22-1.42 (m, 16H), 1.76-1.92 (m, 2H), 3.56 (d, 4H, 7.51 Hz), 7.67 (s, 2H), 8.02 (s, 2H).

Example

Synthesis of poly(3-(4,8-bis(heptan-3-yloxy)benzo[1,2-b:4,5-b']dithiophen-2-yl)-alt-5,5'-bis(2-ethylhexyl)-4H,4'H-[1,1'-bithieno[3,4-c]pyrrole]-4,4',6,6'(5H,5'H)-tetraone)

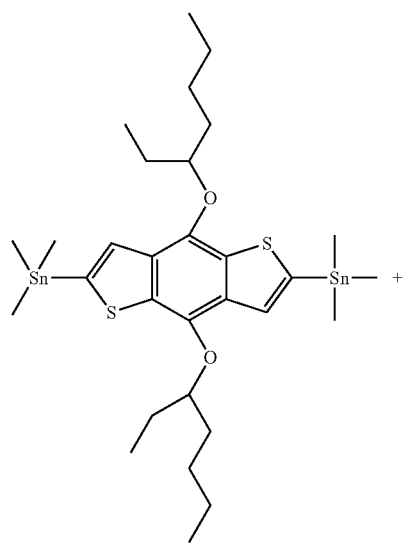

+

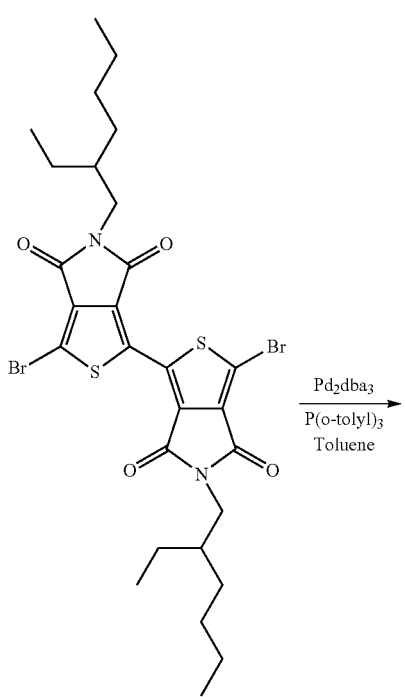

Pd$_2$dba$_3$
P(o-tolyl)$_3$
Toluene

-continued

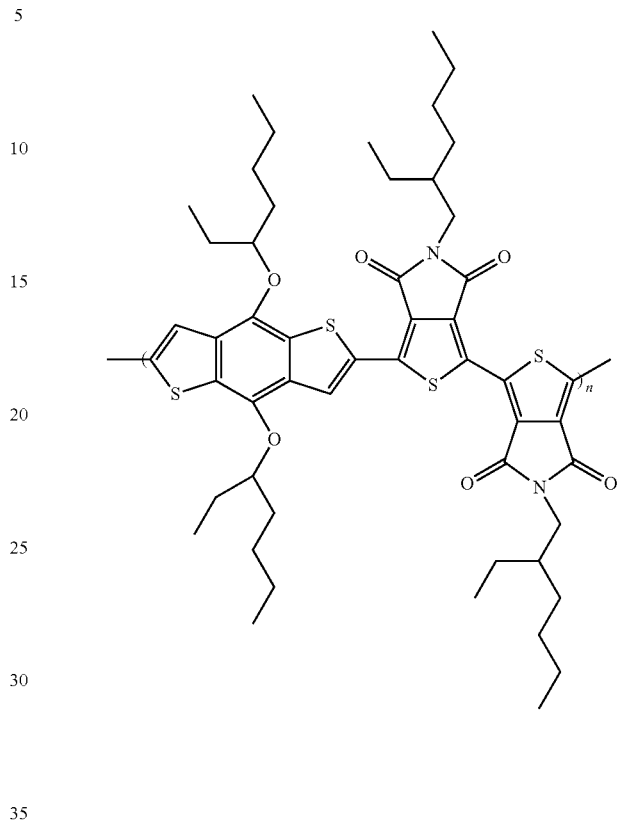

In a glove box, 3,3'-dibromo-5,5'-bis(2-ethylhexyl)-4H,4'H-[1,1'-bithieno[3,4-c]pyrrole]-4,4',6,6'(5H,5'H)-tetraone (267 mg, 0.388 mmol), (4,8-bis(2-ethylhexyl)benzo[1,2-b:4,5-b']dithiophene-2,6-diyl)bis(trimethylstannane) (300 mg, 0.39 mmol), Pd$_2$dba$_3$ (9 mg, 0.01 mmol), P(o-tolyl)$_3$ (12 mg, 0.04 mmol) were charged in a 100 mL schlenk flask. After connecting the flask to vac/argon line, the side arm was flushed with 5 vacuum-argon cycles and the flask was open to argon. Toluene (20 mL), degassed with argon overnight was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, hexane and chloroform (340 mg). Molecular weight was determined by GPC in chlorobenzene (1 mL/min at 80° C.) vs. polystyrene standards: $M_n$=25,000, $M_w$=137,500, PDI=5.5.

Example

Synthesis of poly(3-(4,8-bis(2-ethylhexyl)benzo[1,2-b:4,5-b']dithiophen-2-yl)-alt-5,5'-di(heptadecan-9-yl)-4H,4'H-[1,1'-bithieno[3,4-c]pyrrole]-4,4',6,6'(5H,5'H)-tetraone)

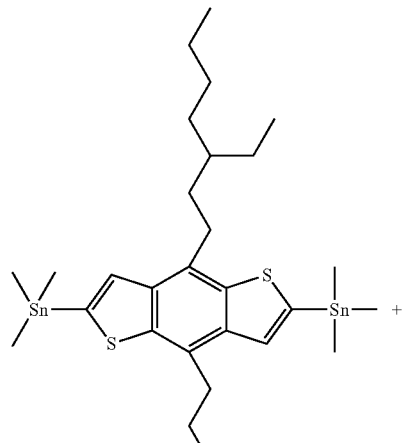

+

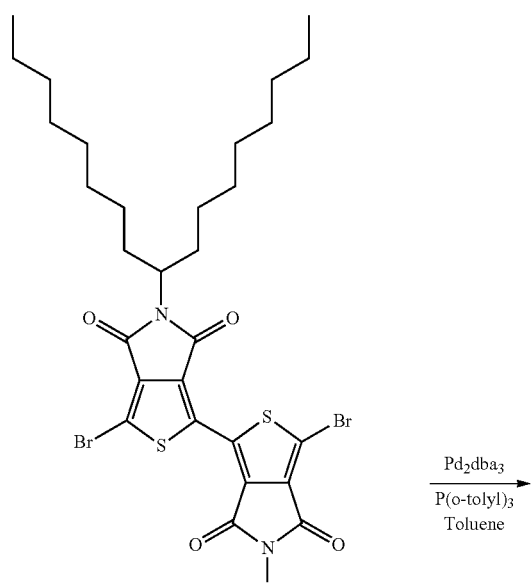

In a glove box, 3,3'-dibromo-5,5'-di(heptadecan-9-yl)-4H,4'H-[1,1'-bithieno[3,4-c]pyrrole]-4,4',6,6'(5H,5'H)-tetraone (0.454 mmol), (4,8-bis(2-ethylhexyl)benzo[1,2-b:4,5-b']dithiophene-2,6-diyl)bis(trimethylstannane) (0.454 mmol), Pd$_2$dba$_3$ (10.4 mg, 0.011 mmol), P(o-tolyl)$_3$ (13.8 mg, 0.044 mmol) were charged in a 100 mL schlenk flask. After connecting the flask to vac/argon line, the side arm was flushed with 5 vacuum-argon cycles and the flask was open to argon. Toluene (20 mL), degassed with argon overnight was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, hexane and chloroform (200 mg). Molecular weight was determined by GPC in chlorobenzene (1 mL/min at 80° C.) vs. polystyrene standards: $M_n$=27,300, $M_w$=62,800, PDI=2.3.

103

Example

Synthesis of poly(3-(4,8-bis(2-ethylhexyl)benzo[1,2-b:4,5-b']dithiophen-2-yl)-ran-5,5'-bis(2-ethylhexyl)-4H,4'H-[1,1'-bithieno[3,4-c]pyrrole]-4,4',6,6'(5H,5'H)-tetraone)

104

In a glove box, 3,3'-dibromo-5,5'-bis(2-ethylhexyl)-4H,4'H-[1,1'-bithieno[3,4-c]pyrrole]-4,4',6,6'(5H,5'H)-tetraone (180 mg, 0262 mmol), 2,6-dibromo-4,8-bis(3-ethylheptyl)benzo[1,2-b:4,5-b']dithiophene (77.4 mg, 0.129 mmol), (4,8-bis(2-ethylhexyl)benzo[1,2-b:4,5-b']dithiophene-2,6-diyl)bis(trimethylstannane) (300 mg, 0.390 mmol), Pd$_2$dba$_3$ (9.00 mg, 0.010 mmol), P(o-tolyl)$_3$ (12.0 mg, 0.040 mmol) were

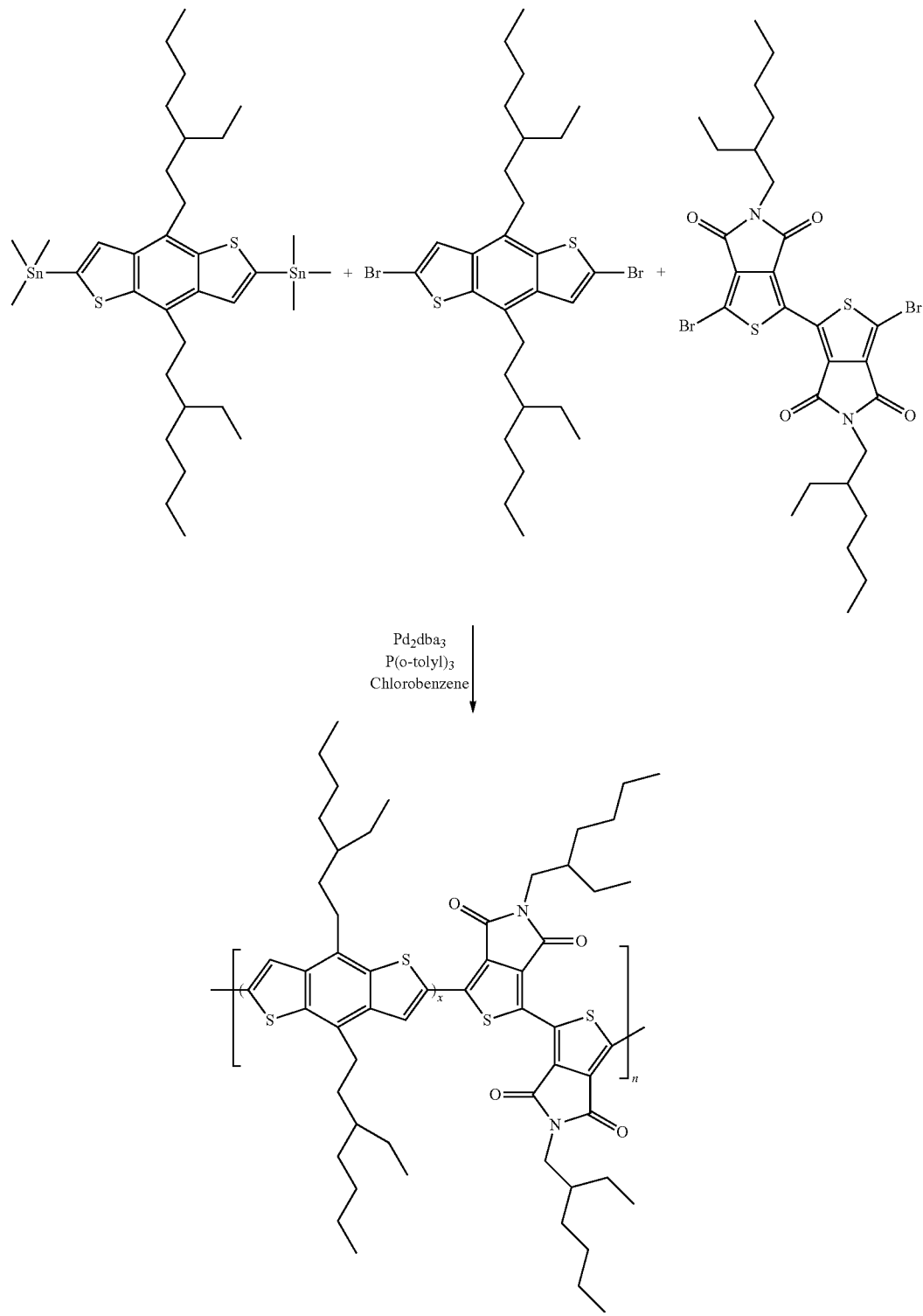

charged in a 50 mL Schlenk flask. After connecting the flask to vac/argon line, the side arm was flushed with 5 vacuum-argon cycles and the flask was open to argon. Chlorobenzene (10 mL), degassed with argon overnight, was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, (335 mg). Molecular weight was determined by GPC in chlorobenzene (1 mL/min at 80° C.) vs. polystyrene standards: $M_n$=7,000, $M_w$=12,600, PDI=1.8.

Example

Synthesis of poly{(3-4-(5,9-diethyltridecan-7-yl)-4H-dithieno[3,2-b:2',3'-d]pyrrol-2-yl)-alt-(5,5'-bis(2-ethylhexyl)-4H,4'H-[1,1'-bithieno[3,4-c]pyrrole]-4,4',6,6'(5H,5'H)-tetraone)}

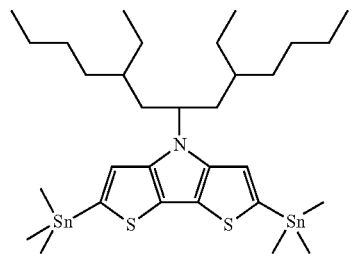

+

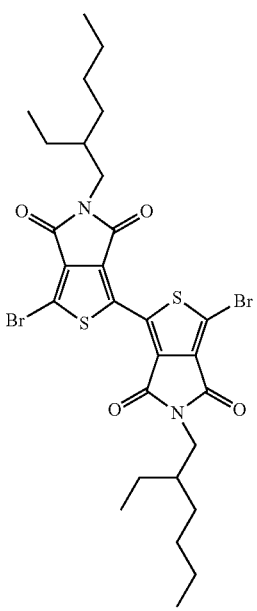

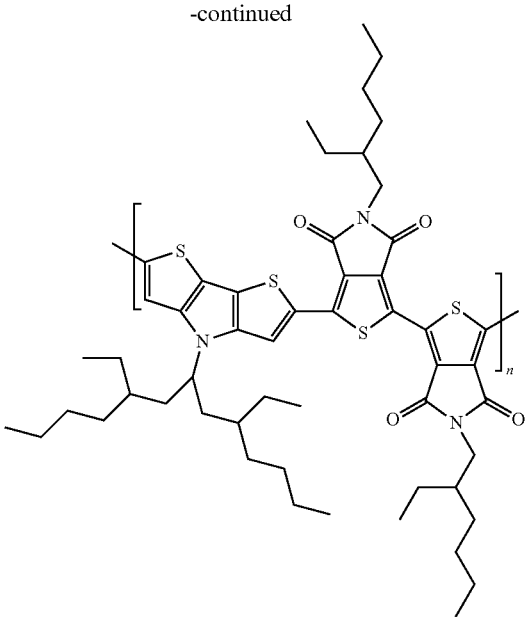

In a glove box, 4-(5,9-diethyltridecan-7-yl)-2,6-bis(trimethylstannyl)4H-dithieno[3,2-b:2',3'-d]pyrrole (0.30 g, 0.40 mmol), 1-bromo-3-[3-bromo-5-(2-ethylhexyl)-4,6-dioxothieno[3,4-c]pyrrol-1-yl]-5-(2-ethylhexyl)thieno[3,4-c]pyrrole-4,6-dione (0.28 g, 0.40 mmol), tris(dibenzylideneacetone)dipalladium(0) (9.2 mg, 0.010 mmol) and tris(o-tolyl)phosphine (12 mg, 0.040 mmol) were charged into a flame dried 50 mL Schlenk flask. The reaction flask was removed from the glove box and 10 mL of deoxygenated chlorobenzene were added via syringe. The mixture was evacuated and refilled with argon five times. The reaction flask was immersed into a 110° C. oil bath and left stirring under an argon stream for 2 days. After cooling to room temperature, 40 mL of methanol were added to the reaction mixture. The polymer was collected via filtration and purified by consecutive Soxhlet extractions in sequence with methanol, MTBE, hexane, and chloroform. The chloroform solution was passed through celite to remove catalyst residuals, and solvent was removed under vacuum to yield polymer. The polymer was re-dissolved in a small amount of chloroform, re-precipitated in the mixture of IPA, water and methanol, isolated via centrifuge and dried to yield 64% of polymer. Molecular weight was determined by GPC in chlorobenzene (1 mL/min at 80° C.) vs. polystyrene standards: $M_n$=24,400, $M_w$=47,300, PDI=1.9.

Example

Synthesis of 4,8-dimethylbenzo[1,2-b:4,5-b']dithiophene

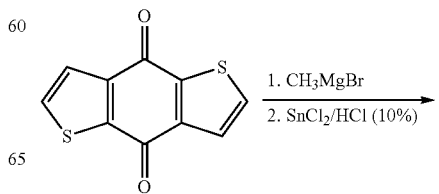

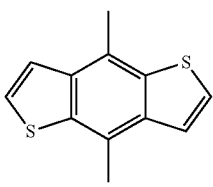

A dry 250-mL three-neck flask equipped with a reflux condenser and an addition funnel was flushed with N₂ and was charged with a 1 M solution of methylmagnesium bromide (11 mL) in THF via deoxygenated syringe. A 0.1 M solution of benzo[1,2-b:4,5-b']dithiophene-4,8-dione (1.0 g, 4.5 mmol) in THF (40 mL) was added portion-wise. The reaction was heated to reflux for 1 hour. As the reaction was completed, the flask was cooled to ambient temperature and a solution of SnCl₂ (2.1 g) dissolved in 10% HCl (20 mL) was added to the reaction flask. The stirring continued with increasing temperature to reflux for 1 hour and then cooling the reaction to ambient temperature. The reaction was poured into 100 mL of cool water with 10 mL of 10% HCl and extracted with CHCl₃ (100 mL) three times. The combined organic layer was dried over anhydrous magnesium sulfate (MgSO₄). After the product was filtered, the solvent was removed by rotary evaporation. The product was purified using column chromatography on silica gel with hexanes/chloroform (gradient) to yield white solid (0.46 g, 40%).

Spectral data: ¹H NMR (300 MHz, CDCl₃): $\delta_H$ 7.42 (dd, 4H), 2.8 (s, 6H).

Example

Synthesis of (4,8-dimethylbenzo[1,2-b:4,5-b']dithiophene-2,6-diyl)bis(trimethylstannane)

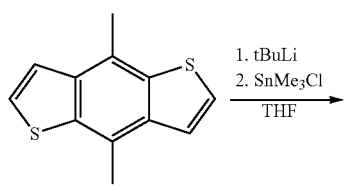

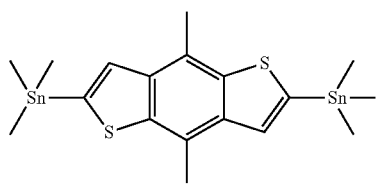

A dry 250-mL three-neck round bottom flask was flushed with N₂ and was charged with 4,8-dimethylbenzo[1,2-b:4,5-b']dithiophene (1.02 g, 4.70 mmol) and anhydrous tetrahydrofuran (THF) (75.0 mL, 0.01 M) via deoxygenated syringe. The reaction flask was cooled to −78° C. and a 1.3 M solution of tert-butyllithium in hexanes (9.00 mL, 23.0 mmol) was added drop-wise via deoxygenated syringe. After 30 minutes of stirring at −78° C., the solution was chilled to 0° C. and stirring was continued for 5 minutes, at which point the reaction mixture was cooled back to −78° C. A 1 M solution of trimethyltin chloride (19.0 mL, 37.0 mmol) in hexanes was added to the reaction flask dropwise and stirring continued for 30 minutes at −76° C. The cooling bath was removed and the reaction mixture was allowed to warm to ambient temperature. As the reaction was completed, cool DI water (10 mL) was slowly added to the reaction flask. Then, the reaction mixture was poured into 50 mL of cool water and extracted with MTBE (100 mL) three times. The combined organic layer was washed with water two times and dried over anhydrous magnesium sulfate (MgSO₄). After the product was filtered, the solvent was removed by rotary evaporation. The crude product was purified by precipitation into methanol from a THF solution to yield white solid (1.90 g, 74%).

Spectral data: ¹H NMR (300 MHz, CDCl₃): $\delta_H$ 7.59 (s, 2H), 2.8 (s, 6H), 0.54 (s, 18H).

Example

Synthesis of 2,6-bis(trimethylstannyl)benzo[1,2-b:4,5-b']dithiophene

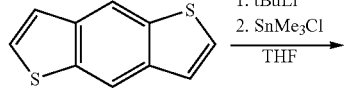

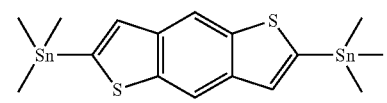

A dry 1 L three-neck round bottom flask was flushed with N₂ and was charged with benzo[1,2-b:4,5-b']dithiophene (5.20 g, 26.3 mmol) and anhydrous tetrahydrofuran (THF) (300 mL, 0.01 M) via deoxygenated syringe. The reaction flask was cooled to −78° C. and a 1.3 M solution of tert-butyl lithium in hexanes (53.0 mL, 68.8 mmol) was added dropwise via deoxygenated syringe. After 30 minutes of stirring at −78° C., the solution was chilled to 0° C. and stirring was continued for 5 minutes, at which point the reaction mixture was cooled back to −78° C. A 1 M solution of trimethyltin chloride (105 mL, 100 mmol) in hexanes was added to the reaction flask dropwise and stirring continued for 30 minutes at −76° C. The cooling bath was removed and the reaction mixture was allowed to warm to ambient temperature. As the reaction was completed, cool DI water (50 mL) was slowly added to the reaction flask. Then, the reaction mixture was poured into 300 mL of cool water and extracted with MTBE (300 mL) three times. The combined organic layer was washed with water two times and dried over anhydrous magnesium sulfate (MgSO₄). After the product was filtered, the solvent was removed by rotary evaporation. The crude product was purified by precipitation into methanol from a THF solution to yield white solid (12.0 g, 88%).

Spectral data: $^1$H NMR (300 MHz, CDCl$_3$): $\delta_H$ 8.24 (s, 2H), 7.42 (s, 2H), 0.42 (s, 18H).

Example

Synthesis of poly(3-(4,8-dimethylbenzo[1,2-b:4,5-b']dithiophen-2-yl)-alt-5,5'-di(heptadecan-9-yl)-4H,4'H-[1,1'-bithieno[3,4-c]pyrrole]-4,4',6,6'(5H,5'H)-tetraone)

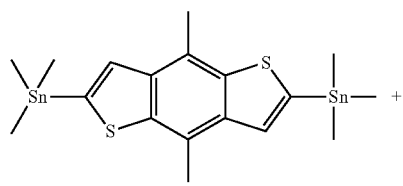

+

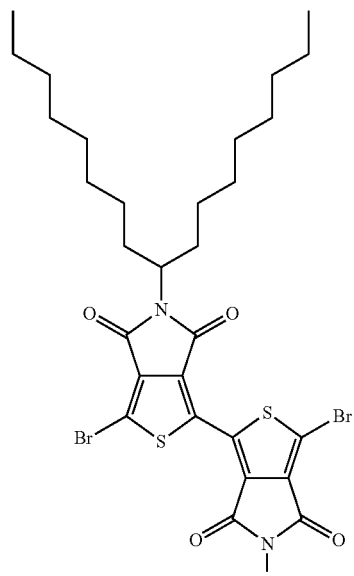

$\xrightarrow[\text{Chlorobenzene}]{\text{Pd}_2\text{dba}_3, \text{P(o-tolyl)}_3}$

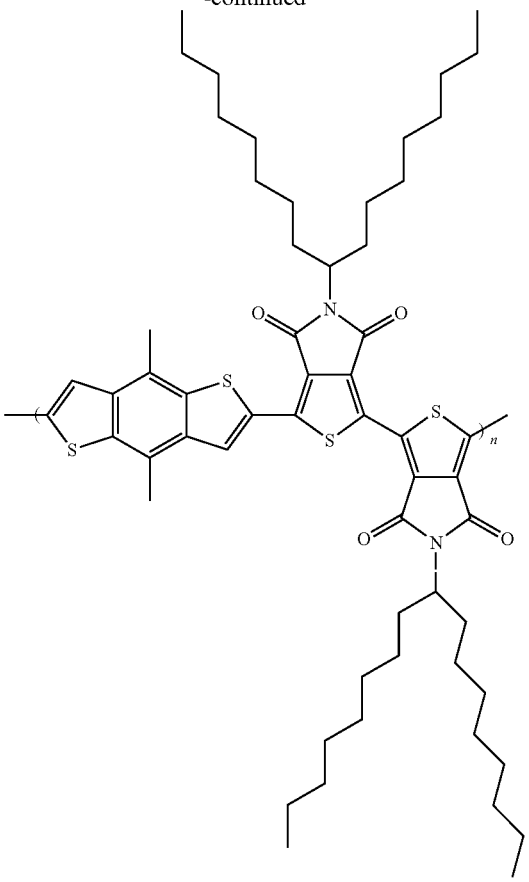 [SMILES: CCCCCCCCC(CCCCCCCC)N1C(=O)c2c(C)sc(-c3sc(-c4cc5c(C)c6sc(C)cc6c(C)c5s4)c4c3C(=O)N(C(CCCCCCCC)CCCCCCCC)C4=O)c2C1=O]

In a glove box, 3,3'-dibromo-5,5'-di(heptadecan-9-yl)-4H,4'H-[1,1'-bithieno[3,4-c]pyrrole]-4,4',6,6'(5H,5'H)-tetraone (345.2 mg, 0.37 mmol), (4,8-dimethylbenzo[1,2-b:4,5-b']dithiophene-2,6-diyl)bis(trimethylstannane) (200 mg, 0.37 mmol), Pd$_2$dba$_3$ (9 mg, 0.0098 mmol), P(o-tolyl)$_3$ (12 mg, 0.039 mmol) were charged in a 100 mL schlenk flask. After connecting the flask to vac/argon line, the side arm was flushed with 5 vacuum-argon cycles and the flask was open to argon. Chlorobenzene (20 mL, degassed with argon overnight) was added. The flask was purged five times through vacuum-argon cycles, then placed in a preheated flask at 110° C. for 48 hours. After cooling, methanol was added to precipitate the polymer. The polymer was filtered through Soxhlet thimble and Soxhlet purification was performed with methanol, MTBE, hexane. The polymer was extracted through CHCl$_3$ Soxhlet, and obtained as a reflective brown solid after solvent evaporation under vacuum (250 mg).

Example

Synthesis of poly(3-(benzo[1,2-b:4,5-b']dithiophen-2-yl)-alt-5,5'-bis(1-octylnonyl)-4H,4'H-[1,1'-bithieno[3,4-c]pyrrole]-4,4',6,6'(5H,5'H)-tetraone)

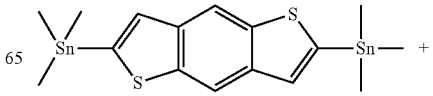

+

111
-continued

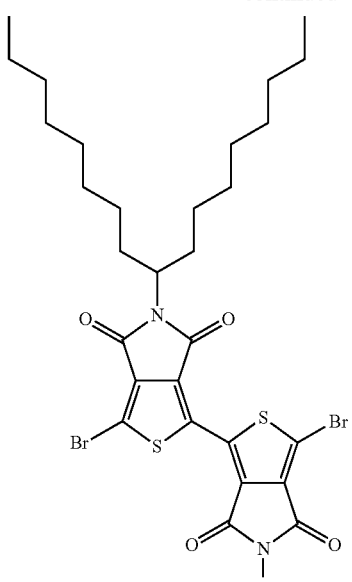

112
-continued

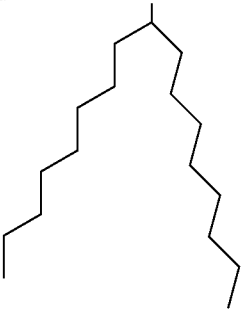

In a glove box, 3,3'-dibromo-5,5'-di(heptadecan-9-yl)-4H, 4'H-[1,1'-bithieno[3,4-c]pyrrole]-4,4',6,6'(5H,5'H)-tetraone (364 mg, 0.388 mmol), benzo[1,2-b:4,5-b']dithiophene-2,6-diyl)bis(trimethylstannane) (200 mg, 0.388 mmol), $Pd_2dba_3$ (9 mg, 0.0098 mmol) and $P(o-tolyl)_3$ (12 mg, 0.039 mmol) were charged in a 100 mL schlenk flask. After connecting the flask to vac/argon line, the side arm was flushed with 5 vacuum-argon cycles and the flask was open to argon. Chlorobenzene (20 mL, degassed with argon overnight) was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, hexane and chloroform. After drying, polymer was collected from thimble as a reflective brown solid (210 mg)

What is claimed is:

1. A device comprising:
   at least one cathode;
   at least one anode;
   at least one photovoltaic active layer disposed between the cathode and anode and comprising at least one p-type material and at least one n-type material, wherein the p-type material comprises at least one polymer comprising a polymer backbone moiety:

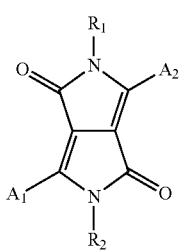

(VIII)

wherein $A_1$ and $A_2$ each independently comprise a fused ring system comprising at least two fused rings directly covalently linked to the substructure of VIII represented as substructure IX:

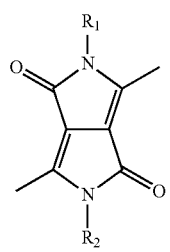

(IX)

wherein R groups $R_1$ and $R_2$ each comprise optionally substituted alkyl, optionally substituted linear alkyl, optionally substituted branched alkyl, optionally substituted cycloalkyl, optionally substituted aryl, optionally substituted alkylaryl, optionally substituted arylalkyl, optionally substituted alkoxy, or optionally substituted aryloxy, and optionally, wherein R groups $R_1$ and $R_2$ further comprises fluorine, and wherein the polymer comprises a donor-acceptor structure, and $A_1$ and $A_2$ comprise the donor which comprises at least one tricyclic unit comprising three fused rings.

2. The device of claim 1, wherein the fused ring systems comprise at least one thiophene fused ring, wherein the thiophene ring is directly linked to the substructure IX.

3. The device of claim 1, wherein the polymer does not comprise equal amounts of donor and acceptor.

4. The device of claim 1, wherein the donor comprises a silole.

5. The device of claim 1, wherein $A_1$ and $A_2$ each independently do not comprise an unfused thiophene or unfused benzene ring.

6. The device of claim 1, wherein the at least two fused rings form part of the backbone and none of the fused rings form side groups to the backbone.

7. A device comprising:
at least one cathode;
at least one anode;
at least one photovoltaic active layer disposed between the cathode and anode and comprising at least one p-type material and at least one n-type material, wherein the p-type material comprises at least one polymer comprising a polymer backbone moiety:

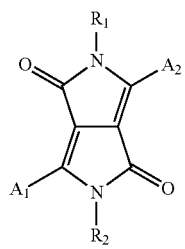

(VIII)

wherein $A_1$ and $A_2$ each independently comprise a fused ring system comprising at least two fused rings directly covalently linked to the substructure of VIII represented as substructure IX:

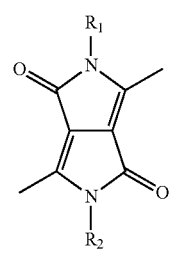

(IX)

wherein R groups $R_1$ and $R_2$ each comprise optionally substituted alkyl, optionally substituted linear alkyl, optionally substituted branched alkyl, optionally substituted cycloalkyl, optionally substituted aryl, optionally substituted alkylaryl, optionally substituted arylalkyl, optionally substituted alkoxy, or optionally substituted aryloxy, and optionally, wherein R groups $R_1$ and $R_2$ further comprises fluorine, and wherein the polymer comprises a donor-acceptor structure, and the polymer comprises at least one acceptor represented by VIII and at least one donor which is a triarylamine.

8. The device of claim 7, wherein the fused ring systems comprise at least one thiophene fused ring, wherein the thiophene ring is directly linked to the substructure IX.

9. The device of claim 7, wherein the polymer does not comprise equal amounts of donor and acceptor.

10. The device of claim 7, wherein the donor comprises a silole.

11. The device of claim 7, wherein $A_1$ and $A_2$ each independently do not comprise an unfused thiophene or unfused benzene ring.

12. The device of claim 7, wherein the at least two fused rings form part of the backbone and none of the fused rings form side groups to the backbone.

13. A device comprising:
at least one cathode;
at least one anode;
at least one photovoltaic active layer disposed between the cathode and anode and comprising at least one p-type material and at least one n-type material, wherein the p-type material comprises at least one polymer comprising a polymer backbone moiety:

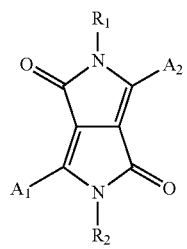

(VIII)

wherein $A_1$ and $A_2$ each independently comprise a fused ring system comprising at least two fused rings directly covalently linked to the substructure of VIII represented as substructure IX:

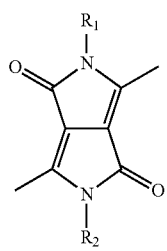

(IX)

wherein R groups $R_1$ and $R_2$ each comprise optionally substituted alkyl, optionally substituted linear alkyl, optionally substituted branched alkyl, optionally substituted cycloalkyl, optionally substituted aryl, optionally substituted alkylaryl, optionally substituted arylalkyl, optionally substituted alkoxy, or optionally substituted aryloxy, and optionally, wherein R groups $R_1$ and $R_2$ further comprises fluorine, and wherein the polymer comprises a donor-acceptor structure, and the donor is a symmetrical moiety.

14. The device of claim 13, wherein the fused ring systems comprise at least one thiophene fused ring, wherein the thiophene ring is directly linked to the substructure IX.

15. The device of claim 13, wherein the polymer comprises a donor-acceptor structure, but does not comprise equal amounts of donor and acceptor.

16. The device of claim 13, wherein the donor comprises a silole.

17. The device of claim 13, wherein $A_1$ and $A_2$ each independently do not comprise an unfused thiophene or unfused benzene ring.

18. The device of claim 13, wherein the at least two fused rings form part of the backbone and none of the fused rings form side groups to the backbone.

19. The device of claim 13, wherein the donor comprises at least one tricyclic unit comprising three fused rings.

20. The device of claim 13, wherein at least one donor is a triarylamine.

* * * * *